(12) United States Patent
Bancroft et al.

(10) Patent No.: US 9,028,728 B2
(45) Date of Patent: May 12, 2015

(54) PHOTOCHROMIC MATERIALS THAT INCLUDE INDENO-FUSED NAPHTHOPYRANS

(75) Inventors: Kevin E. Bancroft, Pittsburgh, PA (US);
Anu Chopra, Pittsburgh, PA (US);
Xiao-Man Dai, Export, PA (US);
Beon-Kyu Kim, Gibsonia, PA (US);
David B. Knowles, Apollo, PA (US);
Jason R. Lewis, Monaca, PA (US);
Victor A. Montes, Monroeville, PA (US); Stephen D. Straight, Austin, TX (US); Massimiliano Tomasulo, Monroeville, PA (US); Barry Van Gemert, Delmont, PA (US); Robert W. Walters, Export, PA (US); Wenjing Xiao, Murrysville, PA (US); Huayun Yu, Monroeville, PA (US); Elizabeth A. Zezinka, Cranberry Township, County of Butler, PA (US)

(73) Assignee: Transitions Optical, Inc., Pinellas Park, FL (US)

(*) Notice: Subject to any disclaimer, the term of this patent is extended or adjusted under 35 U.S.C. 154(b) by 0 days.

(21) Appl. No.: 13/314,297

(22) Filed: Dec. 8, 2011

(65) Prior Publication Data
US 2012/0145973 A1 Jun. 14, 2012

Related U.S. Application Data

(60) Continuation-in-part of application No. 12/873,735, filed on Sep. 1, 2010, now Pat. No. 8,147,725, which is a continuation-in-part of application No. 12/136,339, filed on Jun. 10, 2008, now abandoned, which is a division of application No. 11/102,279, filed on Apr. 8, 2005, now abandoned.

(51) Int. Cl.
| | | |
|---|---|---|
| G02B 5/23 | (2006.01) |
| C07D 405/04 | (2006.01) |
| C07D 405/10 | (2006.01) |
| C07D 407/12 | (2006.01) |
| C07D 409/04 | (2006.01) |
| C07D 493/04 | (2006.01) |
| C07D 495/04 | (2006.01) |
| C09K 9/02 | (2006.01) |
| G03C 1/73 | (2006.01) |
| C07D 311/78 | (2006.01) |
| C07D 311/94 | (2006.01) |
| G03C 1/00 | (2006.01) |
| G03C 1/685 | (2006.01) |

(52) U.S. Cl.
CPC ............ *C07D 405/04* (2013.01); *C07D 311/94* (2013.01); *G02B 5/23* (2013.01); *C07D 311/78* (2013.01); *C07D 405/10* (2013.01); *C07D 407/12* (2013.01); *C07D 409/04* (2013.01); *C07D 493/04* (2013.01); *C07D 495/04* (2013.01); *C09K 9/02* (2013.01); *C09K 2211/1007* (2013.01); *C09K 2211/1011* (2013.01); *C09K 2211/1022* (2013.01); *C09K 2211/1033* (2013.01); *C09K 2211/1059* (2013.01); *C09K 2211/1088* (2013.01); *G03C 1/685* (2013.01); *G03C 1/73* (2013.01)

(58) Field of Classification Search
USPC .......... 252/586, 582; 544/130, 363, 364, 375, 544/150, 333, 31, 99, 338, 401; 546/196, 546/167; 549/382, 381; 548/311.4; 351/159.01; 365/119; 428/411.1
See application file for complete search history.

(56) References Cited

U.S. PATENT DOCUMENTS

| | | |
|---|---|---|
| 3,933,509 A | 1/1976 | Noguchi et al. |
| 4,929,693 A | 5/1990 | Akashi et al. |
| 4,931,220 A | 6/1990 | Haynes et al. |
| 5,066,818 A | 11/1991 | Gemert et al. |
| 5,166,345 A | 11/1992 | Akashi et al. |
| 5,236,958 A | 8/1993 | Miyashita |
| 5,238,981 A | 8/1993 | Knowles |
| 5,252,742 A | 10/1993 | Miyashita |
| 5,274,132 A | 12/1993 | VanGemert |
| 5,359,085 A | 10/1994 | Iwamoto et al. |

(Continued)

FOREIGN PATENT DOCUMENTS

| | | |
|---|---|---|
| EP | 0446717 A2 | 9/1991 |
| EP | 1038870 A1 | 9/2000 |

(Continued)

OTHER PUBLICATIONS

Araujo, R. J. et al., "Photochromism," Techniques in Chemistry, 1971, pp. 734-853, vol. III, Chapter 3, Glenn H. Brown, Editor, Wiley-Interscience a Division of John Wiley & Sons, Inc.

*Primary Examiner* — Bijan Ahvazi
(74) *Attorney, Agent, or Firm* — The Webb Law Firm

(57) ABSTRACT

The present invention relates to photochromic materials that include one or more indeno-fused naphthopyrans that have particular groups at the 7, 11, and 13 positions thereof, and at the position alpha to the oxygen of the pyran ring thereof. With some embodiments, hydrogen or an alkoxy group is bonded to the 7 position, an optionally substituted phenyl is bonded to the 11 position, two alkyl groups are bonded to the 13 position, and two optionally substituted phenyl groups are bonded to the position alpha to the oxygen of the pyran ring of the indeno-fused naphthopyran compound. The 13 position of the indeno-fused naphthopyrans is free of ether groups in which an ether oxygen is bonded to the 13 position, and hydroxyl. The present invention also relates to photochromic articles and compositions that include such indeno-fused naphthopyrans.

13 Claims, No Drawings

(56) References Cited

U.S. PATENT DOCUMENTS

| | | |
|---|---|---|
| 5,458,814 A | 10/1995 | Kumar et al. |
| 5,578,252 A | 11/1996 | Van Gemert et al. |
| 5,645,767 A | 7/1997 | Van Gemert |
| 5,645,768 A | 7/1997 | Melzig et al. |
| 5,650,098 A | 7/1997 | Kumar et al. |
| 5,651,923 A | 7/1997 | Kumar et al. |
| 5,658,501 A | 8/1997 | Kumar et al. |
| 5,698,141 A | 12/1997 | Kumar |
| 5,707,557 A | 1/1998 | Melzig et al. |
| 5,723,072 A | 3/1998 | Kumar |
| 5,753,146 A | 5/1998 | Van Gemert et al. |
| 5,770,115 A | 6/1998 | Misura |
| 5,811,034 A | 9/1998 | Lin |
| 5,821,287 A | 10/1998 | Hu et al. |
| 5,952,515 A | 9/1999 | Melzig et al. |
| 5,955,520 A | 9/1999 | Heller et al. |
| 5,961,892 A | 10/1999 | Gemert et al. |
| 6,018,059 A | 1/2000 | Chan |
| 6,022,497 A | 2/2000 | Kumar |
| 6,025,026 A | 2/2000 | Smith et al. |
| 6,036,890 A | 3/2000 | Melzig et al. |
| 6,068,797 A | 5/2000 | Hunt |
| 6,096,246 A | 8/2000 | Chan et al. |
| 6,113,814 A | 9/2000 | Gemert et al. |
| 6,146,554 A | 11/2000 | Melzig et al. |
| 6,150,430 A | 11/2000 | Walters et al. |
| 6,153,126 A | 11/2000 | Kumar |
| 6,187,444 B1 | 2/2001 | Bowles, III et al. |
| 6,190,580 B1 | 2/2001 | Melzig et al. |
| 6,225,466 B1 | 5/2001 | Mann et al. |
| 6,296,785 B1 | 10/2001 | Nelson et al. |
| 6,340,765 B1 * | 1/2002 | Momoda et al. ............... 549/330 |
| 6,392,043 B1 | 5/2002 | Bourchteine et al. |
| 6,398,987 B1 | 6/2002 | Breyne et al. |
| 6,399,791 B1 | 6/2002 | Breyne et al. |
| 6,469,076 B1 | 10/2002 | Momoda et al. |
| 6,506,322 B1 | 1/2003 | Breyne et al. |
| 6,555,028 B2 | 4/2003 | Walters et al. |
| 6,630,597 B1 | 10/2003 | Lin et al. |
| 6,641,874 B2 | 11/2003 | Kuntz et al. |
| 6,683,709 B2 | 1/2004 | Mann et al. |
| 6,719,925 B1 | 4/2004 | Breyne et al. |
| 6,723,859 B2 | 4/2004 | Kawabata et al. |
| 6,747,145 B2 | 6/2004 | Zhao et al. |
| 6,846,892 B2 | 1/2005 | Kindt-Larsen et al. |
| 6,852,254 B2 | 2/2005 | Spaulding et al. |
| 6,939,007 B2 | 9/2005 | Zhao et al. |
| 6,963,003 B2 | 11/2005 | Qin |
| 7,008,568 B2 | 3/2006 | Qin |
| 7,074,943 B2 | 7/2006 | Qin |
| 7,166,357 B2 | 1/2007 | Kumar et al. |
| 7,247,262 B2 | 7/2007 | Evans et al. |
| 7,256,246 B2 | 8/2007 | Kindt-Larsen et al. |
| 7,262,295 B2 | 8/2007 | Walters et al. |
| 7,320,826 B2 | 1/2008 | Kumar et al. |
| 7,368,072 B2 | 5/2008 | Gemert et al. |
| 7,410,691 B2 | 8/2008 | Blackburn et al. |
| 7,527,754 B2 | 5/2009 | Chopra |
| 7,556,750 B2 | 7/2009 | Xiao et al. |
| 7,807,075 B2 | 10/2010 | Evans et al. |
| 2001/0025948 A1 * | 10/2001 | Walters et al. ............... 252/586 |
| 2001/0039356 A1 | 11/2001 | Chan et al. |
| 2003/0000028 A1 | 1/2003 | Molock et al. |
| 2003/0071247 A1 | 4/2003 | Petrovskaia et al. |
| 2003/0141490 A1 | 7/2003 | Walters et al. |
| 2003/0165686 A1 | 9/2003 | Blackburn et al. |
| 2003/0180444 A1 | 9/2003 | Takekuma et al. |
| 2003/0236376 A1 | 12/2003 | Kindt-Larsen et al. |
| 2004/0185255 A1 | 9/2004 | Walters et al. |
| 2004/0185268 A1 | 9/2004 | Kumar et al. |
| 2004/0186241 A1 | 9/2004 | Gemert |
| 2004/0191520 A1 | 9/2004 | Kumar et al. |
| 2004/0197563 A1 | 10/2004 | Kye |
| 2005/0004361 A1 | 1/2005 | Kumar et al. |
| 2005/0175306 A1 | 8/2005 | Chong et al. |
| 2005/0258408 A1 | 11/2005 | Molock et al. |
| 2006/0022176 A1 | 2/2006 | Wang et al. |
| 2006/0090848 A1 | 5/2006 | Koga et al. |
| 2006/0100408 A1 | 5/2006 | Powell et al. |
| 2006/0110520 A1 | 5/2006 | Midorikawa et al. |
| 2006/0226400 A1 | 10/2006 | Xiao et al. |
| 2006/0226401 A1 | 10/2006 | Xiao et al. |
| 2006/0226402 A1 | 10/2006 | Kim et al. |
| 2006/0227287 A1 * | 10/2006 | Molock et al. ............... 351/163 |
| 2006/0228557 A1 | 10/2006 | Kim et al. |
| 2007/0001155 A1 | 1/2007 | Walters et al. |
| 2007/0249794 A1 | 10/2007 | Evans et al. |
| 2008/0103301 A1 | 5/2008 | Chopra et al. |
| 2009/0032782 A1 | 2/2009 | Kim et al. |
| 2011/0042629 A1 | 2/2011 | Chopra et al. |
| 2011/0108781 A1 | 5/2011 | Tomasulo |
| 2011/0143141 A1 | 6/2011 | He et al. |
| 2011/0190455 A1 | 8/2011 | Partington |
| 2011/0248415 A1 | 10/2011 | Alvarez-Carrigan et al. |
| 2011/0249235 A1 | 10/2011 | Duis et al. |
| 2012/0145973 A1 | 6/2012 | Bancroft et al. |
| 2012/0156508 A1 | 6/2012 | He et al. |

FOREIGN PATENT DOCUMENTS

| | | |
|---|---|---|
| EP | 1054010 A1 | 11/2000 |
| EP | 1184379 A1 | 6/2002 |
| JP | 2000327676 A | 11/2000 |
| JP | 2004131593 A | 4/2004 |
| WO | 9737254 A1 | 10/1997 |
| WO | 9740409 A1 | 10/1997 |
| WO | 9748762 A1 | 12/1997 |
| WO | 9748993 A1 | 12/1997 |
| WO | 9828289 A1 | 7/1998 |
| WO | 9915518 A1 | 4/1999 |
| WO | 9923071 A1 | 5/1999 |
| WO | 00/05325 A1 | 2/2000 |
| WO | 0015630 A1 | 3/2000 |
| WO | 0119813 A1 | 3/2001 |
| WO | 0160811 A1 | 8/2001 |
| WO | 0170719 A2 | 9/2001 |
| WO | 0194336 A1 | 12/2001 |
| WO | 03056390 A2 | 7/2003 |
| WO | 2004041961 A1 | 5/2004 |
| WO | 2005/005570 A1 | 1/2005 |
| WO | 2005105874 A1 | 11/2005 |
| WO | 2006022825 A1 | 3/2006 |
| WO | 2006/110219 A1 | 10/2006 |
| WO | 2006/110305 A1 | 10/2006 |
| WO | 2006110520 A1 | 10/2006 |
| WO | 2010/020770 A1 | 2/2010 |
| WO | 2011/053615 A1 | 5/2011 |
| WO | 2011053615 A1 | 5/2011 |
| WO | 2011/130137 A2 | 10/2011 |
| WO | 2011/130139 A1 | 10/2011 |
| WO | 2012/082999 | 6/2012 |

* cited by examiner

PHOTOCHROMIC MATERIALS THAT INCLUDE INDENO-FUSED NAPHTHOPYRANS

CROSS REFERENCE TO RELATED APPLICATIONS

This application is a continuation-in-part of U.S. patent application Ser. No. 12/873,735, filed on Sep. 1, 2010, which is a continuation in part of U.S. patent application Ser. No. 12/136,339, filed on Jun. 10, 2008, now abandoned, which is a divisional of U.S. patent application Ser. No. 11/102,279, filed on Apr. 8, 2005, now abandoned, the disclosure of each of which is incorporated herein by reference in its entirety.

FIELD

The present invention relates to photochromic materials that include one or more indeno-fused naphthopyrans having certain groups at the 7, 11 and 13 positions thereof, and at the position alpha to the pyran ring oxygen thereof, and to photochromic articles and compositions that include such indeno-fused naphthopyrans.

BACKGROUND

In response to certain wavelengths of electromagnetic radiation (or "actinic radiation"), photochromic compounds, such as indeno-fused naphthopyrans, typically undergo a transformation from one form or state to another form, with each form having a characteristic or distinguishable absorption spectrum associated therewith. Typically, upon exposure to actinic radiation, many photochromic compounds are transformed from a closed-form, which corresponds to an unactivated (or bleached, e.g., substantially colorless) state of the photochromic compound, to an open-form, which corresponds to an activated (or colored) state of the photochromic compound. In the absence of exposure to actinic radiation, such photochromic compounds are reversibly transformed from the activated (or colored) state, back to the unactivated (or bleached) state. Compositions and articles, such as eyewear lenses, that contain photochromic compounds or have photochromic compounds applied thereto (e.g., in form of a photochromic coating composition) typically display colorless (e.g., clear) and colored states that correspond to the colorless and colored states of the photochromic compounds contained therein or applied thereto.

After exposure to actinic radiation for an extended period of time, photochromic compounds can be prone to fatigue, which typically results in a decrease in colorability or optical density and a corresponding increase in yellowness of the photochromic compound when in the activated (or colored) state. The fatigue of a photochromic compound can be characterized as a function of time, which can be quantified as the fatigue rate for a particular photochromic compound. Typically, a lower fatigue rate is associated with an increased usable lifetime for a photochromic compound. Photochromic compounds can be expensive, and articles, such as ophthalmic lenses into which photochromic compounds are incorporated can correspondingly be more expensive than comparative articles that are free of photochromic compounds. As such, it is generally desirable to use photochromic compounds having low fatigue rates, so that the usable lifetime of an article, into which the photochromic compound is incorporated, can be increased or maximized.

It would be desirable to develop new photochromic materials that have desirably reduced fatigue rates. In addition, it would be desirable that such newly developed photochromic materials provide a desirable level of coloration or optical density when in an activated (or colored) state.

SUMMARY

In accordance with some embodiments of the present invention, there is provided photochromic material comprising an indeno-fused naphthopyran represented by at least one of the following Formula (I) and Formula (II),

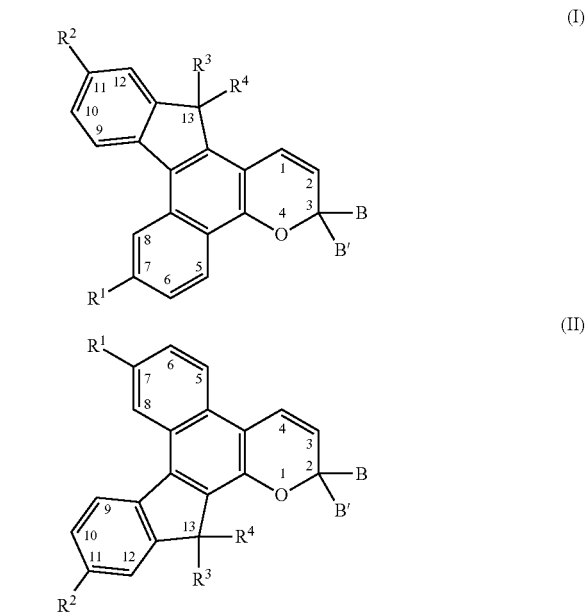

The $R^1$ group of Formula (I) and Formula (II) is in each case independently selected from, hydrogen, and $R_5O-$, wherein $R_5$ is selected from linear or branched $C_1$-$C_{20}$ alkyl, $C_3$-$C_{12}$ cycloalkyl, and $C_3$-$C_{12}$ heterocycloalkyl.

With some further embodiments, the $R^1$ group of Formula (I) and Formula (II) can in each case be independently and additionally selected from $-N(R_{11}')R_{12}'$, wherein $R_{11}'$ and $R_{12}'$ are each independently hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl or $C_1$-$C_{20}$ alkoxyalkyl, wherein said aryl group is phenyl or naphthyl, or $R_{11}'$ and $R_{12}'$ come together with the nitrogen atom to form a $C_3$-$C_{20}$ hetero-bicycloalkyl ring or a $C_4$-$C_{20}$ hetero-tricycloalkyl ring.

In accordance with some further embodiments, the $R^1$ group of Formula (I) and Formula (II) can in each case be independently and additionally selected from a nitrogen containing ring substituent represented by the following Formula (IIIA):

With reference to Formula (IIIA), each —Y— is independently chosen for each occurrence from —CH$_2$—, —CH(R$_{13}$')—, —C(R$_{13}$')$_2$—, —CH(aryl)-, —C(aryl)$_2$-, and —C(R$_{13}$')(aryl)-, and Z is —Y—, —O—, —S—, —S(O)—, —SO$_2$—, —NH—, —N(R$_{13}$')—, or —N(aryl)-, wherein each R$_{13}$' is independently C$_1$-C$_6$ alkyl, each aryl is independently phenyl or naphthyl, m is an integer 1, 2 or 3, and p is an integer 0, 1, 2, or 3 and provided that when p is 0, Z is —Y—.

In accordance with some further embodiments, the R$^1$ group of Formula (I) and Formula (II) can in each case be independently and additionally selected from a nitrogen containing ring substituent represented by Formula (IIIB) and/or Formula (IIIC):

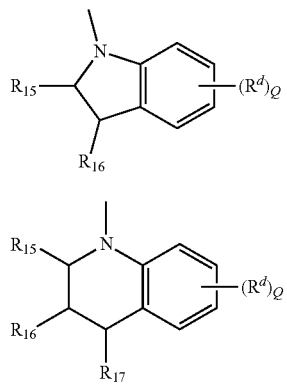

With reference to Formulas (IIIB) and (IIIC), R$_{15}$, R$_{16}$, and R$_{17}$ are each independently selected from hydrogen, C$_1$-C$_6$ alkyl, phenyl, or naphthyl, or the groups R$_{15}$ and R$_{16}$ together form a ring of 5 to 8 carbon atoms and each R$^d$ is independently for each occurrence selected from C$_1$-C$_6$ alkyl, C$_1$-C$_6$ alkoxy, fluoro or chloro, and Q is an integer 0, 1, 2, or 3.

With further reference to Formula (I) and (II), R$^2$ is in each case independently selected optionally substituted aryl, optionally substituted heteroaryl, and optionally substituted polycyclic-aryl-alkyl fused ring in which an aryl ring is directly bonded to Position-11. The optional aryl substituents, optional heteroaryl substituents, and optional polycyclic-aryl-alkyl fused ring substituents each being selected from hydroxyl, halo, carbonyl, C$_1$-C$_6$ alkoxycarbonyl, cyano, halo(C$_1$-C$_6$)alkyl, C$_1$-C$_6$ alkyl, C$_1$-C$_6$ alkoxy, —N(R$_{11}$')R$_{12}$' wherein R$_{11}$' and R$_{12}$' are each as described above, said nitrogen containing ring substituent represented by Formula (IIIA) wherein Formula (IIIA) is a described above, optionally substituted C$_3$-C$_{12}$ heterocyclalkyl, optionally substituted aryl, and optionally substituted heteroaryl.

With additional reference to Formulas (I) and (II), R$^3$ and R$^4$ are in each case independently selected from optionally substituted linear or branched C$_1$-C$_{20}$ alkyl, optionally substituted C$_3$-C$_{12}$ cycloalkyl, optionally substituted C$_3$-C$_{12}$ heterocycloalkyl, R$_5$'—OH where R$_5$' is selected from linear or branched C$_1$-C$_{20}$ alkyl and C$_3$-C$_{12}$ cycloalkyl, and —C(O)OR$_6$' where R$_6$' is selected from linear or branched C$_1$—O$_{20}$ alkyl and C$_3$-C$_{12}$ cycloalkyl. The optional substituents of the groups from which R$^3$ and R$^4$ can each be independently selected include, but are not limited to linear or branched C$_1$-C$_{20}$ alkyl, C$_3$-C$_{12}$ cycloalkyl, and C$_3$-C$_{12}$ heterocycloalkyl.

With additional further reference to Formulas (I) and (II), B and B' are in each case independently, an aryl group that is mono-substituted with a reactive substituent or a compatiblizing substituent; an unsubstituted aryl group; a mono-, di-, tri- or tetra-substituted aryl group; 9-julolidinyl; an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl and fluorenyl.

The aryl substituents and heteroaromatic substituents of the optionally substituted aryl and optionally substituted heteroaromatic groups from which B and B' can each be independently selected, are themselves each independently, hydroxy, halo, aryl, mono- or di-(C$_1$-C$_{12}$)alkoxyaryl, mono- or di-(C$_1$-C$_{12}$)alkylaryl, haloaryl, C$_3$-C$_7$ cycloalkylaryl, C$_3$-C$_7$ cycloalkyl, C$_3$-C$_7$ cycloalkyloxy, C$_3$-C$_7$ cycloalkyloxy(C$_1$-C$_{12}$)alkyl, cycloalkyloxy(C$_1$-C$_{12}$)alkoxy, aryl(C$_1$-C$_{12}$)alkyl, aryl(C$_1$-C$_{12}$)alkoxy, aryloxy, aryloxy(C$_1$-C$_{12}$)alkyl, aryloxy(C$_1$-C$_{12}$)alkoxy, mono- or di-(C$_1$-C$_{12}$)alkylaryl(C$_1$-C$_{12}$)alkyl, mono- or di-(C$_1$-C$_{12}$)alkoxyaryl(C$_1$-C$_{12}$)alkyl, mono- or di-(C$_1$-C$_{12}$)alkylaryl(C$_1$-C$_{12}$)alkoxy, mono- or di-(C$_1$-C$_{12}$)alkoxyaryl(C$_1$-C$_{12}$)alkoxy, amino, mono- or di-(C$_1$-C$_{12}$)alkylamino, diarylamino, piperazino, N—(C$_1$-C$_{12}$)alkylpiperazino, N-arylpiperazino, aziridino, indolino, piperidino, morpholino, thiomorpholino, tetrahydroquinolino, tetrahydroisoquinolino, pyrrolidyl, linear or branched C$_1$-C$_{12}$ alkyl, linear or branched C$_1$-C$_{12}$ haloalkyl, linear or branched C$_1$-C$_{12}$ alkoxy, mono(C$_1$-C$_{12}$)alkoxy(C$_1$-C$_{12}$)alkyl, acryloxy, methacryloxy, halogen, or —C(=O)R$^{21}$ wherein R$^{21}$ is —OR$^{22}$, —N(R$^{23}$)R$^{24}$, piperidino or morpholino, wherein R$^{22}$ is allyl, C$_1$-C$_6$ alkyl, phenyl, mono(C$_1$-C$_6$)alkyl substituted phenyl, mono(C$_1$-C$_6$)alkoxy substituted phenyl, phenyl(C$_1$-C$_3$)alkyl, mono(C$_1$-C$_6$)alkyl substituted phenyl(C$_1$-C$_3$)alkyl, mono(C$_1$-C$_6$)alkoxy substituted phenyl(C$_1$-C$_3$)alkyl, C$_1$-C$_6$ alkoxy(C$_2$-C$_4$)alkyl or C$_1$-C$_6$ haloalkyl, and R$^{23}$ and R$^{24}$ are each independently C$_1$-C$_6$ alkyl, C$_5$-C$_7$ cycloalkyl or a substituted or unsubstituted phenyl, said phenyl substituents independently being C$_1$-C$_6$ alkyl or C$_1$-C$_6$ alkoxy, or With further reference to Formulas (I) and (II), B and B' can in each case independently be an unsubstituted or mono-substituted group chosen from pyrazolyl, imidazolyl, pyrazolinyl, imidazolinyl, pyrrolinyl, phenothiazinyl, phenoxazinyl, phenazinyl and acridinyl, said substituents being C$_1$-C$_{12}$ alkyl, C$_1$-C$_{12}$ alkoxy, phenyl or halogen.

With additional reference to Formulas (I) and (II), B and B' can in each case independently be a mono-substituted phenyl, in which the phenyl has a substituent located at the para position, the substituent being a dicarboxylic acid residue or derivative thereof, a diamine residue or derivative thereof, an amino alcohol residue or derivative thereof, a polyol residue or derivative thereof, —(CH$_2$)—, —(CH$_2$)$_t$— or —[O—(CH$_2$)$_t$]$_k$—, wherein t ranges form 2 to 6 and k ranges from 1 to 50, and wherein the substituent is connected to an aryl group on another (or separate) photochromic material. The other (or separate) photochromic material can be selected from photochromic materials including, but not limited to, those photochromic compounds and materials as described further herein. With some embodiments, the other (or separate) photochromic material is selected from photochromic materials represented by Formula (I) or Formula (II). With some further embodiments, the other (or separate) photochromic material is selected from photochromic materials represented by Formula (I).

Additionally with reference to Formulas (I) and (II), B and B' can in each case independently be a group represented by the following Formula (IVA) and/or Formula

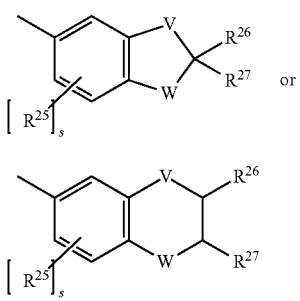 (IVA)

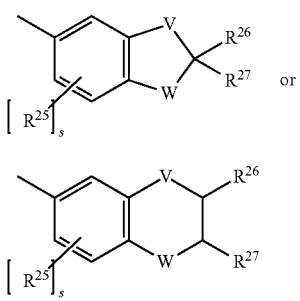 (IVB)

With reference to Formulas (IVA) and (IVB), V is —CH$_2$— or —O—, W is oxygen or substituted nitrogen, provided that when W is substituted nitrogen, V is —CH$_2$—, the substituted nitrogen substituents being hydrogen, C$_1$-C$_{12}$ alkyl or C$_1$-C$_{12}$ acyl, each R$^{25}$ independently being C$_1$-C$_{12}$ alkyl, C$_1$-C$_{12}$ alkoxy, hydroxy or halogen, R$^{26}$ and R$^{27}$ are each independently hydrogen or C$_1$-C$_{12}$ alkyl, and s ranges from 0 to 2.

With still further reference to Formulas (I) and (II), B and B' can in each case independently be a group represented by the following Formula (V):

$$\begin{array}{c}\diagdown\\R^{28}\end{array}C=C\begin{array}{c}H\\\diagup\\R^{29}\end{array}$$ (V)

With reference to Formula (V), R$^{28}$ is hydrogen or C$_1$-C$_{12}$ alkyl, and R$^{29}$ is an unsubstituted, mono- or di-substituted naphthyl, phenyl, furanyl or thienyl, said substituents being C$_1$-C$_{12}$ alkyl, C$_1$-C$_{12}$ alkoxy or halogen.

With further reference to Formulas (I) and (II), B and B' taken together can in each case independently form a fluoren-9-ylidene or mono- or di-substituted fluoren-9-ylidene, each of said fluoren-9-ylidene substituents independently being C$_1$-C$_{12}$ alkyl, C$_1$-C$_{12}$ alkoxy or halogen.

With additional further reference to Formulas (I) and (II), there is the proviso, with some embodiments, that R$^3$ and R$^4$ each are not selected from hydroxyl and R$_6$O—, where R$_6$ is selected from hydrocarbyl and heterohydrocarbyl (hydrocarbyl interrupted with one or more heteroatoms and/or combinations of two or more heteroatoms), including, but not limited to, optionally substituted alkyl, optionally substituted cycloalkyl, optionally substituted heterocycloalkyl, optionally substituted aryl, and optionally substituted heteroaryl.

DESCRIPTION

As used herein, the articles "a," "an," and "the" include plural referents unless otherwise expressly and unequivocally limited to one referent.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

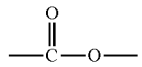

or equivalently —C(O)O—, is inclusive of the right-to-left representation thereof,

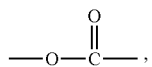

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about."

The photochromic materials and compounds of the present invention as described herein, including the ideno-fused naphthopyran compounds represented by Formula (I) and Formula (II), and related photochromic compounds, in each case optionally further include one or more coproducts, resulting from the synthesis of such photochromic compounds.

As used herein, the term "actinic radiation" means electromagnetic radiation that is capable of causing a response in a material, such as, but not limited to, transforming a photochromic material from one form or state to another as will be discussed in further detail herein.

As used herein, the term "photochromic" and similar terms, such as "photochromic compound" means having an absorption spectrum for at least visible radiation that varies in response to absorption of at least actinic radiation. Further, as used herein the term "photochromic material" means any substance that is adapted to display photochromic properties (such as, adapted to have an absorption spectrum for at least visible radiation that varies in response to absorption of at least actinic radiation) and which includes at least one photochromic compound.

As used herein, the term "photochromic compound" includes indeno-fused naphthopyran compounds, including but not limited to those represented by Formula (I) and/or Formula (II).

As used herein, the term "photochromic compound" includes thermally reversible photochromic compounds and non-thermally reversible photochromic compounds. The term "thermally reversible photochromic compounds/materials" as used herein means compounds/materials capable of converting from a first state, for example a "clear state," to a second state, for example a "colored state," in response to actinic radiation, and reverting back to the first state in response to thermal energy. The term "non-thermally reversible photochromic compounds/materials" as used herein means compounds/materials capable of converting from a first state, for example a "clear state," to a second state, for example a "colored state," in response to actinic radiation, and reverting back to the first state in response to actinic radiation of substantially the same wavelength(s) as the absorption(s) of the colored state (e.g., discontinuing exposure to such actinic radiation).

As used herein to modify the term "state," the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, according to various non-limiting embodiments disclosed herein, the photochromic compounds of the present invention can have a different absorption spectrum in each of the first and second state. For example, while not limiting herein, a photochromic compound of the present invention can be clear in the first state and colored in the second state. Alternatively, a photochromic compound of the present invention can have a first color in the first state and a second color in the second state.

As used herein the term "optical" means pertaining to or associated with light and/or vision. For example, according to various non-limiting embodiments disclosed herein, the optical article or element or device can be chosen from ophthalmic articles, elements and devices, display articles, elements and devices, windows, mirrors, and active and passive liquid crystal cell articles, elements and devices.

As used herein the term "ophthalmic" means pertaining to or associated with the eye and vision. Non-limiting examples of ophthalmic articles or elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

As used herein the term "ophthalmic substrate" means lenses, partially formed lenses, and lens blanks.

As used herein the term "display" means the visible or machine-readable representation of information in words, numbers, symbols, designs or drawings. Non-limiting examples of display articles, elements and devices include screens, monitors, and security elements, such as security marks.

As used herein the term "window" means an aperture adapted to permit the transmission of radiation therethrough. Non-limiting examples of windows include automotive and aircraft transparencies, filters, shutters, and optical switches.

As used herein the term "mirror" means a surface that specularly reflects a large or substantial fraction of incident light.

As used herein the term "liquid crystal cell" refers to a structure containing a liquid crystal material that is capable of being ordered. Active liquid crystal cells are cells in which the liquid crystal material is capable of being reversibly and controllably switched or converted between ordered and disordered states, or between two ordered states by the application of an external force, such as electric or magnetic fields. Passive liquid crystal cells are cells in which the liquid crystal material maintains an ordered state. A non-limiting example of an active liquid crystal cell element or device is a liquid crystal display.

As used herein the term "coating" means a supported film derived from a flowable composition, which can or can not have a uniform thickness, and specifically excludes polymeric sheets. A layer that includes one or more photochromic compounds of the present invention can, with some embodiments, be a photochromic coating.

As used herein the term "sheet" means a pre-formed film having a generally uniform thickness and capable of self-support.

As used herein the term "connected to" means in direct contact with an object or indirect contact with an object through one or more other structures or materials, at least one of which is in direct contact with the object. For purposes of non-limiting illustration, a coating containing one or more photochromic compounds of the present invention, for example, can be in direct contact (e.g., abutting contact) with at least a portion of a substrate, such as an optical article, or it can be in indirect contact with at least a portion of the substrate through one or more other interposed structures or materials, such as a monomolecular layer of a coupling or adhesive agent. For example, although not limiting herein, a coating containing one or more photochromic compounds of the present invention, can be in contact with one or more other interposed coatings, polymer sheets or combinations thereof, at least one of which is in direct contact with at least a portion of the substrate.

As used herein, the term "photosensitive material" means materials that physically or chemically respond to electromagnetic radiation, including, but not limited to, phosphorescent materials and fluorescent materials.

As used herein, the term "non-photosensitive materials" means materials that do not physically or chemically respond to electromagnetic radiation, including, but not limited to, static dyes.

As used herein, molecular weight values of polymers, such as weight average molecular weights (Mw) and number average molecular weights (Mn), are determined by gel permeation chromatography using appropriate standards, such as polystyrene standards.

As used herein, polydispersity index (PDI) values represent a ratio of the weight average molecular weight (Mw) to the number average molecular weight (Mn) of the polymer (i.e., Mw/Mn).

As used herein, the term "polymer" means homopolymers (e.g., prepared from a single monomer species), copolymers (e.g., prepared from at least two monomer species), and graft polymers.

As used herein, the term "(meth)acrylate" and similar terms, such as "(meth)acrylic acid ester" means methacrylates and/or acrylates. As used herein, the term "(meth)acrylic acid" means methacrylic acid and/or acrylic acid.

Other than in the operating examples, or where otherwise indicated, all numbers expressing quantities of ingredients, reaction conditions, and so forth used in the specification and claims are to be understood as modified in all instances by the term "about."

As used herein, spatial or directional terms, such as "left", "right", "inner", "outer", "above", "below", and the like, relate to the invention as it is depicted in the drawing figures. However, it is to be understood that the invention can assume various alternative orientations and, accordingly, such terms are not to be considered as limiting.

As used herein, the terms "formed over," "deposited over," "provided over," "applied over," "residing over," or "positioned over," mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

All documents, such as but not limited to issued patents and patent applications, referred to herein, and unless otherwise indicated, are to be considered to be "incorporated by reference" in their entirety.

As used herein, recitations of "linear or branched" groups, such as linear or branched alkyl, are herein understood to include: a methylene group or a methyl group; groups that are linear, such as linear $C_2$-$C_{20}$ alkyl groups; and groups that are appropriately branched, such as branched $C_3$-$C_{20}$ alkyl groups.

As used herein, recitations of "optionally substituted" group, means a group, including but not limited to, alkyl group, cycloalkyl group, heterocycloalkyl group, aryl group, and/or heteroaryl group, in which at least one hydrogen thereof has been optionally replaced or substituted with a group that is other than hydrogen, such as, but not limited to, halo groups (e.g., F, Cl, I, and Br), hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (including, but not limited to: alkyl; alkenyl; alkynyl; cycloalkyl, including poly-fused-ring cycloalkyl and polycyclocalkyl; heterocycloalkyl; aryl, including hydroxyl substituted aryl, such as phenol, and including poly-fused-ring aryl; heteroaryl, including poly-fused-ring heteroaryl; and aralkyl groups), and amine groups, such as —N($R^{11}$)($R^{12}$)) where $R^{11}$ and $R^{12}$ are each independently selected from hydrogen, linear or branched $C_1$-$C_{20}$ alkyl, $C_3$-$C_{12}$ cycloakyl, $C_3$-$C_{12}$ heterocycloalkyl, aryl, and heteroaryl.

As used herein, and unless otherwise indicated, recitations of "halo substituted" and related terms (such as, but not limited to, haloalkyl groups, haloalkenyl groups, haloalkynyl groups, haloaryl groups and halo-heteroaryl groups) means a group in which at least one, and up to and including all of the available hydrogen groups thereof is substituted with a halo group. The term "halo-substituted" is inclusive of "perhalo-substituted." As used herein, the term perhalo-substituted group and related terms (such as, but not limited to perhaloalkyl groups, perhaloalkenyl groups, perhaloalkynyl groups, perhaloaryl groups and perhalo-heteroaryl groups) means a group in which all of the available hydrogen groups thereof is substituted with a halo group. For example, perhalomethyl is —$CX_3$; perhalophenyl is —$C_6X_5$, where X represents one or more halo groups (e.g., F).

As used herein, the term "alkyl" means linear or branched $C_1$-$C_{20}$ alkyl, such as, but not limited to linear or branched $C_1$-$C_{10}$ alkyl or linear or branched $C_2$-$C_{10}$ alkyl. Examples of alkyl groups from which the various alkyl groups of the present invention can be selected from, include, but are not limited to, methyl, ethyl, propyl, isopropyl, butyl, isobutyl, sec-butyl, tert-butyl, pentyl, neopentyl, hexyl, heptyl, octyl, nonyl and decyl. Alkyl groups of the various compounds of the present invention can, with some embodiments, include one or more unsaturated linkages selected from —CH=CH— groups and/or one or more —C≡C— groups, provided the alkyl group is free of two or more conjugated unsaturated linkages. With some embodiments, the alkyl groups are free of unsaturated linkages, such as —CH=CH— groups and —C≡C— groups.

As used herein, the term "cycloalkl" means groups that are appropriately cyclic, such as $C_3$-$C_{12}$ cycloalkyl (including, but not limited to, cyclic $C_5$-$C_7$ alkyl) groups. Examples of cycloalkyl groups include, but are not limited to, cyclopropyl, cyclobutyl, cyclopentyl, cyclohexyl, and cyclooctyl. The term "cycloalkyl" as used herein also includes: bridged ring polycycloalkyl groups (or bridged ring polycyclic alkyl groups), such as but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

As used herein, the term "heterocycloalkyl" means groups that are appropriately cyclic, such as $C_3$-$C_{12}$ heterocycloalkyl groups or $C_5$-$C_7$ heterocycloalkyl groups, and which have at least one hetero atom in the cyclic ring, such as, but not limited to, O, S, N, P, and combinations thereof. Examples of heterocycloalkyl groups include, but are not limited to, imidazolyl, tetrahydrofuranyl, tetrahydropyranyl and piperidinyl. The term "heterocycloalkyl" as used herein also includes: bridged ring polycyclic heterocycloalkyl groups, such as but not limited to, 7-oxabicyclo[2.2.1]heptanyl; and fused ring polycyclic heterocycloalkyl groups, such as but not limited to, octahydrocyclopenta[b]pyranyl, and octahydro-1H-isochromenyl.

As used herein, the term "aryl" includes, but is not limited to, $C_5$-$C_{18}$ aryl, such as but not limited to, $C_5$-$C_{10}$ aryl (including fused ring polycyclic aryl groups). Examples of aryl groups include, but are not limited to, phenyl, naphthyl, and anthracenyl.

As used herein, the term "heteroaryl," includes but is not limited to $C_5$-$C_{18}$ heteroaryl, such as but not limited to $C_5$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group. Examples of heteroaryl groups include, but are not limited to, furanyl, pyranyl, pyridinyl, isoquinoline, and pyrimidinyl.

As used herein, the term "fused ring polycyclic-aryl-alkyl group" and similar terms such as, fused ring polycyclic-alkyl-aryl group, fused ring polycyclo-aryl-alkyl group, and fused ring polycyclo-alkyl-aryl group means a fused ring polycyclic group that includes at least one aryl ring and at least one cycloalkyl ring that are fused together to form a fused ring structure. For purposes of non-limiting illustration, examples of fused ring polycyclic-aryl-alkyl groups include, but are not limited to indenyl, 9H-flourenyl, cyclopentanaphthenyl, and indacenyl.

As used herein, the term "aralkyl," includes but is not limited to $C_6$-$C_{24}$ aralkyl, such as but not limited to $C_6$-$C_{10}$ aralkyl, means an aryl group substituted with an alkyl group that is bonded (or linked) to another group. Examples of aralkyl groups include, but are not limited to, benzyl, and phenethyl.

As used herein the term "hydrocarbyl" and similar terms, such as "hydrocarbyl substituent," means: linear or branched $C_1$-$C_{20}$ alkyl (e.g., linear or branched $C_1$-$C_{10}$ alkyl); linear or branched $C_2$-$C_{20}$ alkenyl (e.g., linear or branched $C_2$-$C_{10}$ alkenyl); linear or branched $C_2$-$C_{20}$ alkynyl (e.g., linear or branched $C_2$-$C_{10}$ alkynyl); $C_3$-$C_{12}$ cycloalkyl (e.g., $C_3$-$C_{10}$ cycloalkyl); $C_5$-$C_{18}$ aryl (including polycyclic aryl groups) (e.g., $C_5$-$C_{10}$ aryl); and $C_6$-$C_{24}$ aralkyl (e.g., $C_6$-$C_{10}$ aralkyl). As used herein the term "hydrocarbyl" is inclusive of "heterohydrocarbyl," which is a hydrocarbyl in which at least one carbon, but less than all of the carbons thereof, has been replaced with a heteroatom, such as, but not limited to, O, N, S, and combinations thereof. Examples of heterohydrocarbyls from which a hydrocarbyl can be selected include, but are not limited to: $C_3$-$C_{12}$ heterocycloalkyl (having at least one hetero atom in the cyclic ring); and $C_5$-$C_{18}$ heteroaryl (having at least one hetero atom in the aromatic ring).

Representative alkyl groups include but are not limited to methyl, ethyl, propyl, isopropyl, butyl, isobutyl, sec-butyl, tert-butyl, pentyl, neopentyl, hexyl, heptyl, octyl, nonyl and decyl. Representative alkenyl groups include but are not limited to vinyl, allyl and propenyl. Representative alkynyl groups include but are not limited to ethynyl, 1-propynyl, 2-propynyl, 1-butynyl, and 2-butynyl. Representative cycloalkyl groups include but are not limited to cyclopropyl, cyclobutyl, cyclopentyl, cyclohexyl, and cyclooctyl substituents. Representative heterocycloalkyl groups include but are not limited to tetrahydrofuranyl, tetrahydropyranyl and piperidinyl, including but not limited to piperindin-4-yl. Representative aryl groups include but are not limited to phenyl, naphthyl, anthracenyl, phenantreneyl and triptycenyl. Representative heteroaryl groups include but are not limited to furanyl, pyranyl and pyridinyl. Representative aralkyl groups include but are not limited to benzyl, and phenethyl.

The term "substituted hydrocarbyl" as used herein means a hydrocarbyl group in which at least one hydrogen thereof has been replaced or substituted with a group that is other than hydrogen, such as, but not limited to, halo groups, hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (e.g., alkyl; alkenyl; alkynyl; cycloalkyl; heterocycloalkyl, such as piperidinyl, including but not limited to piperidin-4-yl, optionally substituted with, for example, at least one linear or branched $C_1$-$C_{10}$ alkyl group; aryl, including hydroxyl substituted aryl, such as phenol, optionally substituted with, for example, at least one linear or branched $C_1$-$C_{10}$ alkyl group; heteroaryl; and aralkyl groups), and amine groups, such as —N($R_{11}$')($R_{12}$') where $R_{11}$' and $R_{12}$' are each independently selected from hydrogen, hydrocarbyl and substituted hydrocarbyl.

For purposes of non-limiting illustration, the hydrocarbyl, of a substituted hydrocarbyl, can be selected from one or more of the hydrocarbyl groups described previously herein, such as a $C_3$-$C_{12}$ heterocycloalkyl group, such as piperidinyl, which can be substituted with one or more of the substituting groups described previously herein, such as one or more linear or branched $C_1$-$C_{25}$ alkyl groups. For purposes of further non-limiting illustration, the hydrocarbyl, of a substituted hydrocarbyl, can be selected from one or more of the hydrocarbyl groups described previously herein, such as an aryl group, such as phenyl, which can be substituted with one or more of the substituting groups described previously herein, such as one or more hydroxyl groups and/or one or more linear or branched $C_1$-$C_{25}$ alkyl groups.

The term "substituted hydrocarbyl" is inclusive of halohydrocarbyl (or halo substituted hydrocarbyl) substituents. The term "halohydrocarbyl" as used herein, and similar terms, such as halo substituted hydrocarbyl, means that at least one hydrogen atom of the hydrocarbyl (e.g., of the alkyl, alkenyl, alkynyl, cycloalkyl, heterocycloalkyl, aryl, heteroaryl, and aralkyl groups) is replaced with a halogen atom selected from chlorine, bromine, fluorine and iodine. The degree of halogenation can range from at least one hydrogen atom but less than all hydrogen atoms being replaced by a halogen atom (e.g., a fluoromethyl group), to full halogenation (perhalogenation) in which all replaceable hydrogen atoms on the hydrocarbyl group have each been replaced by a halogen atom (e.g., trifluoromethyl or perfluoromethyl). Correspondingly, the term "perhalohydrocarbyl group" as used herein means a hydrocarbyl group in which all replaceable hydrogens have been replaced with a halogen. Examples of perhalohydrocarbyl groups include, but are not limited to, perhalogenated phenyl groups and perhalogenated alkyl groups.

The hydrocarbyl and substituted hydrocarbyl groups from which the various groups described herein can each be independently selected, can in each case be independently and optionally interrupted with at least one of —O—, —S—, —C(O)—, —C(O)O—, —OC(O)O—, —S(O)—, —SO$_2$—, —N($R^9$)— and —Si($R^9$)($R^{10}$)—. As used herein, by interrupted with at least one of —O—, —S—, —C(O)—, —C(O)O—, —OC(O)O—, —S(O)—, —SO$_2$—, —N($R^9$)—, and —Si($R^9$)($R^{10}$)—, means that at least one carbon of, but less than all of the carbons of, the hydrocarbyl group or substituted hydrocarbyl group, is in each case independently replaced with one of the recited divalent non-carbon linking groups. The hydrocarbyl and substituted hydrocarbyl groups can be interrupted with two or more of the above recited linking groups, which can be adjacent to each other or separated by one or more carbons. For purposes of non-limiting illustration, a combination of adjacent —C(O)— and —N($R^9$)— can provide a divalent amide linking or interrupting group, —C(O)—N($R^9$)—. For purposes of further non-limiting illustration, a combination of adjacent —N($R^9$)—, —C(O)— and —O— can provide a divalent carbamate (or urethane) linking or interrupting group, —N($R^9$)—C(O)—O—, where $R^9$ is hydrogen. The $R^9$ and $R^{13}$ groups, of the previously recited interrupting groups, can each be independently selected from hydrocarbyl and heterohydrocarbyl groups.

The indeno-fused naphthopyran compounds of the present invention can be referred to herein with regard to various groups at (or bonded to) various positions of the indeno-fused naphthopyran compounds. The positions are referred to herein with regard to the ring-positions as enumerated in Formula (I) and Formula (II). With reference to Formula (I), $R^1$ is at the 7-position (or position 7), $R^2$ is at the 11-position (or position 11), $R^3$ and $R^4$ are each at the 13-position (or position 13), and B and B' are each at the 3-position (or position 3) of the indeno-fused naphthopyran represented by Formula (I). With reference to Formula (II), $R^1$ is at the 7-position (or position 7), $R^2$ is at the 11-position (or position 11), $R^3$ and $R^4$ are each at the 13-position (or position 13), and B and B' are each at the 2-position (or position 2) of the indeno-fused naphthopyran represented by Formula (II).

The photochromic materials and indeno-fused naphthopyran compounds of the present invention, and compositions containing such photochromic materials and/or indeno-fused naphthopyran compounds, will be described in further detail as follows.

With some embodiments of the present invention, the photochromic material includes one or more indeno-fused naphthopyrans represented by Formula (I). In accordance with some further embodiments, the photochromic material includes one or more indeno-fused naphthopyrans represented by Formula (I), and is free of one or more indeno-fused naphthopyrans represented by Formula (II).

With further reference to Formulas (I) and (II), $R^1$ can, with some embodiments, be selected from: hydrogen; $R_5$O—, wherein $R_5$ is selected from linear or branched $C_1$-$C_{20}$ alkyl; and the nitrogen containing ring substituent represented by general Formula (IIIA), in which each —Y— is independently chosen for each occurrence from —CH$_2$—, —CH($R_{13}$')—, and —C($R_{13}$')$_2$—, and Z is —Y—, or —O—, wherein each $R_{13}$' is independently linear or branched $C_1$-$C_6$ alkyl, m is an integer 1, 2 or 3, and p is an integer 0, 1, 2, or 3, and provided that when p is 0, Z is —Y—.

In accordance with some additional embodiments, $R^1$ of Formulas (I) and (II) can in each case be independently selected from: hydrogen; $R_5$O—, in which $R_5$ is selected from linear or branched $C_1$-$C_6$ alkyl, such as, but not limited to, methyl, ethyl, n-propyl, iso-propyl, n-butyl, various structural isomers of iso-butyl such as tert-butyl, n-pentyl, various structural isomers of iso-pentyl, n-hexyl, and various structural isomers of iso-hexyl; and the nitrogen containing ring substituent represented by Formula (III), in which the nitrogen containing ring substituent represented by Formula (III) is selected from piperidino

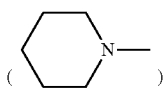

and morpholino

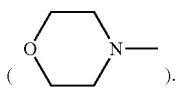

With further reference to Formula (I) and (II), and in accordance with some embodiments, $R^2$ is selected from optionally substituted phenyl, in which the optional phenyl substituents are selected from halo (F, Cl, Br and/or I), cyano, linear or branched halo($C_1$-$C_6$)alkyl (including linear or branched perhalo($C_1$-$C_6$)alkyl), linear or branched $C_1$-$C_6$ alkyl, linear or branched $C_1$-$C_6$ alkoxy, and amine groups selected from —N($R_{11}'$)($R_{12}'$), in which $R_{11}'$ and $R_{12}'$ are each independently selected from linear or branched $C_1$-$C_6$ alkyl.

In accordance with some further embodiments, $R^2$ is selected from optionally substituted fused ring polycyclic-aryl-alkyl groups in which an aryl ring of the fused ring polycyclic-aryl-alkyl group is directly bonded to Position-11 of the indeno-fused naphthopyran. Examples of fused ring polycyclic-aryl-alkyl groups from which $R^2$ can be selected, in accordance with some embodiments, include, but are not limited to, indenyl, 9H-flourenyl, cyclopentanaphthenyl, and indacenyl. With some embodiments, the fused ring polycyclic-aryl-alkyl groups from which $R^2$ can be selected include, but are not limited to, 9H-flouren-1-yl, 9H-flouren-2-yl, 9H-flouren-3-yl, and 9H-flouren-4-yl, each optionally substituted at the 9-position of the 9H-flourenyl ring with one or two groups each independently selected from linear or branched $C_1$-$C_{20}$ alkyl, and $C_3$-$C_{12}$ cycloalkyl.

In accordance with additional embodiments, $R^2$ of Formulas (I) and (II) is in each case independently selected from optionally substituted phenyl, in which the optional phenyl substituents are selected from halo (F, Cl, Br and/or I), linear or branched halo($C_1$-$C_6$)alkyl (including linear or branched perhalo($C_1$-$C_6$)alkyl), and linear or branched $C_1$-$C_6$ alkyl.

In accordance with further additional embodiments, $R^2$ of Formulas (I) and (II) is in each case independently selected from optionally substituted phenyl, where the optional substitutents are selected from optionally substituted $C_3$-$C_{12}$ heterocycloalkyl. Examples of heterocycloalkyl groups include, but are not limited to, imidazolyl, tetrahydrofuanyl, tetrahydropyanyl, and piperidinyl. The optional substituents of the heterocycloalkyl groups can be selected from, with some embodiments, linear of branched $C_1$-$C_{20}$ alkyl, $C_3$-$C_{12}$ cycloalkyl, $C_3$-$C_{12}$ heterocycloalkyl, aryl, and heteroaryl. With some embodiments, the optional $C_3$-$C_{12}$ heterocycloalkyl substituents of the phenyl group, from which $R^2$ can be selected, are selected from imidazol-2-yl, and the optional substituents of the imidazol-2-yl include those previously recited groups, such as phenyl. In accordance with some embodiments, R2 is selected from phenyl substituted with 1H-imidazol-2-yl, in which the 1H-imidazol-2-Y1 is optionally substituted with at least one phenyl group, such as, but not limited to, 4,5-diphenyl-1H-imidazol-2-yl.

With further reference to Formula (I) and (II), and in accordance with some embodiments, $R^3$ and $R^4$ are each independently selected from linear or branched $C_1$-$C_{20}$ alkyl.

With some additional embodiments, $R^3$ and $R^4$ of Formulas (I) and (II) are in each case independently selected from linear or branched $C_1$-$C_6$ alkyl, such as but not limited to, methyl, ethyl, n-propyl, iso-propyl, n-butyl, various structural isomers of iso-butyl such as tert-butyl, n-pentyl, various structural isomers of iso-pentyl, n-hexyl, and various structural isomers of iso-hexyl.

With additional reference to Formulas (I) and (II), and in accordance with some embodiments, B and B' are in each case independently an unsubstituted phenyl group, or a mono-substituted phenyl group, di-substituted phenyl group, a tri-substituted phenyl group, or a tetra-substituted phenyl group. The phenyl substituents, of the mono-, di-, tri- or tetra-substituted phenyl group, with some embodiments, are each independently selected from fluoro, linear or branched $C_1$-$C_{12}$ alkyl, linear or branched $C_1$-$C_{12}$ haloalkyl, linear or branched $C_1$-$C_{12}$ alkoxy, piperidino, and morpholino. In accordance with some further embodiments, B and B' of Formulas (I) and (II) are in each case independently an unsubstituted phenyl group, or a mono-substituted phenyl group, di-substituted phenyl group, a tri-substituted phenyl group, or a tetra-substituted phenyl group. The phenyl substituents, of the mono-, di-, tri- or tetra-substituted phenyl group, with some embodiments, are each selected from fluoro, linear or branched $C_1$-$C_6$ alkyl, linear or branched $C_1$-$C_6$ alkoxy, piperidino, and morpholino.

For purposes of non-limiting illustration, examples of indeno-fused naphthopyran compounds represented by Formula (I) include, but are not limited to, the following indeno-fused naphthopyran compounds (a) through (bb), in which representative names and structural formulas are provided.

In accordance with some embodiments, a non-limiting example of an indeno-fused naphthopyran represented by Formula (I) includes, but is not limited to, (a) 3-(4-butoxyphenyl)-3-(4-methoxyphenyl)-11-phenyl-13,13-dimethyl-3H,13H-indeno[2',3':3,4]naphtho[1,2-b]pyran, which is represented by the following Formula (a),

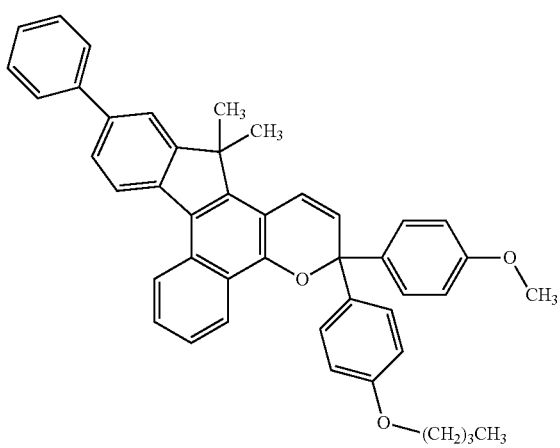

With reference to Formula (I) and Formula (a), $R^1$ is hydrogen, $R^2$ is phenyl, $R^3$ and $R^4$ are each methyl, B is 4-methoxyphenyl, and B' is 4-butoxyphenyl.

In accordance with some embodiments, a non-limiting example of an indeno-fused naphthopyran represented by Formula (I) includes, but is not limited to, (b) 3,3-bis-(4-methoxyphenyl)-1'-phenyl-13,13-dimethyl-3H,13H-indeno[2',3':3,4]naphtho[1,2-b]pyran, which is represented by the following Formula (b),

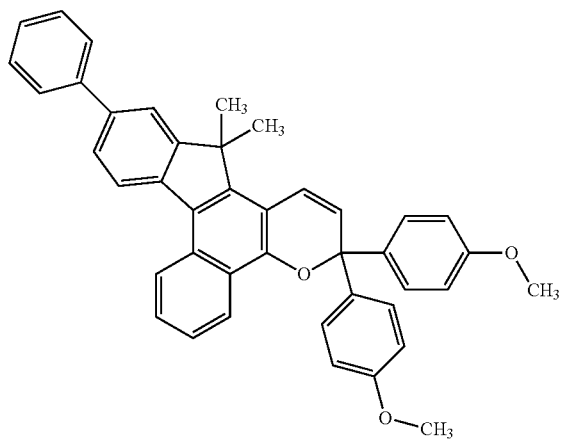

(b)

With reference to Formula (I) and Formula (b), $R^1$ is hydrogen, $R^2$ is phenyl, $R^3$ and $R^4$ are each methyl, and B and B' are each 4-methoxyphenyl.

In accordance with some embodiments, a non-limiting example of an indeno-fused naphthopyran represented by Formula (I) includes, but is not limited to, (c) 3-(4-butoxyphenyl)-3-(4-methoxyphenyl)-7-methoxy-11-phenyl-13,13-dimethyl-3H,13H-indeno[2',3':3,4]naphtho[1,2-b]pyran, which is represented by the following Formula (c),

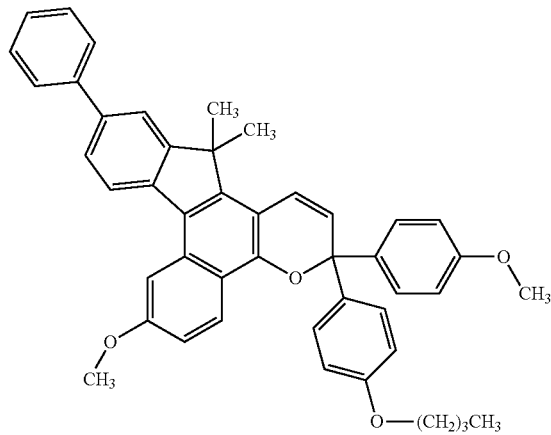

(c)

With reference to Formula (I) and Formula (c), $R^1$ is methoxy (—O—$CH_3$), $R^2$ is phenyl, $R^3$ and $R^4$ are each methyl, B is 4-methoxyphenyl, and B' is 4-butoxyphenyl.

In accordance with some embodiments, a non-limiting example of an indeno-fused naphthopyran represented by Formula (I) includes, but is not limited to, (d) 3,3-bis(4-methoxyphenyl)-7-methoxy-1'-phenyl-13,13-dimethyl-3H,13H-indeno[2',3':3,4]naphtho[1,2-b]pyran, which is represented by the following Formula (d),

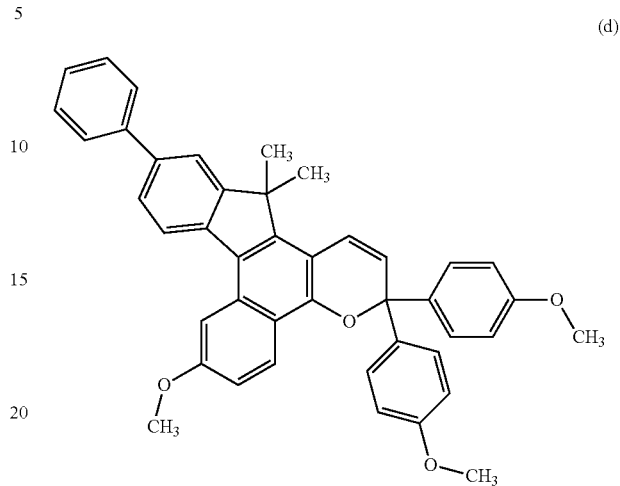

(d)

With reference to Formula (I) and Formula (d), $R^1$ is methoxy (—O—$CH_3$), $R^2$ is phenyl, $R^3$ and $R^4$ are each methyl, and B and B' are each 4-methoxyphenyl.

In accordance with some embodiments, a non-limiting example of an indeno-fused naphthopyran represented by Formula (I) includes, but is not limited to, (e) 3-(4-butoxyphenyl)-3-(4-methoxyphenyl)-7-morpholino-1'-phenyl-13,13-dimethyl-3H,13H-indeno[2',3':3,4]naphtho[1,2-b]pyran, which is represented by the following Formula (e),

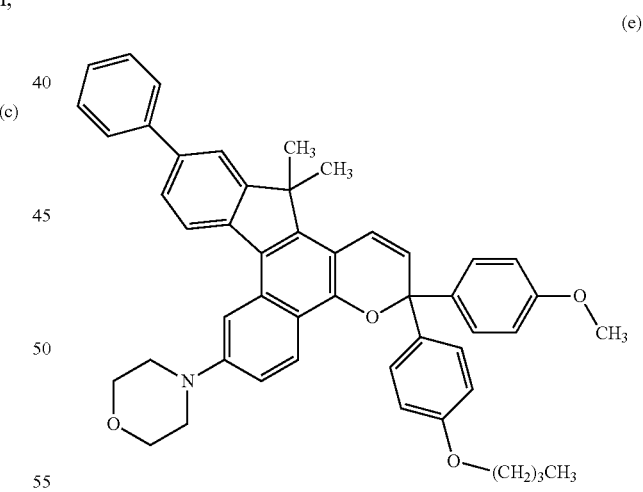

(e)

With reference to Formula (I) and Formula (e), $R^1$ is morpholino, $R^2$ is phenyl, $R^3$ and $R^4$ are each methyl, B is 4-methoxyphenyl, and B' is 4-butoxyphenyl.

In accordance with some embodiments, a non-limiting example of an indeno-fused naphthopyran represented by Formula (I) includes, but is not limited to, (f) 3,3-bis(4-methoxyphenyl)-7-morpholino-1'-phenyl-13,13-dimethyl-3H,13H-indeno[2',3':3,4]naphtho[1,2-b]pyran, which is represented by the following Formula (f),

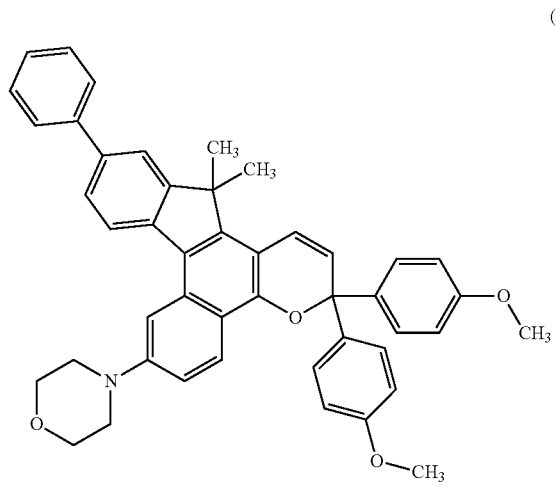
(f)

With reference to Formula (I) and Formula (f), $R^1$ is morpholino, $R^2$ is phenyl, $R^3$ and $R^4$ are each methyl, and B and B' are each 4-methoxyphenyl.

In accordance with some embodiments, a non-limiting example of an indeno-fused naphthopyran represented by Formula (I) includes, but is not limited to, (g) 3,3-bis(4-hydroxyphenyl)-7-methoxy-11-phenyl-13,13-diethyl-3H,13H-indeno[2',3':3,4]naphtho[1,2-b]pyran, which is represented by the following Formula (g),

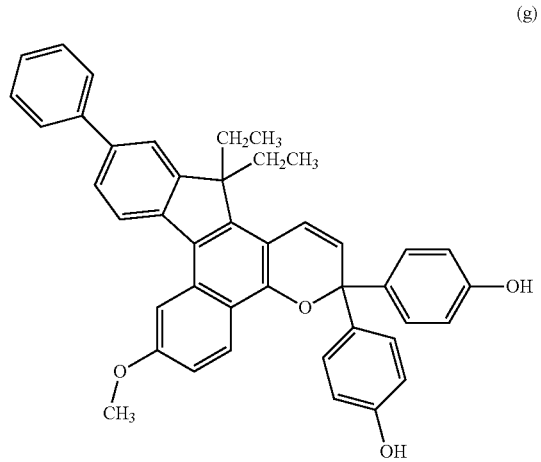 [SMILES: CCC1(CC)c2cc(-c3ccccc3)ccc2-c2c1c1c(c3ccc(OC)cc23)OC(c2ccc(O)cc2)(c2ccc(O)cc2)C=C1]
(g)

With reference to Formula (I) and Formula (g), $R^1$ is methoxy, $R^2$ is phenyl, $R^3$ and $R^4$ are each ethyl, and B and B' are each 4-hydroxyphenyl.

In accordance with some embodiments, a non-limiting example of an indeno-fused naphthopyran represented by Formula (I) includes, but is not limited to, (h) 3-(4-butoxyphenyl)-3-(4-methoxyphenyl)-7-methoxy-1'-phenyl-13,13-dipropyl-3H,13H-indeno[2',3':3,4]naphtho[1,2-b]pyran, which is represented by the following Formula (h),

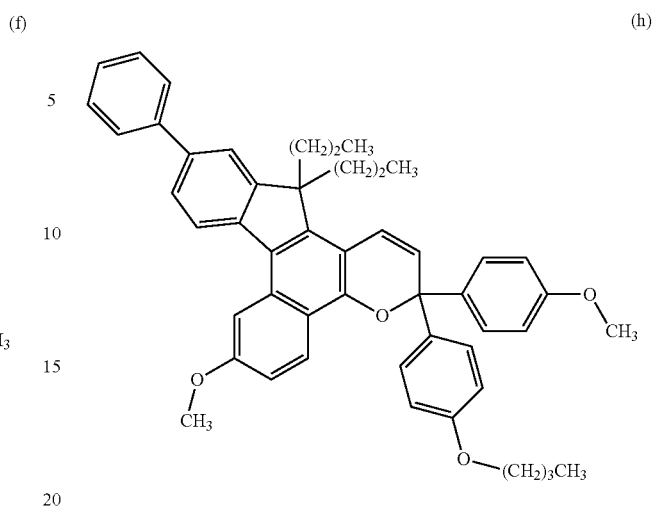
(h)

With reference to Formula (I) and Formula (h), $R^1$ is methoxy, $R^2$ is phenyl, $R^3$ and $R^4$ are each propyl, and B is 4-methoxyphenyl and B' are each 4-butoxyphenyl.

In accordance with some embodiments, a non-limiting example of an indeno-fused naphthopyran represented by Formula (I) includes, but is not limited to, (i) 3-(4-butoxyphenyl)-3-(4-methoxyphenyl)-7-methoxy-11-(2,4-dimethoxyphenyl)-13,13-dipropyl-3H,13H-indeno[2',3':3,4]naphtho[1,2-b]pyran, which is represented by the following Formula (I),

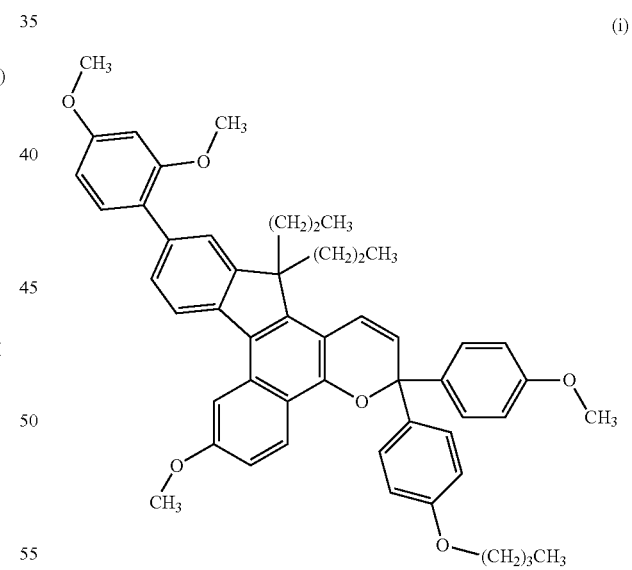
(i)

With reference to Formula (I) and Formula (h), $R^1$ is methoxy, $R^2$ is 2,4-dimethoxyphenyl, $R^3$ and $R^4$ are each propyl, B is 4-methoxyphenyl, and B' is 4-butoxyphenyl.

In accordance with some embodiments, a non-limiting example of an indeno-fused naphthopyran represented by Formula (I) includes, but is not limited to, (j) 3,3-bis(4-hydroxyphenyl)-7-methoxy-11-phenyl-13,13-dipropyl-3H,13H-indeno[2',3':3,4]naphtho[1,2-b]pyran, which is represented by the following Formula (j),

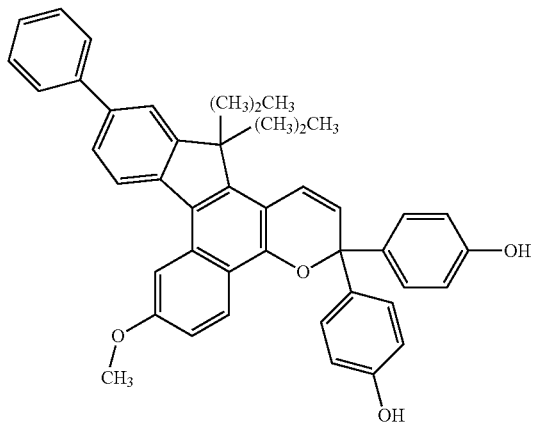

(j)

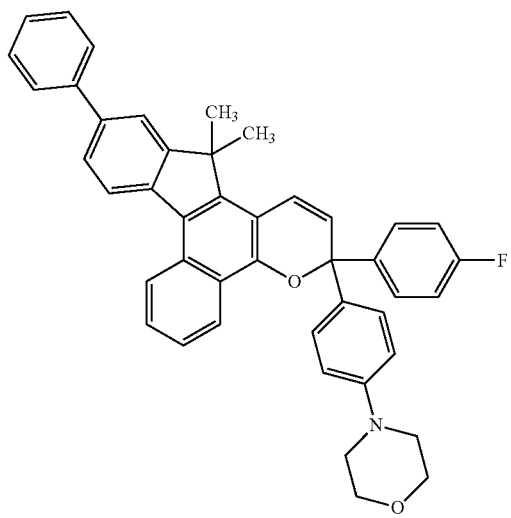

(l)

With reference to Formula (I) and Formula (j), $R^1$ is methoxy, $R^2$ is phenyl, $R^3$ and $R^4$ are each propyl, and B and B' are each 4-hydroxyphenyl.

In accordance with some embodiments, a non-limiting example of an indeno-fused naphthopyran represented by Formula (I) includes, but is not limited to, (k) 3-phenyl-3-(4-piperidinophenyl)-1'-phenyl-13,13-dimethyl-3H,13H-indeno[2',3':3,4]naphtho[1,2-b]pyran, which is represented by the following Formula (k), With reference to Formula (I) and Formula (l), $R^1$ is hydrogen, $R^2$ is phenyl, $R^3$ and $R^4$ are each methyl, B is 4-fluorophenyl, and B' is 4-morpholinophenyl.

In accordance with some embodiments, a non-limiting example of an indeno-fused naphthopyran represented by Formula (I) includes, but is not limited to, (m) 3,3-bis-(4-methoxyphenyl)-1'-(2,4-dimethoxyphenyl)-13,13-dimethyl-3H,13H-indeno[2',3':3,4]naphtho[1,2-b]pyran, which is represented by the following Formula (m),

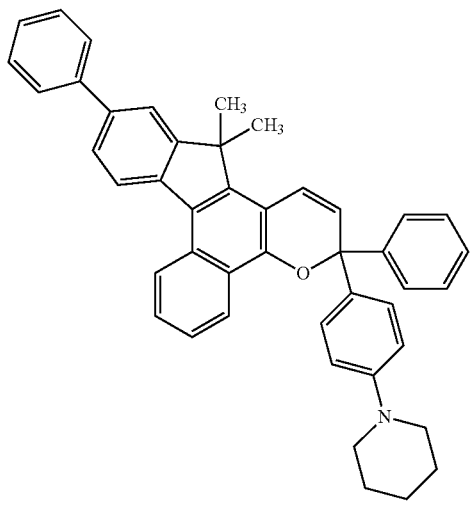

(k)

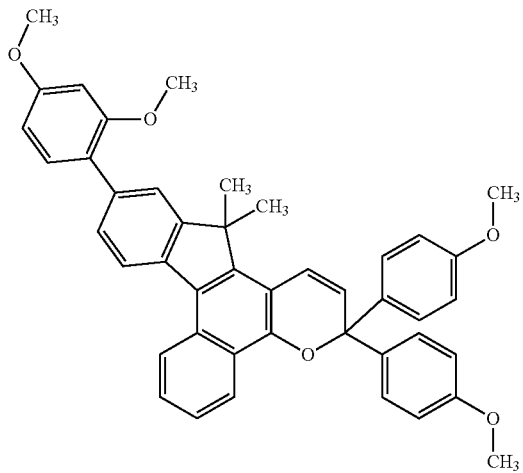

(m)

With reference to Formula (I) and Formula (k), $R^1$ is hydrogen, $R^2$ is phenyl, $R^3$ and $R^4$ are each methyl, B is phenyl, and B' is 4-piperidinophenyl.

In accordance with some embodiments, a non-limiting example of an indeno-fused naphthopyran represented by Formula (I) includes, but is not limited to, (l) 3-(4-fluorophenyl)-3-(4-morpholinophenyl)-1'-phenyl-13,13-dimethyl-3H,13H-indeno[2',3':3,4]naphtho[1,2-b]pyran, which is represented by the following Formula (l), With reference to Formula (I) and Formula (m), $R^1$ is hydrogen, $R^2$ is 2,4-dimethoxyphenyl, $R^3$ and $R^4$ are each methyl, and B and B' are each 4-methoxyphenyl.

In accordance with some embodiments, a non-limiting example of an indeno-fused naphthopyran represented by Formula (I) includes, but is not limited to, (n) 3,3-bis-(4-methoxyphenyl)-11-(4-(4,5-diphenyl-1H-imidazol-2-yl) phenyl)-13,13-dimethyl-3H,13H-indeno[2',3':3,4]naphtho[1,2-b]pyran, which is represented by the following Formula (n), (n)

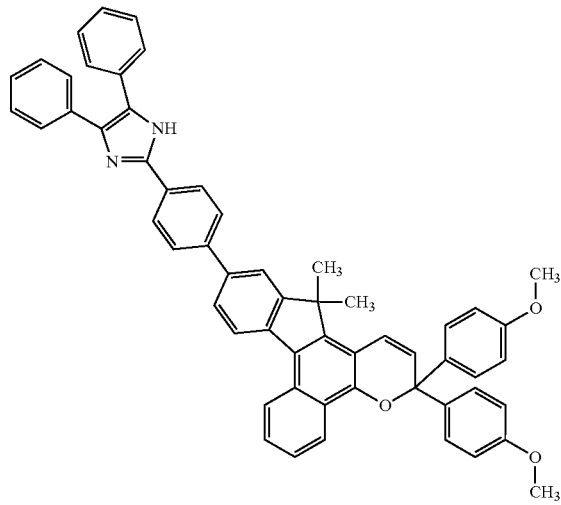

(p)

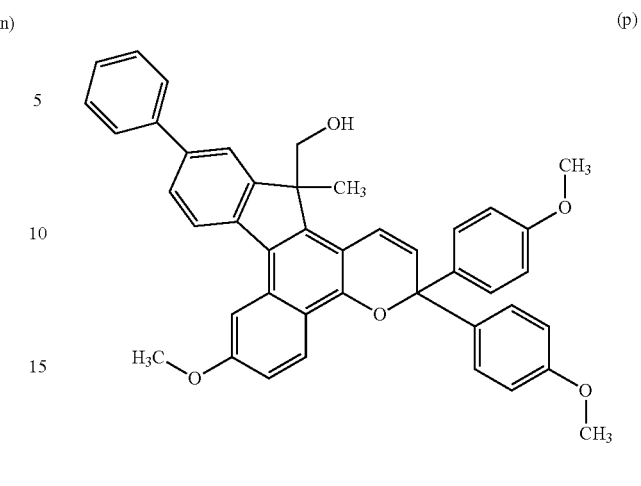

With reference to Formula (I) and Formula (n), R¹ is hydrogen, R² is 4-(4,5-diphenyl-1H-imidazol-2-yl)phenyl, R³ and R⁴ are each methyl, and B and B' are each 4-methoxyphenyl.

In accordance with some embodiments, a non-limiting example of an indeno-fused naphthopyran represented by Formula (I) includes, but is not limited to, (o) 3,3-bis-(4-methoxyphenyl)-7-methoxy-11-phenyl-13-carbomethoxy-13-methyl-3H,13H-indeno[2',3':3,4]naphtho[1,2-b]pyran, which is represented by the following Formula (o), With reference to Formula (I) and Formula (o), R¹ is methoxy, R² is phenyl, R³ is hydroxylmethyl, R⁴ is methyl, and B and B' are each 4-methoxyphenyl.

In accordance with some embodiments, a non-limiting example of an indeno-fused naphthopyran represented by Formula (I) includes, but is not limited to, (q) 3-(4-butoxyphenyl)-3-(4-morpholinophenyl)-7-methoxy-1'-(2-methoxyphenyl)-13,13-dimethyl-3H,13H-indeno[2',3':3,4]naphtho[1,2-b]pyran, which is represented by the following Formula (q), (o)

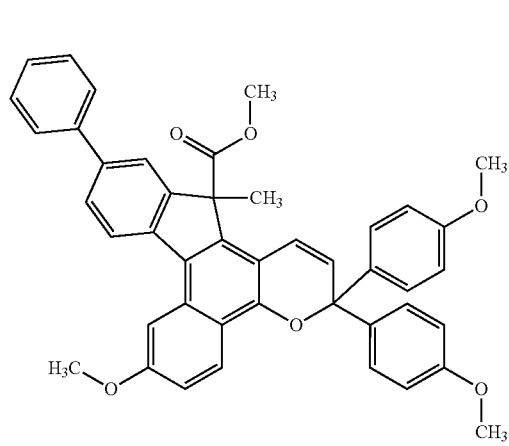

(q)

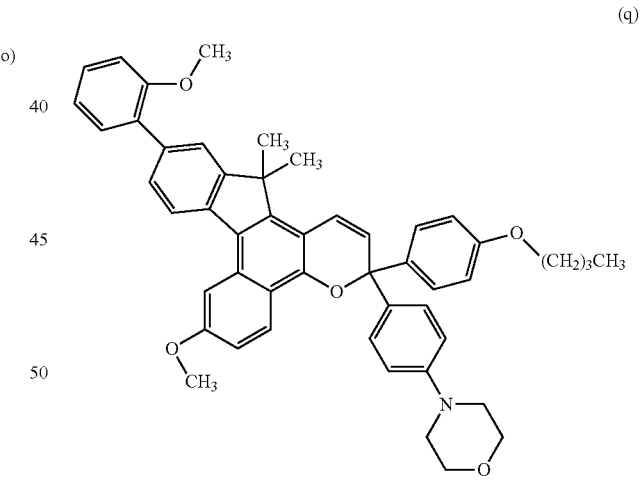

With reference to Formula (I) and Formula (o), R¹ is methoxy, R² is phenyl, R³ is carbomethoxy, R⁴ is methyl, and B and B' are each 4-methoxyphenyl.

In accordance with some embodiments, a non-limiting example of an indeno-fused naphthopyran represented by Formula (I) includes, but is not limited to, (p) 3,3-bis-(4-methoxyphenyl)-7-methoxy-11-phenyl-13-hydroxymethyl-13-methyl-3H,13H-indeno[2',3':3,4]naphtho[1,2-b]pyran, which is represented by the following Formula (p), With reference to Formula (I) and Formula (q), R¹ is methoxy, R² is 2-methoxyphenyl, R³ and R⁴ are each methyl, B is 4-butoxyphenyl, and B' is 4-morpholinophenyl.

In accordance with some embodiments, a non-limiting example of an indeno-fused naphthopyran represented by Formula (I) includes, but is not limited to, (r) 3,3-bis-(4-butoxyphenyl)-7-methoxy-1'-phenyl-13,13-dimethyl-3H,13H-indeno[2',3':3,4]naphtho[1,2-b]pyran, which is represented by the following Formula (r),

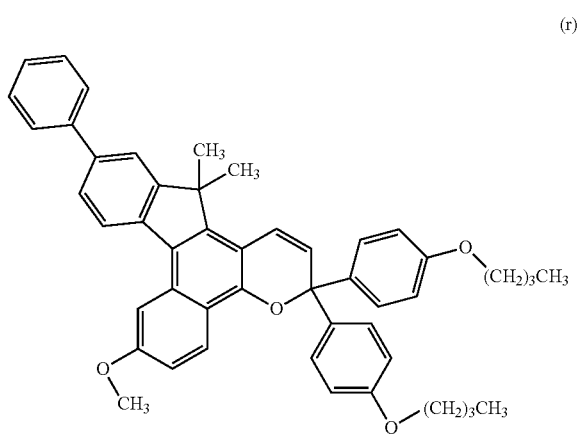

(r)

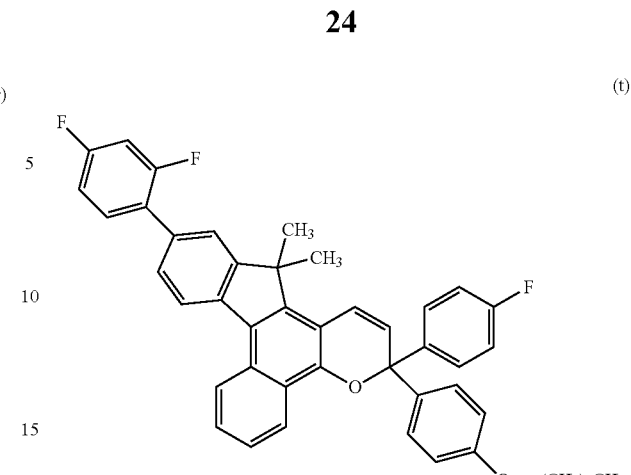

(t)

With reference to Formula (I) and Formula (r), $R^1$ is methoxy, $R^2$ is phenyl, $R^3$ and $R^4$ are each methyl, and B and B' are each 4-butoxyphenyl.

In accordance with some embodiments, a non-limiting example of an indeno-fused naphthopyran represented by Formula (I) includes, but is not limited to, (s) 3-(4-morpholinophenyl)-3-phenyl-1'-(4-t-butylphenyl)-13,13-dimethyl-3H,13H-indeno[2',3':3,4]naphtho[1,2-b]pyran, which is represented by the following Formula (s), With reference to Formula (I) and Formula (t), $R^1$ is hydrogen, $R^2$ is 2,4-difluorophenyl, $R^3$ and $R^4$ are each methyl, B is 4-fluorophenyl, and B' is 4-butoxyphenyl.

In accordance with some embodiments, a non-limiting example of an indeno-fused naphthopyran represented by Formula (I) includes, but is not limited to, (u) 3-(4-butoxyphenyl)-3-(4-fluorophenyl)-11-(9,9-bis-(2-ethylhexyl)-9H-fluoren-2-yl)-13,13-dimethyl-3H,13H-indeno[2',3':3,4]naphtho[1,2-b]pyran, which is represented by the following Formula (u),

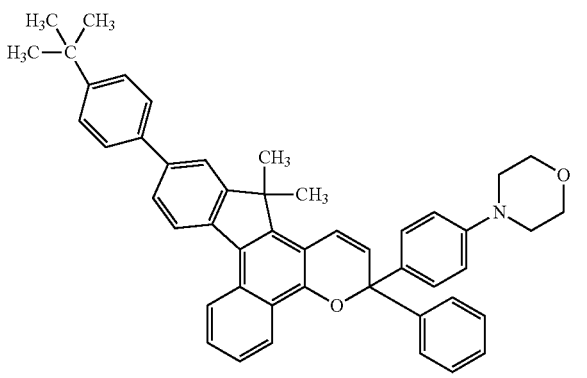

(s)

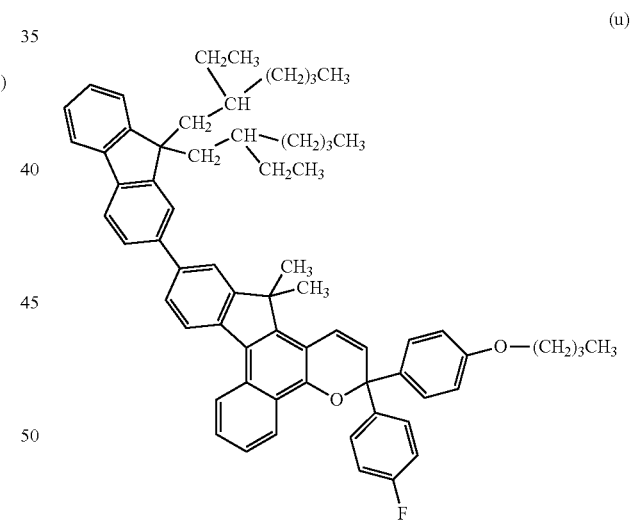

(u)

With reference to Formula (I) and Formula (s), $R^1$ is hydrogen, $R^2$ is 4-t-butylphenyl, $R^3$ and $R^4$ are each methyl, B is 4-morpholinophenyl, and B' is phenyl.

In accordance with some embodiments, a non-limiting example of an indeno-fused naphthopyran represented by Formula (I) includes, but is not limited to, (t) 3-(4-butoxyphenyl)-3-(4-fluorophenyl)-11-(2,4-difluorophenyl)-13,13-dimethyl-3H,13H-indeno[2',3':3,4]naphtho[1,2-b]pyran, which is represented by the following Formula (t), With reference to Formula (I) and Formula (u), $R^1$ is hydrogen, $R^2$ is 9,9-bis-(2-ethylhexyl)-9H-fluoren-2-yl, $R^3$ and $R^4$ are each methyl, B is 4-butoxyphenyl, and B' is 4-fluorophenyl.

In accordance with some embodiments, a non-limiting example of an indeno-fused naphthopyran represented by Formula (I) includes, but is not limited to, (v) 3-(4-butoxyphenyl)-3-(4-methoxyphenyl)-7-methoxy-11-(5-pyrimidinyl)-13,13-dimethyl-3H,13H-indeno[2',3':3,4]naphtho[1,2-b]pyran, which is represented by the following Formula (v),

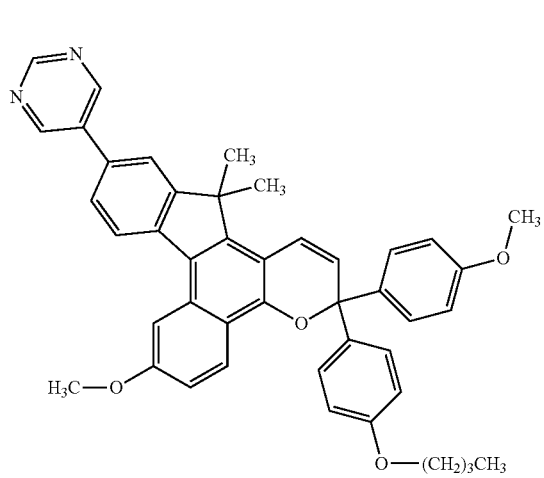

(v)

With reference to Formula (I) and Formula (v), $R^1$ is methoxy, $R^2$ is 5-pyrimidinyl, $R^3$ and $R^4$ are each methyl, B is 4-methoxyphenyl, and B' is 4-butoxyphenyl.

In accordance with some embodiments, a non-limiting example of an indeno-fused naphthopyran represented by Formula (I) includes, but is not limited to, (w) 3-(4-butoxyphenyl)-3-(4-methoxyphenyl)-7-methoxy-11-(9,9-bis-(2-ethylhexyl)-9H-fluoren-2-yl)-13,13-dimethyl-3H,13H-indeno[2',3':3,4]naphtho[1,2-b]pyran, which is represented by the following Formula (w),

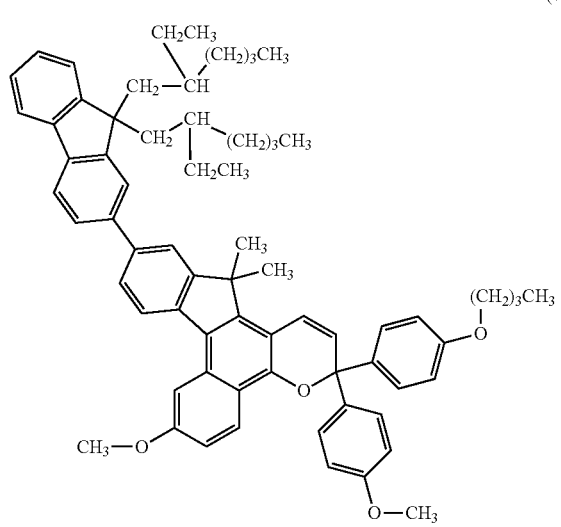

(w)

With reference to Formula (I) and Formula (w), $R^1$ is methoxy, $R^2$ is 9,9-bis-(2-ethylhexyl)-9H-fluoren-2-yl, $R^3$ and $R^4$ are each methyl, B is 4-butoxyphenyl, and B' is 4-methoxyphenyl.

In accordance with some embodiments, a non-limiting example of an indeno-fused naphthopyran represented by Formula (I) includes, but is not limited to, (x) 3-(4-morpholinophenyl)-3-(4-methoxyphenyl)-7-methoxy-11-(9,9-bis-(2-ethylhexyl)-9H-fluoren-2-yl)-13,13-dimethyl-3H,13H-indeno[2',3':3,4]naphtho[1,2-b]pyran, which is represented by the following Formula (x),

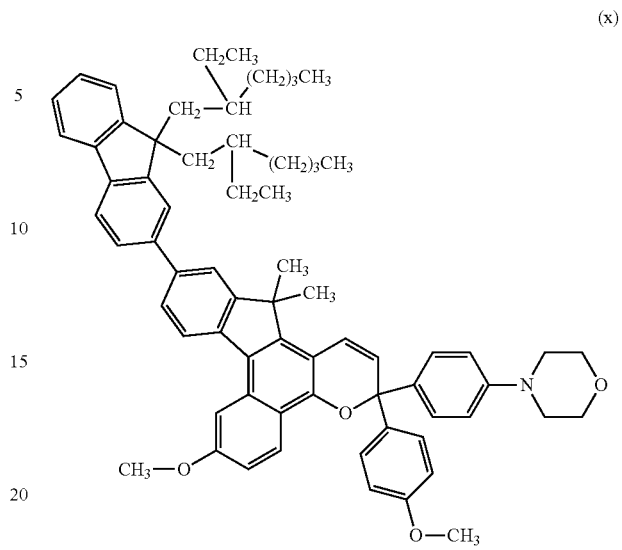

(x)

With reference to Formula (I) and Formula (x), $R^1$ is methoxy, $R^2$ is 9,9-bis-(2-ethylhexyl)-9H-fluoren-2-yl, $R^3$ and $R^4$ are each methyl, B is 4-morpholinophenyl, and B' is 4-methoxyphenyl.

In accordance with some embodiments, a non-limiting example of an indeno-fused naphthopyran represented by Formula (I) includes, but is not limited to, (y) 3-(4-(2-hydroxyethoxy)phenyl)-3-(4-methoxyphenyl)-11-(4-(N,N-dimethylamino)phenyl)-13,13-dimethyl-3H,13H-indeno[2',3':3,4]naphtho[1,2-b]pyran, which is represented by the following Formula (y),

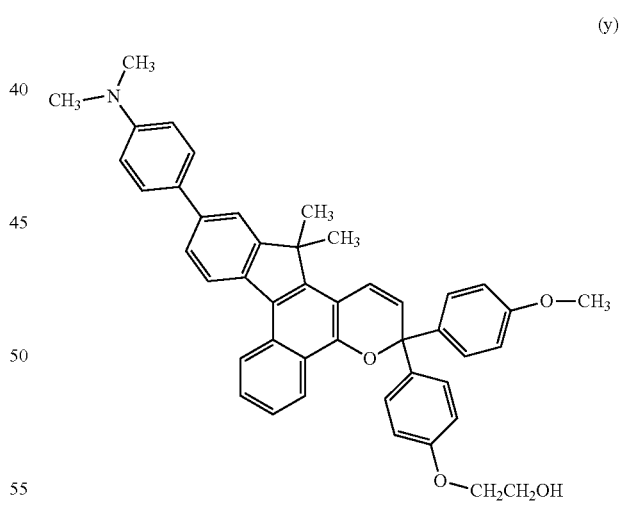

(y)

With reference to Formula (I) and Formula (y), $R^1$ is hydrogen, $R^2$ is 4-(N,N-dimethylamino)phenyl, $R^3$ and $R^4$ are each methyl, B is 4-methoxyphenyl, and B' is 4-(2-hydroxyethoxy)phenyl.

In accordance with some embodiments, a non-limiting example of an indeno-fused naphthopyran represented by Formula (I) includes, but is not limited to, (z) 3-(4-(allyloxy)phenyl)-3-(4-morpholinophenyl)-7-methoxy-1'-phenyl-13,13-dimethyl-3H,13H-indeno[2',3':3,4]naphtho[1,2-b]pyran, which is represented by the following Formula (z), (z)

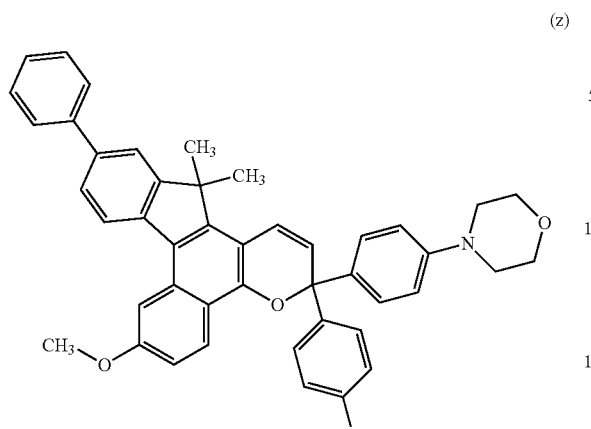

With reference to Formula (I) and Formula (z), $R^1$ is methoxy, $R^2$ is phenyl, $R^3$ and $R^4$ are each methyl, B is 4-morpholinophenyl, and B' is 4-(allyloxy)phenyl.

In accordance with some embodiments, a non-limiting example of an indeno-fused naphthopyran represented by Formula (I) includes, but is not limited to, (aa) 3-(4-(N,N-di-p-tolylaniline))-3-(4-methoxyphenyl)-7-methoxy-1'-phenyl-13,13-dimethyl-3H,13H-indeno[2',3':3,4]naphtho[1,2-b]pyran, which is represented by the following Formula (aa), (aa)

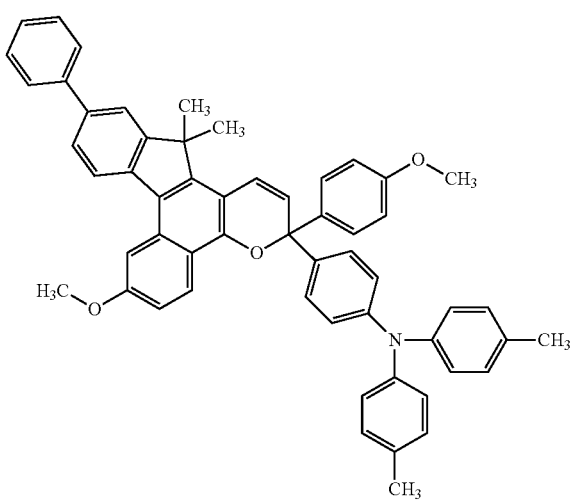

With reference to Formula (I) and Formula (aa), $R^1$ is methoxy, $R^2$ is phenyl, $R^3$ and $R^4$ are each methyl, B is 4-methoxyphenyl, and B' is 4-(N,N-di-p-tolylaniline).

In accordance with some embodiments, a non-limiting example of an indeno-fused naphthopyran represented by Formula (I) includes, but is not limited to, (bb) 3-(4-(N,N-di-p-tolylaniline))-3-(4-methoxyphenyl)-11-phenyl-13,13-dimethyl-3H,13H-indeno[2',3':3,4]naphtho[1,2-b]pyran, which is represented by the following Formula (bb), (bb)

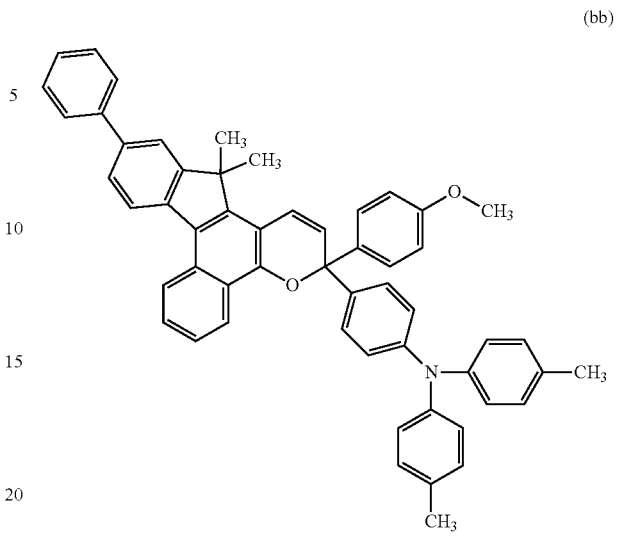

With reference to Formula (I) and Formula (bb), $R^1$ is hydrogen, $R^2$ is phenyl, $R^3$ and $R^4$ are each methyl, B is 4-methoxyphenyl, and B' is 4-(N,N-di-p-tolylaniline).

As previously discussed, B and B' of the indeno-fused naphthopyran can each be selected from an ary group that is mono-substituted with a reactive substituent or a compatibilizing substituent. If the indeno-fused naphthopyan includes multiple reactive substituents and/or multiple compatibilizing substituents, each reactive substituent and each compatibilizing substituent can be independently chosen.

The reactive substituent and the compatibilizing substituent can each independently be represented in each case by one of:

| | | |
|---|---|---|
| -A'-D-E-G-J (XIII); | -G-E-G-J (XVI); | -D-E-G-J (XIX); |
| -A'-D-J (XIV); | -D-G-J (XVII); | -D-J (XX); |
| -A'-G-J (XV); | -G-J (XVIII); and | -A'-J (XXI). |

With formulas (XIII) through (XXI), non-limiting examples of groups that -A'- can represent according to various non-limiting embodiments disclosed herein include —O—, —C(=O)—, —CH$_2$—, —OC(=O)— and —NHC(=O)—, provided that if -A'- represents —O—, -A'- forms at least one bond with -J.

Non-limiting examples of groups that -D- can represent according to various non-limiting embodiments include a diamine residue or a derivative thereof, wherein a first amino nitrogen of said diamine residue can form a bond with -A'-, or a substituent or an available position on the indeno-fused naphthopyran, and a second amino nitrogen of said diamine residue can form a bond with -E-, -G- or -J; and an amino alcohol residue or a derivative thereof, wherein an amino nitrogen of said amino alcohol residue can form a bond with -A'-, or a substituent or an available position on the indeno-fused naphthopyran, and an alcohol oxygen of said amino alcohol residue can form a bond with -E-, -G- or -J. Alternatively, according to various non-limiting embodiments disclosed herein the amino nitrogen of the amino alcohol residue can form a bond with -E-, -G- or -J, and the alcohol oxygen of the amino alcohol residue can form a bond with -A'-, or a substituent or an available position on the indeno-fused naphthopyran.

Non-limiting examples of suitable diamine residues that -D- can represent include an aliphatic diamine residue, a cyclo aliphatic diamine residue, a diazacycloalkane residue, an azacyclo aliphatic amine residue, a diazacrown ether residue, and an aromatic diamine residue. More particular, illustrative and non-limiting examples of diamine residues that can be used in conjunction with various non-limiting embodiments disclosed herein include the following:

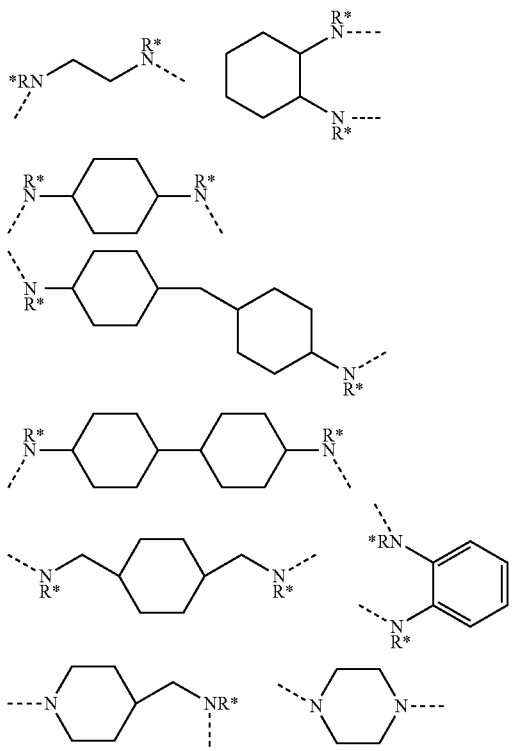

R* = H or alkyl

Non-limiting examples of suitable amino alcohol residues that -D- can represent include an aliphatic amino alcohol residue, a cyclo aliphatic amino alcohol residue, an azacyclo aliphatic alcohol residue, a diazacyclo aliphatic alcohol residue and an aromatic amino alcohol residue. More particular, illustrative and non-limiting examples of amino alcohol residues that can be used in conjunction with various non-limiting embodiments disclosed herein include the following:

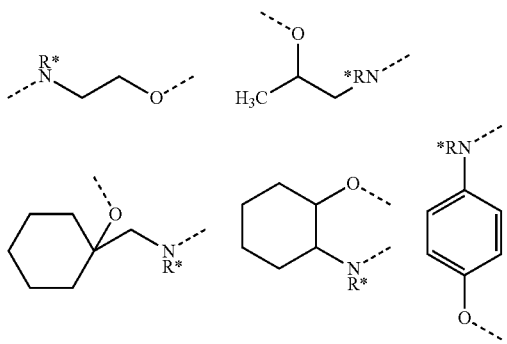

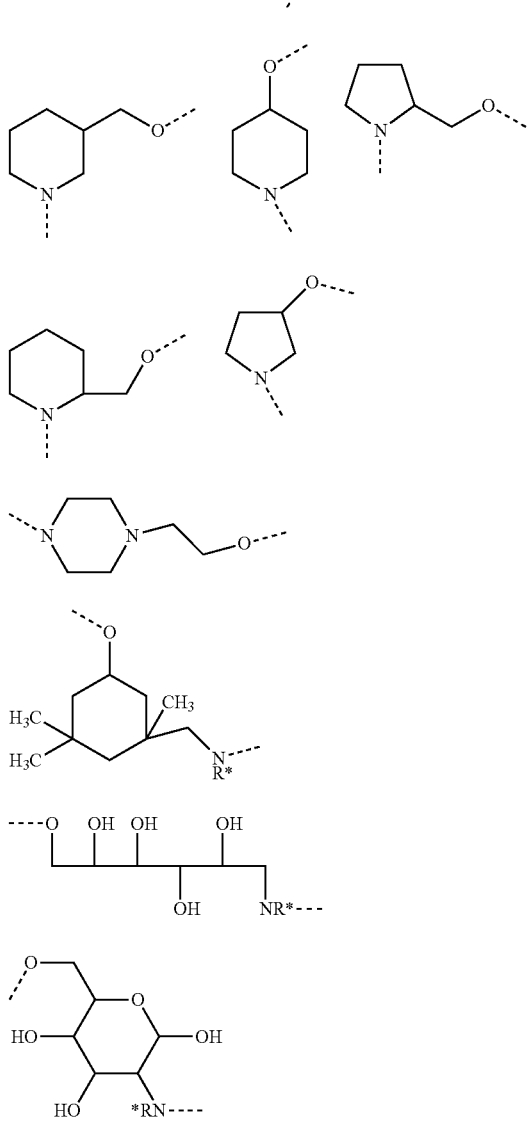

R* = H, alkyl

With continued reference to formulas (XIII) through (XXI) above, according to various non-limiting embodiments disclosed herein, -E- can represent a dicarboxylic acid residue or a derivative thereof, wherein a first carbonyl group of said dicarboxylic acid residue can form a bond with -G- or -D-, and a second carbonyl group of said dicarboxylic acid residue can form a bond with -G-. Non-limiting examples of suitable dicarboxylic acid residues that -E- can represent include an aliphatic dicarboxylic acid residue, a cycloaliphatic dicarboxylic acid residue and an aromatic dicarboxylic acid residue. More particular, illustrative and non-limiting examples of dicarboxylic acid residues that can be used in conjunction with various non-limiting embodiments disclosed herein include the following:

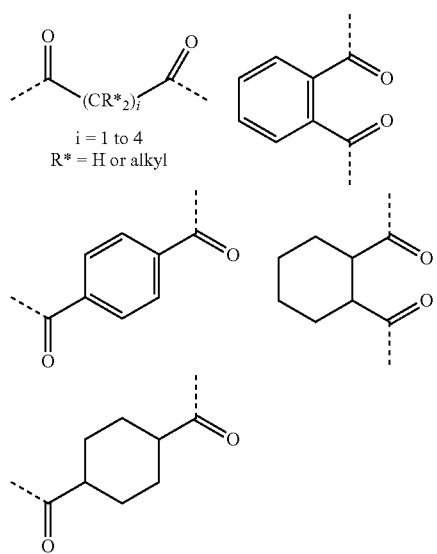

According to various non-limiting embodiments disclosed herein, -G- can represent a group represented by the following general formula,

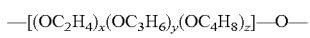

in which x, y and z are each independently chosen and range from 0 to 50, and a sum of x, y, and z ranges from 1 to 50; a polyol residue or a derivative thereof, wherein a first polyol oxygen of said polyol residue can form a bond with -A'-, -D-, -E-, or a substituent or an available position on the indeno-fused naphthopyran, and a second polyol oxygen of said polyol can form a bond with -E- or -J; or a combination thereof, wherein the first polyol oxygen of the polyol residue forms a bond with a group —[(OC$_2$H$_4$)$_x$(OC$_3$H$_6$)$_y$(OC$_4$H$_8$)$_z$]— (i.e., to form the group —[(OC$_2$H$_4$)$_x$(OC$_3$H$_6$)$_y$(OC$_4$H$_8$)$_z$]—O—), and the second polyol oxygen forms a bond with -E- or -J. Non-limiting examples of suitable polyol residues that -G- can represent include an aliphatic polyol residue, a cyclo aliphatic polyol residue and an aromatic polyol residue.

More particular, illustrative and non-limiting examples of polyols from which the polyol residues that -G- can represent can be formed according to various non-limiting embodiments disclosed herein include (a) low molecular weight polyols having an average molecular weight less than 500, such as, but not limited to, those set forth in U.S. Pat. No. 6,555,028 at col. 4, lines 48-50, and col. 4, line 55 to col. 6, line 5, which disclosure is hereby specifically incorporated by reference herein; (b) polyester polyols, such as, but not limited to, those set forth in U.S. Pat. No. 6,555,028 at col. 5, lines 7-33, which disclosure is hereby specifically incorporated by reference herein; (c) polyether polyols, such as but not limited to those set forth in U.S. Pat. No. 6,555,028 at col. 5, lines 34-50, which disclosure is hereby specifically incorporated by reference herein; (d) amide-containing polyols, such as, but not limited to, those set forth in U.S. Pat. No. 6,555,028 at col. 5, lines 51-62, which disclosure is hereby specifically incorporated by reference; (e) epoxy polyols, such as, but not limited to, those set forth in U.S. Pat. No. 6,555,028 at col. 5 line 63 to col. 6, line 3, which disclosure is hereby specifically incorporated by reference herein; (f) polyhydric polyvinyl alcohols, such as, but not limited to, those set forth in U.S. Pat. No. 6,555,028 at col. 6, lines 4-12, which disclosure is hereby specifically incorporated by reference herein; (g) urethane polyols, such as, but not limited to those set forth in U.S. Pat. No. 6,555,028 at col. 6, lines 13-43, which disclosure is hereby specifically incorporated by reference herein; (h) polyacrylic polyols, such as, but not limited to those set forth in U.S. Pat. No. 6,555,028 at col. 6, lines 43 to col. 7, line 40, which disclosure is hereby specifically incorporated by reference herein; (i) polycarbonate polyols, such as, but not limited to, those set forth in U.S. Pat. No. 6,555,028 at col. 7, lines 41-55, which disclosure is hereby specifically incorporated by reference herein; and (j) mixtures of such polyols.

With further reference to formulas (XIII) through (XXI), according to various non-limiting embodiments disclosed herein, -J can represent a group -K, wherein -K represents a group such as, but not limited to, —CH$_2$COOH, —CH(CH$_3$)COOH, —C(O)(CH$_2$)$_w$COOH, —C$_6$H$_4$SO$_3$H, —C$_5$H$_{10}$SO$_3$H, —C$_4$H$_8$SO$_3$H, —C$_3$H$_6$SO$_3$H, —C$_2$H$_4$SO$_3$H and —SO$_3$H, wherein "w" ranges from 1 to 18. According to other non-limiting embodiments -J can represent hydrogen that forms a bond with an oxygen or a nitrogen of linking group to form a reactive moiety such as —OH or —NH. For example, according to various non-limiting embodiments disclosed herein, -J can represent hydrogen, provided that if -J represents hydrogen, -J is bonded to an oxygen of -D- or -G-, or a nitrogen of -D-.

According to still further non-limiting embodiments, -J can represent a group -L or residue thereof, wherein -L can represent a reactive moiety. For example, according to various non-limiting embodiments disclosed herein -L can represent a group such as, but not limited to, acryl, methacryl, crotyl, 2-(methacryloxy)ethylcarbamyl, 2-(methacryloxy)ethoxycarbonyl, 4-vinylphenyl, vinyl, 1-chlorovinyl or epoxy. As used herein, the terms acryl, methacryl, crotyl, 2-(methacryloxy)ethylcarbamyl, 2-(methacryloxy)ethoxycarbonyl, 4-vinylphenyl, vinyl, 1-chlorovinyl, and epoxy refer to the following structures:

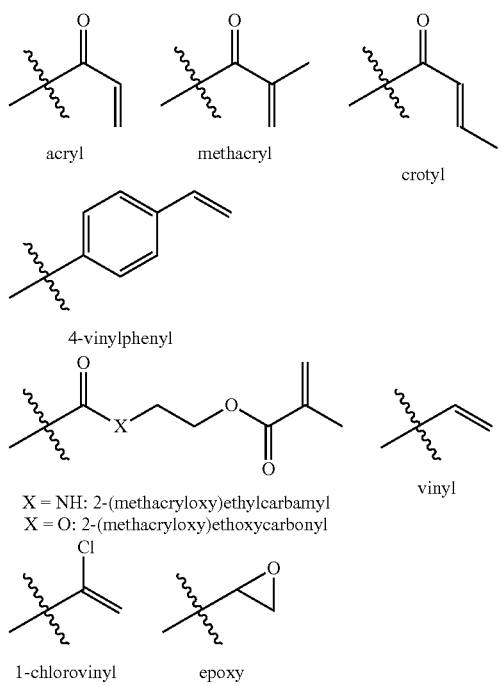

As previously discussed, -G- can represent a residue of a polyol, which is defined herein to include hydroxy-containing carbohydrates, such as those set forth in U.S. Pat. No. 6,555,028 at col. 7, line 56 to col. 8, line 17, which disclosure is hereby specifically incorporated by reference herein. The polyol residue can be formed, for example and without limitation herein, by the reaction of one or more of the polyol hydroxyl groups with a precursor of -A'-, such as a carboxylic acid or a methylene halide, a precursor of polyalkoxylated group, such as polyalkylene glycol, or a hydroxyl substituent of the indeno-fused naphthopyran. The polyol can be represented by q-(OH)$_a$ and the residue of the polyol can be represented by the formula —O-q-(OH)$_{a-1}$, wherein q is the backbone or main chain of the polyhydroxy compound and "a" is at least 2.

Further, as discussed above, one or more of the polyol oxygens of -G- can form a bond with -J (i.e., forming the group -G-J). For example, although not limiting herein, wherein the reactive and/or compatiblizing substituent comprises the group -G-J, if -G- represents a polyol residue and -J represents a group -K that contains a carboxyl terminating group, -G-J can be produced by reacting one or more polyol hydroxyl groups to form the group -K (for example as discussed with respect to Reactions B and C at col. 13, line 22 to col. 16, line 15 of U.S. Pat. No. 6,555,028, which disclosure is hereby specifically incorporated by reference herein) to produce a carboxylated polyol residue. Alternatively, if -J represents a group -K that contains a sulfo or sulfono terminating group, although not limiting herein, -G-J can be produced by acidic condensation of one or more of the polyol hydroxyl groups with $HOC_6H_4SO_3H$; $HOC_5H_{10}SO_3H$; $HOC_4H_8SO_3H$; $HOC_3H_6SO_3H$; $HOC_2H_4SO_3H$; or $H_2SO_4$, respectively. Further, although not limiting herein, if -G- represents a polyol residue and -J represents a group -L chosen from acryl, methacryl, 2-(methacryloxy)ethylcarbamyl and epoxy, -L can be added by condensation of the polyol residue with acryloyl chloride, methacryloyl chloride, 2-isocyanatoethyl methacrylate or epichlorohydrin, respectively.

Additional description of reactive substituents that can be used in connection with the photochromic materials described herein is set forth at col. 5, line 42 to col. 15, line 28, in U.S. Pat. No. 7,556,750, entitled PHOTOCHROMIC MATERIALS WITH REACTIVE SUBSTITUENTS, which is hereby specifically incorporated by reference herein. Further non-limiting examples of reactive and/or compatiblizing substituents are set forth in U.S. Pat. No. 6,555,028, at col. 3, line 45 to col. 4, line 26, and U.S. Pat. No. 6,113,814 at col. 3, lines 30-64, which disclosures are hereby specifically incorporated by reference herein.

The indeno-fused naphthopyran compounds of the present invention can be prepared by art-recognized methods. With some embodiments, the indeno-fused naphthopyran compounds of the present invention can be synthesized in accordance with the description provided in U.S. Pat. No. 6,296,785, at column 10, line 52 through column 29, line 18, which disclosure is incorporated herein by reference. With some further embodiments, the indeno-fused naphthopyran compounds of the present invention can be synthesized in accordance with the description provided in U.S. Pat. No. 7,527,754 B2 at column 13, line 52 through column 14, line 62, which disclosure is incorporated herein by reference. With some additional further embodiments, the indeno-fused naphthopyran compounds of the present invention can be synthesized in accordance with the description provided in U.S. Pat. No. 5,645,767, at column 5, line 6 through column 11, line 31, which disclosure is incorporated herein by reference.

With some embodiments, the indeno-fused naphthopyran compounds of the present invention are prepared in accordance with the synthetic descriptions provided in the examples further herein.

With some embodiments, the indeno-fused naphthopyran compounds of the present invention can each be used alone, or in combination with other photochromic compounds. For example, the indeno-fused naphthopyran compounds of the present invention can be used in conjunction with other photochromic compounds having activated absorption maxima within the range of 300 to 1000 nanometers. Further, the indeno-fused naphthopyran compounds according to the present invention can be used in conjunction with a complementary conventional polymerizable or a compatiblized photochromic compound, such as for example, those disclosed in U.S. Pat. No. 6,113,814 (at col. 2, line 39 to col. 8, line 41), and U.S. Pat. No. 6,555,028 (at col. 2, line 65 to col. 12, line 56), which disclosures are hereby specifically incorporated by reference herein.

The indeno-fused naphthopyran compounds of the present invention can be used in combination with a mixture of other photochromic compounds. For example, although not limiting herein, mixtures of photochromic compounds can be used to attain certain activated colors such as a near neutral gray or near neutral brown. See, for example, U.S. Pat. No. 5,645,767, col. 12, line 66 to col. 13, line 19, which describes the parameters that define neutral gray and brown colors and which disclosure is specifically incorporated by reference herein.

Examples of classes of other photochromic compounds that can be used in combination with the indeno-fused naphthopyrans of the present invention, include, but are not limited to, indeno-fused naphthopyrans, naphtho[1,2-b]pyrans, naphtho[2,1-b]pyrans, spirofluoroeno[1,2-b]pyrans, phenanthropyrans, quinolinopyrans, fluoroanthenopyrans, spiropyrans, benzoxazines, naphthoxazines, spiro(indoline)naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, thermally reversible photochromic compounds, and non-thermally reversible photochromic compounds, and mixtures thereof.

Non-limiting examples of photochromic pyrans that can be used in combination with the indeno-fused naphthopyrans of the present invention, include, but are not limited to, benzopyrans, naphthopyrans, e.g., naphtho[1,2-b]pyrans, naphtho[2,1-b]pyrans, indeno-fused naphthopyrans, such as those disclosed in U.S. Pat. No. 5,645,767, and heterocyclic-fused naphthopyrans, such as those disclosed in U.S. Pat. Nos. 5,723,072, 5,698,141, 6,153,126, and 6,022,497, which are hereby incorporated by reference; spiro-9-fluoreno[1,2-b]pyrans; phenanthropyrans; quinopyrans; fluoroanthenopyrans; spiropyrans, e.g., spiro(benzindoline)naphthopyrans, spiro(indoline)benzopyrans, spiro(indoline)naphthopyrans, spiro(indoline)quinopyrans and spiro(indoline)pyrans. Further examples of naphthopyrans and complementary organic photochromic compounds are described in U.S. Pat. No. 5,658,501, which are hereby specifically incorporated by reference herein. Spiro(indoline)pyrans are also described in the text, *Techniques in Chemistry*, Volume III, "Photochromism", Chapter 3, Glenn H. Brown, Editor, John Wiley and Sons, Inc., New York, 1971, which is hereby incorporated by reference.

Non-limiting examples of photochromic oxazines that can be used in combination with the indeno-fused naphthopyrans of the present invention, include, but are not limited to, benzoxazines, naphthoxazines, and spiro-oxazines, e.g., spiro (indoline)naphthoxazines, spiro(indoline)pyridobenzoxazines, spiro(benzindoline)pyridobenzoxazines, spiro(benzindoline)naphthoxazines, spiro(indoline)benzoxazines, spiro(indoline)fluoranthenoxazine, and spiro(indoline)quinoxazine. Non-limiting examples of photochromic fulgides that can be used in combination with the indeno-fused naphthopyrans of the present invention, include, but are not limited to: fulgimides, and the 3-furyl and 3-thienyl fulgides and fulgimides, which are disclosed in U.S. Pat. No. 4,931,220 (which are hereby specifically incorporated by reference) and mixtures of any of the aforementioned photochromic materials/compounds.

The present invention also relates to a photochromic article that includes the photochromic material of the present invention, and correspondingly includes one or more indeno-fused naphthopyran compounds represented by Formula (I) and/or Formula (II).

In accordance with further embodiments of the present invention, the photochromic articles of the present invention can be selected from ophthalmic articles or elements, display articles or elements, windows, mirrors, packaging material such as shrinkwrap, and active and passive liquid crystal cell articles or elements.

Examples of ophthalmic articles or elements include, but are not limited to, corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

Examples of display articles, elements and devices include, but are not limited to, screens, monitors, and security elements, including without limitation, security marks and authentication marks.

Examples of windows include, but are not limited to, automotive and aircraft transparencies, filters, shutters, and optical switches.

With some embodiments, the photochromic article can be a security element. Examples of security elements include, but are not limited to, security marks and authentication marks that are connected to at least a portion of a substrate, such as: access cards and passes, e.g., tickets, badges, identification or membership cards, debit cards, etc.; negotiable instruments and non-negotiable instruments e.g., drafts, checks, bonds, notes, certificates of deposit, stock certificates, etc.; government documents, e.g., currency, licenses, identification cards, benefit cards, visas, passports, official certificates, deeds etc.; consumer goods, e.g., software, compact discs ("CDs"), digital-video discs ("DVDs"), appliances, consumer electronics, sporting goods, cars, etc.; credit cards; and merchandise tags, labels and packaging.

With further embodiments, the security element can be connected to at least a portion of a substrate chosen from a transparent substrate and a reflective substrate. Alternatively, according to further embodiments in which a reflective substrate is required, if the substrate is not reflective or sufficiently reflective for the intended application, a reflective material can be first applied to at least a portion of the substrate before the security mark is applied thereto. For example, a reflective aluminum coating can be applied to the at least a portion of the substrate prior to forming the security element thereon. Additionally or alternatively, the security element can be connected to at least a portion of a substrate chosen from untinted substrates, tinted substrates, photochromic substrates, tinted-photochromic substrates, linearly polarizing, circularly polarizing substrates, and elliptically polarizing substrates.

Furthermore, security elements according to the aforementioned embodiments can further include one or more other coatings or films or sheets to form a multi-layer reflective security element with viewing angle dependent characteristics, such as described in U.S. Pat. No. 6,641,874.

Photochromic articles according to the present invention, such as optical elements, can include a substrate and a photochromic material that includes the indeno-fused naphthopyran compound or compounds according to the present invention, in which the photochromic material is connected to at least a portion of the substrate. As used herein, the term "connected to" means associated with, either directly, or indirectly by means of another material or structure.

Photochromic articles according to the present invention can include, as discussed above, a substrate that can include one or more polymeric compounds of the present invention. The indeno-fused naphthopyran compounds of the present invention can be incorporated into at least a portion of the polymeric material of the substrate; or by incorporating the indeno-fused naphthopyran compound(s) into at least a portion of the oligomeric or monomeric material from which the substrate is formed. For example, according to one non-limiting embodiment, the indeno-fused naphthopyran compound can be incorporated into the polymeric material of the substrate by a cast-in-place method or by imbibition. The imbibition and the cast-in-place methods are discussed in further detail herein below.

In the imbibition method, the photochromic compound is typically diffused into the polymeric material of a previously formed or fabricated article, such as a substrate or previously applied coating/film. Imbibition can be performed by immersing the polymeric material of a previously formed or fabricated article in a solution containing the photochromic compound, with or without heating. Thereafter, although not required, the photochromic compound can be bonded with the polymeric material (e.g., of the substrate or coating).

With cast-in-place methods, the photochromic compound(s) can be mixed with: a polymer and/or oligomer composition in solution or melt form; or monomer composition in liquid form, so as to form a castable photochromic composition. The castable photochromic composition is then typically introduced into the cavity of a mold (e.g., a lens mold). The castable photochromic composition is then set within the mold so as to form a photochromic article.

With photochromic articles according to the present invention that include a substrate, a photochromic compound(s) can be included in a coating that is connected to at least a portion of the substrate. The substrate can be a polymeric substrate or an inorganic substrate (such as, but not limited to, a glass substrate). The photochromic compound(s) can be incorporated into at least a portion of a coating composition prior to application of the coating composition to the substrate. Alternatively, a coating composition can be applied to the substrate, at least partially set, and thereafter the photochromic compound(s) can be imbibed into at least a portion of the coating. As used herein, the terms "set" and "setting" include, without limitation, curing, polymerizing, cross-linking, cooling, and drying.

Photochromic articles according to the present invention can be formed by art-recognized in-mold coating (or in-mold casting) methods. With in-mold coating methods, a photochromic coating composition that includes a photochromic indeno-fused naphthopyran compound(s) of the present invention, which can be a liquid coating composition or a powder coating composition, is applied to at least a portion of the interior surface of a mold, and then at least partially set. Thereafter, a polymer solution or melt, or oligomeric or monomeric solution or mixture is cast or molded within the mold cavity and in contact with the previously applied photochromic coating composition, and at least partially set. The resulting photochromic article is then removed from the mold. Non-limiting examples of powder coatings in which the photochromic materials according to various non-limiting embodiments disclosed herein can be employed are set forth in U.S. Pat. No. 6,068,797 at col. 7, line 50 to col. 19, line 42, which disclosure is hereby specifically incorporated by reference herein.

Photochromic articles according to the present invention can also be formed by art-recognized over-mold methods. Over-mold methods typically involve forming a substrate within a mold, and then forming an interior space between the substrate and an interior surface of the mold, into which a photochromic coating composition is then subsequently introduced (e.g., injected) and then set (e.g., cured). Alternatively, over-mold methods can involve introducing a previously formed substrate into a mold, such that an interior space is defined between the substrate and an interior mold surface, and thereafter a photochromic coating composition is introduced (e.g., injected) into the interior space. The photochromic coating compositions include one or more indeno-fused naphthopyran compounds of the present invention.

Photochromic articles according to the present invention can also be formed by art-recognized lamination methods. With lamination methods, a film comprising the photochromic indeno-fused naphthopyran compound(s) according to the present invention can be adhered or otherwise connect to a portion of the substrate, with or without an adhesive and/or the application of heat and pressure. Thereafter, if desired, a second substrate can be applied over the first substrate and the two substrates can be laminated together (i.e., by the application of heat and pressure) to form an element wherein the film comprising the photochromic compound is interposed between the two substrates. Methods of forming films comprising the photochromic indeno-fused naphthopyran compounds of the present invention can include for example and without limitation, combining a photochromic indeno-fused naphthopyran compound with a polymeric solution or oligomeric solution or mixture, casting or extruding a film therefrom, and, if required, at least partially setting the film. Additionally or alternatively, a film can be formed (with or without a photochromic compound) and imbibed with the photochromic compound.

Coating compositions that include the photochromic materials, including the one or more indeno-fused naphthopyran compounds represented by Formulas (I) and/or (II), of the present invention can be connected to at least a portion of the substrate of the photochromic article by art-recognized methods, such as applying a coating composition that includes the photochromic indeno-fused naphthopyran compound(s) to at least a portion of a surface of the substrate, and at least partially setting the coating composition. Additionally or alternatively, the coating that includes the photochromic indeno-fused naphthopyran compound(s) can be connected to the substrate, for example, through one or more additional coatings. For example, while not limiting herein, according to various non-limiting embodiments, an additional coating composition can be applied to a portion of the surface of the substrate, at least partially set, and thereafter the coating composition that includes the photochromic compound(s) can be applied over the additional coating and at least partially set. Non-limiting and art-recognized methods of applying coatings compositions to substrates are discussed herein below.

Examples of additional coatings and films that can be used in conjunction with the photochromic coatings and articles according to the present invention, include, but are not limited to: primer coatings and films (which typically reside under the photochromic coating); protective coatings and films (which are typically applied over the photochromic coating), including transitional coatings and films and abrasion resistant coatings and films; anti-reflective coatings and films; conventional photochromic coatings and films; polarizing coatings and films; and combinations thereof. As used herein the term "protective coating or film" refers to coatings or films that can prevent wear or abrasion, provide a transition in properties from one coating or film to another, protect against the effects of polymerization reaction chemicals and/or protect against deterioration due to environmental conditions such as moisture, heat, ultraviolet light, oxygen, etc.

As used herein, the term "transitional coating and film" means a coating or film that aids in creating a gradient in properties between two coatings or films, or a coating and a film. For example, although not limiting herein, a transitional coating can aid in creating a gradient in hardness between a relatively hard coating and a relatively soft coating. Non-limiting examples of transitional coatings include radiation-cured, acrylate-based thin films as described in U.S. Patent Application Publication 2003/0165686 at paragraphs 79-173, which are hereby specifically incorporated by reference herein.

As used herein the term "abrasion resistant coating and film" refers to a protective polymeric material that demonstrates a resistance to abrasion that is greater than a standard reference material, e.g., a polymer made of CR-39® monomer available from PPG Industries, Inc, as tested in a method comparable to ASTM F-735 Standard Test Method for Abrasion Resistance of Transparent Plastics and Coatings Using the Oscillating Sand Method. Non-limiting examples of abrasion resistant coatings include, for example, abrasion-resistant coatings comprising organosilanes, organosiloxanes, abrasion-resistant coatings based on inorganic materials such as silica, titania and/or zirconia, organic abrasion-resistant coatings of the type that are ultraviolet light curable, oxygen barrier-coatings, UV-shielding coatings, and combinations thereof.

Non-limiting examples of antireflective coatings and films include a monolayer, multilayer or film of metal oxides, metal fluorides, or other such materials, which can be deposited onto the articles disclosed herein (or onto films that are applied to the articles), for example, through vacuum deposition, sputtering, etc. Non-limiting examples of conventional photochromic coatings and films include, but are not limited to, coatings and films comprising conventional photochromic materials. Non-limiting examples of polarizing coatings and films include, but are not limited to, coatings and films comprising dichroic compounds that are known in the art.

Additional coating compositions (e.g., primers and overcoats) that can be used with photochromic coating compositions according to the present invention and/or to form photochromic articles according to the present invention, can be applied to/formed: on a substrate prior to application of the photochromic coating; and/or over a previously applied photochromic coating. For example, a primer coating can be formed on the substrate prior to applying a photochromic coating composition according to the present invention. Additionally or alternatively, an additional coating or film can be applied (e.g., as an over-coat or over-coating) at least partially over a previously applied photochromic coating composition according to the present invention. For example, a transitional coating can be formed over a previously applied photochromic coating composition according to the present invention, and an abrasion resistant coating can then be applied over the transitional coating.

In accordance with various non-limiting embodiments of the present invention, there is provided a photochromic composition comprising: an organic material, the organic material being at least one of polymeric material, an oligomeric material and a monomeric material; and a photochromic material according to any of the non-limiting embodiments of set forth above incorporated into at least a portion of the organic material. According to various non-limiting embodiments disclosed herein, the photochromic material can be incorporated into a portion of the organic material by at least one of blending and bonding the photochromic material with the organic material or a precursor thereof. As used herein with reference to the incorporation of photochromic materials into an organic material, the terms "blending" and "blended" mean that the photochromic material is intermixed or intermingled with the at least a portion of the organic material, but not bonded to the organic material. Further, as used herein with reference to the incorporation of photochromic materials into an organic material, the terms "bonding" or "bonded" mean that the photochromic material is linked to a portion of the organic material or a precursor thereof. For example, although not limiting herein, the photochromic material may be linked to the organic material through a reactive substituent.

In accordance with some non-limiting embodiments of the presenting invention, when the organic material is a polymeric material, the photochromic material can be incorporated into at least a portion of the polymeric material or at least a portion of the monomeric material or oligomeric material from which the polymeric material is formed. For example, photochromic materials according to various non-limiting embodiments disclosed herein that have a reactive substituent can be bonded to an organic material such as a monomer, oligomer, or polymer having a group with which a reactive moiety may be reacted, or the reactive moiety can be reacted as a co-monomer in the polymerization reaction from which the organic material is formed, for example, in a co-polymerization process.

As discussed above, the photochromic compositions according to various non-limiting embodiments disclosed herein can include an organic material chosen from a polymeric material, an oligomeric material and/or a monomeric material. Examples of polymeric materials that can be used in conjunction with various non-limiting embodiments disclosed herein include, without limitation: polymers of bis(allyl carbonate)monomers; diethylene glycol dimethacrylate monomers; diisopropenyl benzene monomers; ethoxylated bisphenol A dimethacrylate monomers; ethylene glycol bismethacrylate monomers; poly(ethylene glycol)bismethacrylate monomers; ethoxylated phenol bismethacrylate monomers; alkoxylated polyhydric alcohol acrylate monomers, such as ethoxylated trimethylol propane triacrylate monomers; urethane acrylate monomers; vinylbenzene monomers; and styrene. Other non-limiting examples of suitable polymeric materials include polymers of polyfunctional, e.g., mono-, di- or multi-functional, acrylate and/or methacrylate monomers; poly($C_1$-$C_{12}$ alkyl methacrylates), such as poly(methyl methacrylate); poly(oxyalkylene) dimethacrylate; poly(alkoxylated phenol methacrylates); cellulose acetate; cellulose triacetate; cellulose acetate propionate; cellulose acetate butyrate; poly(vinyl acetate); poly(vinyl alcohol); poly(vinyl chloride); poly(vinylidene chloride); polyurethanes; polythiourethanes; thermoplastic polycarbonates; polyesters; poly(ethylene terephthalate); polystyrene; poly(alpha-methylstyrene); copolymers of styrene and methyl methacrylate; copolymers of styrene and acrylonitrile; polyvinylbutyral; and polymers of diallylidene pentaerythritol, particularly copolymers with polyol (allyl carbonate)monomers, e.g., diethylene glycol bis(allyl carbonate), and acrylate monomers, e.g., ethyl acrylate, butyl acrylate. Also contemplated are copolymers of the aforementioned monomers, combinations, and blends of the aforementioned polymers and copolymers with other polymers, e.g., to form interpenetrating network products.

Further, according to various non-limiting embodiments in which transparency of the photochromic composition is desired, the organic material can be a transparent polymeric material. For example, according to various non-limiting embodiments, the polymeric material can be an optically clear polymeric material prepared from a thermoplastic polycarbonate resin, such as the resin derived from bisphenol A and phosgene, which is sold under the trademark, LEXAN®; a polyester, such as the material sold under the trademark, MYLAR®; a poly(methyl methacrylate), such as the material sold under the trademark, PLEXIGLAS®; and polymerizates of a polyol(allyl carbonate) monomer, especially diethylene glycol bis(allyl carbonate), which monomer is sold under the trademark CR-39®; and polyurea-polyurethane (polyurea urethane) polymers, which are prepared, for example, by the reaction of a polyurethane oligomer and a diamine curing agent, a composition for one such polymer being sold under the trademark TRIVEX® by PPG Industries, Inc. Other non-limiting examples of suitable polymeric materials include polymerizates of copolymers of a polyol (allyl carbonate), e.g., diethylene glycol bis(allyl carbonate), with other copolymerizable monomeric materials, such as, but not limited to: copolymers with vinyl acetate, copolymers with a polyurethane having terminal diacrylate functionality, and copolymers with aliphatic urethanes, the terminal portion of which contain allyl or acrylyl functional groups. Still other suitable polymeric materials include, without limitation, poly(vinyl acetate), polyvinylbutyral, polyurethane, polythiourethanes, polymers chosen from diethylene glycol dimethacrylate monomers, diisopropenyl benzene monomers, ethoxylated bisphenol A dimethacrylate monomers, ethylene glycol bismethacrylate monomers, poly(ethylene glycol)bismethacrylate monomers, ethoxylated phenol bismethacrylate monomers and ethoxylated trimethylol propane triacrylate monomers, cellulose acetate, cellulose propionate, cellulose butyrate, cellulose acetate butyrate, polystyrene and copolymers of styrene with methyl methacrylate, vinyl acetate and acrylonitrile. According to one non-limiting embodiment, the polymeric material can be an optical resins sold by PPG Industries, Inc. under the CR-designation, e.g., CR-307, CR-407, and CR-607.

In accordance with some embodiments, the organic material can be a polymeric material which is chosen from poly(carbonate), copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly(acrylate); poly(methacrylate); epoxies; aminoplast functional polymers; poly(anhydride); poly(urea urethane); N-alkoxymethyl(meth)acrylamide functional polymers; poly(siloxane); poly(silane); and combinations and mixtures thereof.

With some further embodiments, the photochromic composition of the present invention further includes at least one of, a complementary photochromic material (including one or more of those other photochromic materials and compounds described previously herein), a photoinitiator, a thermal initiator, a polymerization inhibitor, a solvent, a light stabilizer, a heat stabilizer, a mold release agent, a rheology control agent, a leveling agent, a free radical scavenger, and an adhesion promoter.

In accordance with some embodiments, the photochromic composition according to the present invention is a photochromic coating composition. Photochromic coating compositions according to some embodiments of the present invention include: a photochromic material according to the present invention, such as described previously herein with regard to the indeno-fused naphthopyran compounds represented by Formulas (I) and (II); a resin composition that is optionally curable; and optionally a solvent. The photochromic coating composition can be in the form of art-recognized liquid coatings and powder coatings. The photochromic coating compositions of the present invention can be thermoplastic or thermosetting coating compositions. In an embodiment, the photochromic coating composition is a curable or thermosetting coating composition.

The curable resin composition of the curable photochromic coating compositions according to some embodiments of the present invention include: a first reactant (or component) having functional groups, e.g., an epoxide functional polymer reactant; and a second reactant (or component) that is a crosslinking agent having functional groups that are reactive towards and that can form covalent bonds with the functional groups of the first reactant. The first and second reactants of the curable resin composition of the curable photochromic coating composition can each independently include one or more functional species, and are each present in amounts sufficient to provide cured photochromic coatings having a desirable combination of physical properties, e.g., smoothness, optical clarity, solvent resistance and hardness.

Examples of curable resin compositions that can be used with the curable photochromic coating compositions according to the present invention include, but are not limited to: curable resin compositions comprising epoxide functional polymer (e.g., (meth)acrylic polymers containing residues of glycidyl(meth)acrylate and epoxide reactive crosslinking agent (e.g., containing active hydrogens, such as hydroxyls, thiols and amines); and curable resin compositions comprising hydroxy functional polymer and capped (or blocked) isocyanate functional crosslinking agent.

In an embodiment, the curable resin composition of the photochromic coating composition of the present invention is a curable urethane (or polyurethane) resin composition. Curable urethane resin compositions useful in the photochromic coating compositions of the present invention typically include: an active hydrogen functional polymer, such as a hydroxy functional polymer; and a capped (or blocked) isocyanate functional crosslinking agent. Hydroxy functional polymers that can be used in such compositions include, but are not limited to, art-recognized hydroxy functional vinyl polymers, hydroxy functional polyesters, hydroxy functional polyurethanes and mixtures thereof.

Vinyl polymers having hydroxy functionality can be prepared by free radical polymerization methods that are known to those of ordinary skill in the art. In an embodiment of the present invention, the hydroxy functional vinyl polymer is prepared from a majority of (meth)acrylate monomers and is referred to herein as a "hydroxy functional (meth)acrylic polymer."

Hydroxy functional polyesters useful in curable photochromic coating compositions comprising capped isocyanate functional crosslinking agent can be prepared by art-recognized methods. Typically, diols and dicarboxylic acids or diesters of dicarboxylic acids are reacted in a proportion such that the molar equivalents of hydroxy groups is greater than that of carboxylic acid groups (or esters of carboxylic acid groups) with the concurrent removal of water or alcohols from the reaction medium.

Hydroxy functional urethanes can be prepared by art-recognized methods, for example, as previously described herein. Typically one or more difunctional isocyanates are reacted with one or more materials having two active hydrogen groups (e.g., diols or dithiols), such that the ratio of active hydrogen groups to isocyanate groups is greater than 1, as is known to the skilled artisan.

By "capped (or blocked) isocyanate crosslinking agent" is meant a crosslinking agent having two or more capped isocyanate groups that can decap (or deblock) under cure conditions, e.g., at elevated temperature, to form free isocyanate groups and free capping groups. The free isocyanate groups formed by decapping of the crosslinking agent are preferably capable of reacting and forming substantially permanent covalent bonds with the active hydrogen groups of the active hydrogen functional polymer (e.g., with the hydroxy groups of a hydroxy functional polymer).

It is desirable that the capping group of the capped isocyanate crosslinking agent not adversely affect the curable photochromic coating composition upon decapping from the isocyanate (i.e., when it becomes a free capping group). For example, it is desirable that the free capping group neither become trapped in the cured film as gas bubbles nor excessively plasticize the cured film. Capping groups useful in the present invention preferably have the characteristics of being nonfugitive or capable of escaping substantially from the forming coating prior to its vitrification. Typically, the free capping groups escape substantially from the forming (e.g., curing) coating prior to its vitrification.

Classes of capping groups of the capped isocyanate crosslinking agent can be selected from: hydroxy functional compounds, e.g., linear or branched $C_2$-$C_8$ alcohols, ethylene glycol butyl ether, phenol and p-hydroxy methylbenzoate; 1H-azoles, e.g., 1H-1,2,4-triazole and 1H-2,5-dimethylpyrazole; lactams, e.g., $\epsilon$-caprolactam and 2-pyrrolidinone; ketoximes, e.g., 2-propanone oxime and 2-butanone oxime. Other suitable capping groups include, morpholine, 3-aminopropyl morpholine and N-hydroxy phthalimide.

The isocyanate or mixture of isocyanates of the capped isocyanate crosslinking agent has two or more isocyanate groups (e.g., 3 or 4 isocyanate groups). Examples of suitable isocyanates that can be used to prepare the capped isocyanate crosslinking agent include, monomeric diisocyanates, e.g., $\alpha$, $\alpha$'-xylylene diisocyanate, $\alpha$, $\alpha$, $\alpha$', $\alpha$'-tetramethylxylylene diisocyanate and 1-isocyanato-3-isocyanatomethyl-3,5,5-trimethylcyclohexane (isophorone diisocyanate or IPDI), and dimers and trimers of monomeric diisocyanates containing isocyanurate, uretidino, biruet or allophanate linkages, e.g., the trimer of IPDI.

The capped isocyanate crosslinking agent can also be selected from oligomeric capped isocyanate functional adducts. As used herein, by "oligomeric capped polyisocyanate functional adduct" is meant a material that is substantially free of polymeric chain extension. Oligomeric capped polyisocyanate functional adducts can be prepared by art-recognized methods from, for example, a compound containing three or more active hydrogen groups, e.g., trimethylolpropane (TMP), and an isocyanate monomer, e.g., 1-isocyanato- 3,3,5-trimethyl-5-isocyanatomethylcyclohexane (IPDI), in a molar ratio of 1:3, respectively. In the case of TMP and IPDI, by employing art-recognized starved feed and/or dilute solution synthesis techniques, an oligomeric adduct having an average isocyanate functionality of 3 can be prepared (e.g., "TMP-3IPDI"). The three free isocyanate groups per TMP-3IPD1 adduct are then capped with a capping group, e.g., a linear or branched $C_2$-$C_8$ alcohol.

To catalyze the reaction between the isocyanate groups of the capped polyisocyanate crosslinking agent and the hydroxy groups of the hydroxy functional polymer, one or more catalysts are typically present in the curable photochromic coating composition in amounts of from, for example, 0.1 to 5 percent by weight, based on total resin solids of the composition. Classes of useful catalysts include but are not limited to, metal compounds, in particular, organic tin compounds, e.g., tin(II) octanoate and dibutyltin(IV) dilaurate, and tertiary amines, e.g., diazabicyclo[2.2.2]octane.

Curable photochromic coating compositions according to the present invention, which include hydroxy functional polymer and capped isocyanate functional crosslinking agent, typically have present therein hydroxy functional polymer in an amount of from 55 percent to 95 percent by weight, based on total resin solids weight of the composition, e.g., from 75 percent to 90 percent by weight, based on total resin solids weight of the composition. The capped isocyanate functional crosslinking agent is typically present in the curable resin composition in an amount corresponding to the balance of these recited ranges, i.e., 5 to 45, particularly 10 to 25, percent by weight.

With the curable urethane resin compositions of the curable photochromic coating compositions of the present invention, the equivalent ratio of isocyanate equivalents in the capped isocyanate crosslinking agent to hydroxy equivalents in the hydroxy functional polymer is typically within the range of 1:3 to 3:1, e.g., 1:2 to 2:1. While equivalent ratios outside of this range can be employed, they are generally less desirable due to performance deficiencies in cured photochromic films obtained therefrom. Curable photochromic coating compositions according to the present invention that include hydroxy functional polymer and capped isocyanate functional crosslinking agent are typically cured at a temperature of from 120° C. to 190° C. over a period of from 10 to 60 minutes.

Photochromic coating compositions according to the present invention can, with some embodiments, optionally further include a solvent. Examples of suitable solvents include, but art not limited to, acetates, alcohols, ketones, glycols, ethers, aliphatics, cycloaliphatics and aromatics. Examples of acetates include, but are not limited to, ethyl acetate, butyl acetate, and glycol acetate. Examples of ketones include, but are not limited to, methyl ethyl ketone and methyl-N-amyl ketone. Examples of aromatics include, but are not limited to, are toluene, naphthalene and xylene. In an embodiment, one or more solvents are added to each of the first reactant and the second reactant. Suitable solvent blends can include, for example, one or more acetates, propanol and its derivatives, one or more ketones, one or more alcohols and/or one or more aromatics. If present, the solvent is typically present in an amount of from 5 to 60 percent by weight, or 5 to 40 percent by weight, or 10 to 25 percent by weight, based on the total weight of the photochromic coating composition (inclusive of the solvent weight).

Curable photochromic coating compositions according to the present invention can, with some embodiments, optionally contain additives such as waxes for flow and wetting, flow control agents, e.g., poly(2-ethylhexyl)acrylate, adjuvant resin to modify and optimize coating properties, antioxidants and ultraviolet (UV) light absorbers. Examples of useful antioxidants and UV light absorbers include those available commercially from Ciba-Geigy under the trademarks IRGANOX and TINUVIN. These optional additives, when used, are typically present in amounts up to 20 percent by weight (e.g., from 0.5 to 10 percent by weight), based on total weight of resin solids of the curable resin composition.

Photochromic compositions, photochromic articles and photochromic coating compositions according to the present invention can, with some embodiments, further include art-recognized additives that aid or assist in the processing and/or performance of the compositions or articles. Non-limiting examples of such additives include photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, adhesion promoters (such as hexanediol diacrylate and coupling agents), and combinations and mixtures thereof.

The photochromic materials including the indeno-fused naphthopyran compounds according to the present invention can be used in amounts (or ratios) such that the compositions, organic material or substrate (e.g., photochromic articles and photochromic coatings) into which the photochromic materials are incorporated or otherwise connected exhibits desired optical properties. For example, the amount and types of photochromic material can be selected such that the composition, organic material or substrate is clear or colorless when the photochromic compound is in the closed-form (e.g., in the bleached or unactivated state), and can exhibit a desired resultant color when the indeno-fused naphthopyran is in the open-form (e.g., when activated by actinic radiation). The precise amount of the photochromic material that is utilized in the various photochromic compositions and articles described herein is not critical provided that a sufficient amount is used to produce the desired effect. The particular amount of the photochromic material used can depend on a variety of factors, such as but not limited to, the absorption characteristics of the photochromic compound, the color and intensity of the color desired upon activation, and the method used to incorporate or connect the photochromic material to the substrate. Photochromic compositions according to some embodiments of the present invention can include the photochromic material according to the present invention, including the indeno-fused naphthopyran compounds represented by Formulas (I) and/or (II), in an amount of from 0.01 to 40 weight percent, or from 0.05 to 15, or from 0.1 to 5 weight percent, based on the weight of the photochromic composition. For purposes of further non-limiting illustration, the amount of the photochromic material including the indeno-fused naphthopyran compounds represented by Formulas (I) and/or (II) that is incorporated into an organic material can range from 0.01 to 40 weight percent, or from 0.05 to 15, or from 0.1 to 5 weight percent, based on the weight of the organic material.

The present invention is more particularly described in the following examples, which are intended to be illustrative only, since numerous modifications and variations therein will be apparent to those skilled in the art. Unless otherwise specified, all parts and all percentages are by weight.

EXAMPLES

In Part 1 of the Examples, the synthesis procedures used to make photochromic materials according to various non-limiting embodiments disclosed herein are set forth in Examples 1-24 as well as the Comparative Examples (CE) 1-6. In Part 2, the sample preparation, fatigue testing and results for samples individually coated with polyurethane coatings containing Example 1, Example 2, CE-1, CE-2, CE-3, CE-4, CE-5 and CE-6. Part 3 describes the photochromic performance testing and results for Examples 1-24 and CE-1-3.

Example 1

The product of Step 1 of example 12, (7,7-dimethyl-9-phenyl-7H-benzo[c]fluoren-5-ol, 2.0 g), was dissolved in dichloromethane (70 mL) in a 250 mL three-necked flask, followed by addition of p-Toluenesulfonic acid (0.3 g). Then 1-(4-methoxyphenyl)-1-(4-butoxyphenyl)-2-propyn-1-ol (1.6 g) was added to the reaction mixture. The reaction was stirred at room temperature. Two hours later, trifluoroacetic acid (1 mL) was added to the reaction mixture. More, 1-(4-methoxyphenyl)-1-(4-butoxyphenyl)-2-propyn-1-ol (0.15 g), was added to the reaction mixture. The reaction was completed in another two hours. Saturated aqueous $NaHCO_3$ (20 mL) was added to the reaction mixture. It was stirred for 30 minutes. The product was extracted with dichloromethane (2×30 mL). The recovered organic layers were combined, dried over anhydrous $MgSO_4$, and concentrated under vacuum to provide the product (2.9 g). This material was purified by column chromatography (silica gel, 85% hexanes and 15% ethyl acetate as the eluant). The fractions containing product were combined, rotovaped, and dried under vacuum to provide a solid. The solid was then slurried over methanol (20 mL). The product was filtered off and washed with methanol (3×15 mL) to give product (2.3 g). An NMR spectrum showed that the structure was consistent with 3-(4-methoxyphenyl)-3-(4-butoxyphenyl)-1'-phenyl-13,13-dimethyl-3H,13H-indeno[2',3':3,4]naphtho[1,2-b]pyran as shown in the following graphic formula:

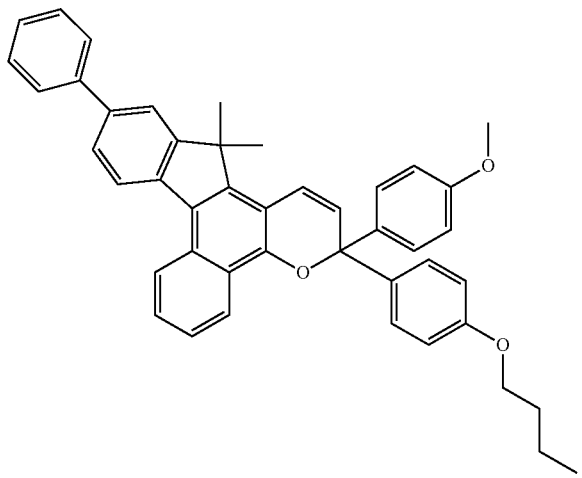 [SMILES: CCCCOc1ccc(C2(c3ccc(OC)cc3)C=Cc3c4c(c5ccccc5c3O2)-c2ccc(-c3ccccc3)cc2C4(C)C)cc1]

Example 2

Step 1
In an oven-dried flask (flask A) placed under a nitrogen atmosphere, a 1.0M solution of 3-methoxyphenylmagnesium bromide in tetrahydrofuran (800 mL) and an additional 300 mL of tetrahydrofuran anhydrous were stirred. The flask was placed in an ice bath and to it was added bis-[2-(N,N-diethylamino)-ethyl)ether (152 mL) slowly drop-wise using an addition funnel over a 45 minute period. The mixture stirred for 1 hour during which time the solution partially solidified. In a separate oven-dried reaction flask (flask B), 4-bromobenzoyl chloride (160 g) was stirred in tetrahydrofuran anhydrous (740 mL). The flask was placed in an ice bath. The contents of flask A was scooped out of it and added to flask B portion-wise over 45 minutes. The reaction mixture was warmed to room temperature and stirred for an additional 2 hours. It was then slowly poured into a beaker containing a saturated aqueous solution of ammonium chloride (1.3 L) and ice. A separatory funnel was used to separate the layers. The resulting aqueous layer was extracted with ethyl acetate (2×600 mL). The recovered organic layers were combined and washed with a saturated aqueous solution of sodium bicarbonate (1 L), dried over sodium sulfate and concentrated by rotary evaporation to yield 231 grams of material containing (4-bromophenyl)(3-methoxyphenyl)methanone which was used in the next reaction as is.

Step 2
In an oven-dried flask placed under a nitrogen atmosphere, the product of Step 1 (90.6 g) and potassium tert-butoxide (56 g) were stirred in toluene (900 mL) using a mechanical stirrer. To this was added dimethyl succinate (70 mL) slowly drop-wise using an addition funnel over a 1 hour period. The exothermic reaction warmed to 40° C. during the dimethyl succinate addition and became more viscous. Additional toluene (400 mL) was added. The reaction mixture was stirred for an additional 2 hours. The reaction mixture was slowly poured into a beaker containing deionized water(1 L) and ice. To this was added concentrated hydrochloric acid until a pH of 1 was reached. A separatory funnel was used to separate the organic and aqueous layers. The resulting aqueous layer was extracted with ethyl acetate (2×600 mL). The recovered organic layers were combined and washed with saturated aqueous solution of sodium chloride (700 mL), dried over sodium sulfate and concentrated by rotary evaporation to yield 150 grams of mixture of (E and Z) 4-(4-bromophenyl)-3-(methoxycarbonyl)-4-(3-methoxyphenyl)but-3-enoic acid which was used in the next reaction as is.

Step 3
In a flask placed under a nitrogen atmosphere, the product of Step 2 (126 g) was stirred in acetic anhydride (500 mL). The reaction mixture was heated to reflux for 3 hours and then cooled to room temperature. It was concentrated by rotary evaporation. During the evaporation process, toluene was added (2×200 mL) to further remove water. The resulting residue was purified by column chromatography on silica gel (1000 g) eluting with a solution of 25% ethyl acetate/75% hexanes. Fractions containing desired product were combined and concentrated by rotary evaporation. The resulting residue was recrystallized in methanol. The crystals were collected by vacuum filtration yielding methyl 4-acetoxy-1-(4-bromophenyl)-7-methoxy-2-naphthoate (23 g).

Step 4
In an oven-dried placed flask under a nitrogen atmosphere, the product of Step 3 (150 g), phenylboronic acid (45 g) and sodium carbonate (85 g) were stirred in 1,2-dimethoxyethane (750 mL) and deionized water (225 mL). A nitrogen purge line was inserted directly into the reaction mixture for 10 minutes. Tetrakis(triphenylphosphine)palladium(0) (10 g) was added and the reaction mixture heated to reflux for 4.5 hours. After cooling to room temperature, the reaction mixture was slowly poured into a beaker containing deionized water (1.5 L) and ice while stirring. Concentrated hydrochloric acid was added until the pH reached 3. A separatory funnel was used to perform chloroform extractions (3×600 mL). The recovered organic layers were combined, washed with a saturated aqueous solution of sodium bicarbonate, dried over sodium sulfate and concentrated by rotary evaporation. The resulting residue was purified by column chromatography on silica gel (400 g) eluting with a solution of 30% ethyl acetate/70% hexanes. Fractions containing product were combined and concentrated by rotary evaporation yielding methyl 1-([1,1'-biphenyl]-4-yl)-4-acetoxy-7-methoxy-2-naphthoate (149 g).

Step 5

In a dried reaction flask placed under nitrogen atmosphere, the product of Step 4 (149 g) was stirred in methanol (1200 mL). To this was added concentrated hydrochloric acid (30 mL). The reaction mixture was heated to reflux for 3 hours. It was then cooled to room temperature and partially concentrated by rotary evaporation. The remaining solution was slowly poured into a beaker containing a saturated aqueous solution of sodium bicarbonate (1200 mL) and ice. A separatory funnel was used to perform extractions with chloroform (3×600 mL). The recovered organic layers were combined, dried over sodium sulfate and concentrated by rotary evaporation. The resulting residue was stirred in a solution of 10% ethyl acetate/90% hexanes. A solid precipitated out. It was collected by vacuum filtration yielding 1-(4-biphenyl)-2-carbomethoxy-4-hydroxy-7-methoxynaphthalene (134 g).

Step 6

In an oven-dried flask placed under a nitrogen atmosphere, the product of Step 5 (134 g) was stirred in anhydrous tetrahydrofuran (1350 mL). The flask was placed in an ice bath and to it was added 3.0M solution of methylmagnesium chloride in tetrahydrofuran (530 mL) slowly drop-wise using an addition funnel over a 40 minute period. The ice bath was removed and the reaction mixture heated to 40° C. for 2 hours. After cooling to room temperature, the reaction mixture was slowly poured into a saturated aqueous solution of ammonium chloride (1.5 L) and ice while stirring. A separatory funnel was used to separate the layers. The resulting aqueous layer was extracted with ethyl acetate (2×700 mL). The recovered organic layers were combined and washed with a saturated aqueous solution of sodium bicarbonate (1 L), dried over sodium sulfate and concentrated by rotary evaporation yielding a residue containing 4-([1,1'-biphenyl]-4-yl)-3-(2-hydroxypropan-2-yl)-6-methoxynaphthalen-1-ol (134 g) which was used in the next reaction as is.

Step 7

In an oven-dried flask placed under a nitrogen atmosphere and equipped with a Dean-Stark trap, the product of Step 6 (134 g) was stirred in xylenes (1350 mL). To this was added p-toluenesulfonic acid (6.7 g). The reaction mixture was heated to reflux for 2 hours. After cooling to room temperature, the reaction mixture was added directly to a chromatography column of silica gel (1000 g). It was eluted with a solution of 30% ethyl acetate/70% hexanes. Fractions containing product were combined and concentrated by rotary evaporation to yield a solid. The solid was slurried in a solution of 10% ethyl acetate/90% hexanes and collected by vacuum filtration yielding 47 g of 2-methoxy-7,7-dimethyl-9-phenyl-7H-benzo[C]fluoren-5-ol.

Step 8

In an oven-dried flask placed under a nitrogen atmosphere, the product of Step 7 (19 g) and 1-(4-butoxyphenyl)-1-(4-methoxyphenyl)-2-propyn-1-ol (20.9 g) prepared according to the procedure of Step 1 of Example 5 of U.S. Pat. No. 7,465,415B2 except that (4-butoxyphenyl)(4-methoxyphenyl)methanone used in place of (4-fluorophenyl)(4-(2-hydroxyethoxy)phenyl)methanone, which procedure is incorporated herein by reference, were stirred in chloroform (190 mL). To this was added p-toluenesulfonic acid (990 mg). The reaction mixture was stirred at room temperature for 2 hours. It was transferred to a separatory funnel and washed with a saturated aqueous solution of sodium bicarbonate (150 mL). The recovered organic layer was dried over sodium sulfate and concentrated by rotary evaporation. The resulting residue was purified by column chromatography on silica gel (400 g) eluting with a solution of 20% ethyl acetate/80% hexanes. Fractions containing product were combined and concentrated by rotary evaporation. The resulting residue was recrystallized in diethyl ether. The crystals were collected by vacuum filtration yielding 7.3 grams of product. An NMR spectrum showed the product to have a structure consistent with 3-(4-butoxyphenyl)-3-(4-methoxyphenyl)-7-methoxy-1'-phenyl-13,13-dimethyl-3H,13H-indeno[2',3':3,4]naphtho[1,2-b]pyran as shown in the following graphic formula:

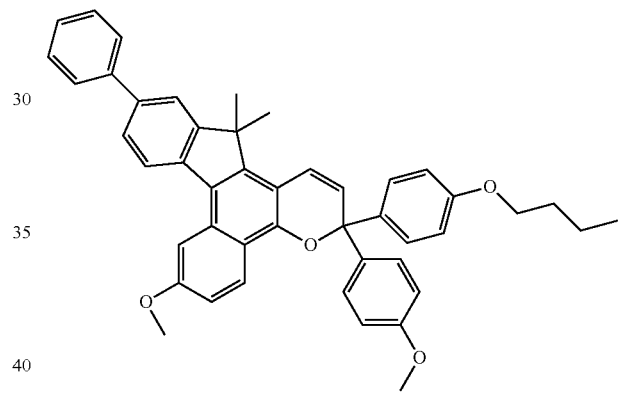

Example 3

The product of Step 2 of Example 4 (2-methoxy-9-phenyl-7,7-dimethyl-5-hydroxy-7H-benzo[C]fluorene, 2.0 grams), 1,1-di(4-methoxyphenyl)-2-propyn-1-ol (2.0 grams, the product of Step 1 of Example 1 of U.S. Pat. No. 5,458,814, which example is hereby specifically incorporated by reference herein, and 100 mL of chloroform were combined in a reaction flask and stirred at 40° C. Sufficient dodecylbenzenesulfonic acid was added (3-5 drops) to produce a deep black coloration to the solution. After two hours, the reaction mixture was cooled and washed with 100 mL of water. The organic layer was separated, dried over sodium sulfate, and concentrated by rotary evaporation to yield a dark oil. Methanol (100mL) was added to the product. Upon warming and stirring, the product readily crystallized. The crystals were filtered, washed with fresh methanol and dried to yield 1.5 grams of an off-white solid. An NMR spectrum showed the product to have a structure consistent with 3,3-bis-(4-methoxyphenyl)-7-methoxy-11-phenyl-13,13-dimethyl-3H,13H-indeno[2',3':3,4]naphtho[1,2-b]pyran as shown in the following graphic formula:

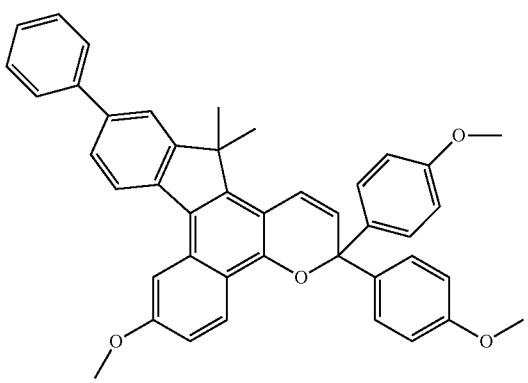 [SMILES: COc1ccc(C2(c3ccc(OC)cc3)C=Cc3c4c(c5cc(OC)ccc5c3O2)-c2ccc(-c3ccccc3)cc2C4(C)C)cc1]

Example 4

Step 1

The product of Step 5 of Example 2,1-(4-biphenyl)-2-carbomethoxy-4-hydroxy-7-methoxynaphthalene (8.6 g) and dry tetrahydrofuran (THF, 45 mL) were combined in a 100 mL reaction flask. This mixture was added dropwise over a 30 minute period to a 500 mL reaction flask containing 112.6 mL of ethylmagnesium chloride (2.0 M in diethyl ether) while the mixture was stirred under a nitrogen atmosphere at room temperature. The resulting mixture was stirred at room temperature overnight. Then reaction mixture was poured dropwise into 400 mL of water. The resulting solution was neutralized with concentrate hydrochloric acid and extracted with ethyl acetate (three times with 200 mL). The combined organic layers were washed with saturated NaCl solution and then dried over anhydrous sodium sulfate. The solvent was removed by rotary evaporator and dried under vacuum to yield 8.25 grams of a yellow solid as 1-(4-biphenyl)-2-(1-hydroxy-1-ethyl)-propyl)-4-hydroxy-7-methoxynaphthalene.

Step 2

The product of Step 1 (8.6 g) from Step 1, p-toluenesulfonic acid (PTSA) (0.5 g) and xylenes (200 mL) were combined in a 500 mL reaction flask equipped with a Dean-Stark trap. This mixture was heated to reflux temperatures under a nitrogen atmosphere and stirred overnight at reflux temperatures. The reaction mixture was cooled to room temperature and the solvent was removed by rotary evaporator under reduced pressure. The resulting dark oil was dried under vacuum. This material contained 2-methoxy-9-phenyl-7,7-diethyl-7H-benzo[C]fluoren-5-ol and was used in the next step as is.

Step 3

Into a 1 liter reaction flask was added methylene chloride (500 mL), dihydroxybenzophenone (107 g) and 3,4-dihydro-2H-pyran (DHP, 105 g). The resulting mixture was cooled to about 5° C. in an ice bath. Pyridine p-toluenesulfonate (PPTS) (1.0 g) was added and the reaction mixture was stirred 1.5 hours at 5° C. Triethylamine (1.0 g) was added and the mixture was stirred for an additional 10 min. The resulting mixture was filtered through basic alumina and concentrated to 219 g of residue by rotary evaporation. Heptanes (250 mL) were added, and the product solidified. The solid was isolated, washed with 200 mL heptanes and dried under vacuum to provide 175 g of the product bis(4-((tetrahydro-2H-pyran-2-yl)oxy)phenyl)methanone.

Step 4

The product of Step 3 (153 g) was added to a 1 L reaction flask with 230 mL dimethyl formamide (DMF). The mixture was cooled to 1° C. and was bubbled with acetylene gas for 20 min. A slurry of sodium acetylide (18% by weight in xylene/mineral oil from Aldrich, 215 g) was added all at once at 3° C. A brief exotherm to 11° C. was observed. After the reaction mixture was stirred in ice for 3.5 hrs, a 10 weight percent solution of NaCl was carefully added. During the phase separation, toluene (150 mL) was added. The recovered organic layer was washed with a 10 weight percent solution of NaCl (2 times with 145 mL each time). The resulting solution was filtered through a small alumina plug. The filtrate was concentrated by rotary evaporation to provide 227.5 g of product. NMR analysis showed the product to have a structure consistent with 1,1-bis-[4-((ditetrahydro-2H-pyran-2-yl)oxy)phenyl]-2-propyn-1-ol.

Step 5

The product of Step 2 (2.0 g) and methylene chloride (100 mL) were combined in a 250 mL reaction flask. To this was added PTSA (0.25 grams) and the mixture was stirred at room temperature under a nitrogen atmosphere. The product of Step 4 (2.3 g) was added over a 15 minute period. The reaction mixture was stirred for 2 hours at room temperature under a nitrogen atmosphere. Added another 1.43 grams of the product of Step 4 over a 30 minute period, and the reaction mixture was stirred overnight at room temperature under a nitrogen atmosphere. Added 20 mL of methanol and 0.2 grams of PTSA to the reaction mixture and stirred for 2 hours to remove the tetrahydropyran (THP) protecting groups. The reaction mixture was washed with 2×200 mL of saturated aqueous NaHCO$_3$. The recovered organic layers were dried over anhydrous sodium sulfate. The solvent was removed by rotary evaporation to yield a purplish solid. This material was purified by column chromatography, and the pure fractions were combined and rotavaped to obtain a purplish oily solid (0.75 grams). This solid was slurried in chloroform, and was collected by vacuum filtration to obtain an off white solid. NMR and Mass Spec analysis showed the solid product to have a structure consistent with 3,3-bis-(4-hydroxyphenyl)-7-methoxy-1'-phenyl-13,13-diethyl-3H,13H-indeno[2',3':3,4]naphtho[1,2-b]pyran as shown in the following graphic formula:

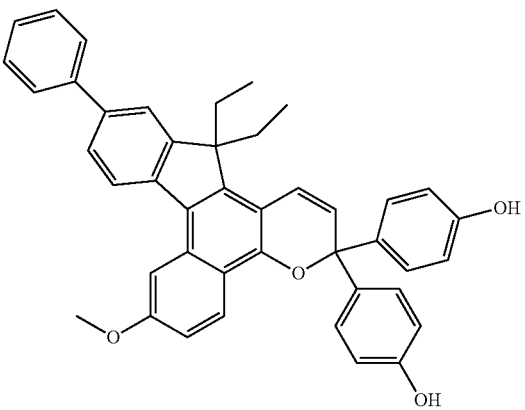 [SMILES: CCC1(CC)c2cc(-c3ccccc3)ccc2-c2c1c1c(c3ccc(OC)cc23)OC(c2ccc(O)cc2)(c2ccc(O)cc2)C=C1]

Example 5

Step 1

To a reaction flask containing a pyridine (13 mL) solution of 7,7-dimethyl-7H-benzo[c]fluoren-5-ol (3.5 g, 13 mmol)

was added a solution of trifluoromethanesulfonic anhydride (7.2 g, 26 mmol) in CH$_2$Cl$_2$ (10 mL) dropwise at 0° C. over a 15 min period. The reaction mixture was stirred at room temperature for 2 h. After removal of the solvent, the residue was poured into water and extracted with ether. The ether extract was evaporated to give product 5.28 g.

Step 2

Iodine monobromide (2.1 g) in glacial acetic acid (8 mL) was added into a reaction flask containing a solution of 3.37 g. of the product of Step 1 in 15 mL of glacial acetic acid which was kept cool in an ice-water bath. The reaction was allowed to stand for one hour during which time as much hydrogen bromide as possible was removed from the flask by gentle aeration. The mixture was poured into 2 wt % sodium bisulfite solution (50 mL). A saturated sodium bicarbonate suspension solution was then added and the solution was exacted with CH$_2$Cl$_2$, The product was obtained after the removal of solvent and was used directly in the next step.

Step 3

To a reaction flask containing the product obtained from Step 2 was added ethanol (25 mL) and NaOH (1.1 g, 26 mmol). The mixture was refluxed for 6 hours. Ethanol was removed by vacuum evaporation and then a saturated sodium bicarbonate suspension was then added and the resulting mixture was extracted with ethyl acetate. The recovered product (1.8 g) contained 7,7-dimethyl-9-bromo-7H-benzo[C] fluoren-5-ol and was used directly in the next step.

Step 4

The product of Step 3 (0.5 g), 2,4-dimethoxyphenylboronic acid (5.0 g), sodium carbonate (8.7 g), ethylene glycol dimethyl ether (100 mL), and water (100 mL) were combined in a reaction flask under a nitrogen atmosphere and stirred for 1 hour at room temperature. The mixture was then heated to reflux temperature for 24 hours. The reaction mixture was cooled to room temperature and poured into water (200 mL) and extracted with ethyl acetate (three times with 200 mL). The organic extracts were combined and the solvent was removed by rotary evaporation to give 7.3 g of a light yellow solid. NMR spectra showed the product to have a structure consistent with 7,7-dimethyl-9-(2,4-dimethoxyphenyl)-7H-benzo[C]fluoren-5-ol.

Step 5

The product of Step 4 (2.0 g), 1,1-bis-(4-methoxyphenyl)-2-propyn-1-ol (1.6 g, the product of Example 1, Step 1 of U.S. Pat. No. 5,458,814, which example is hereby specifically incorporated by reference herein), dodecylbenzene sulfonic acid (0.2 g) and chloroform (preserved with pentene, 250 mL) were combined in a reaction flask and stirred at room temperature for 5 hours. The reaction mixture was washed with 50% saturated aqueous NaHCO$_3$ (200 mL) and the recovered organic layer was dried over anhydrous Na$_2$SO$_4$. The solvent was removed by rotary evaporation. Hot methanol was added to the resulting residue and the solution cooled to room temperature. The resulting precipitate was collected by vacuum filtration and washed with cold methanol yielding 1.7 g of product. NMR spectra showed the product to have a structure consistent with 3,3-bis-(4-methoxyphenyl)-11-(2,4-dimethoxyphenyl)-13,13-dimethyl-3H,13H-indeno[2',3':3, 4]-naphtho[1,2-b]pyran as shown in the following graphic formula:

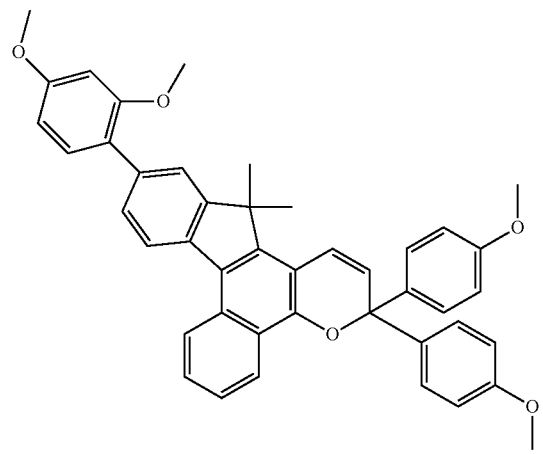 [SMILES: COc1ccc(C2(c3ccc(OC)cc3)C=Cc3c4c(c5ccccc5c3O2)-c2ccc(-c3ccc(OC)cc3OC)cc2C4(C)C)cc1]

Example 6

Step 1

To a 1 L single-neck flask was added 3-methoxyphenyl-magnesium bromide in tetrahydrofuran (1M, 560 mL). The flask was set up with a N$_2$ blanket and magnetic stirring. The flask was seated in ice-salt-water bath (−5 to −8° C.). 1,2-Dimethylamino ethyl ether (106 mL) in tetrahydrofuran (100 mL) was dropped to the flask through an addition funnel over 10 minutes. The mixture was stirred for 1 hour. 4-Bromobenzoyl chloride in tetrahydrofuran (122 g in 100 mL) suspension was dropped into the flask using an addition funnel over 20 minutes. The cooling bath was removed 1 hour after the addition. The mixture was stirred at room temperature for 20 hours. The solution was poured into brine (1 L). Conc. hydrochloric acid (250 mL) was added to the mixture slowly. The top layer was separated and filtered through magnesium sulfate. The solution was concentrated to initially yield an orange-red oily residue (182 g) that became a yellow waxy product. The residue was dried under high vacuum and used as is in next step.

Step 2

The crude product from Step 1 (182 gram) was dissolved in toluene (1 L) in a 2 L single three-neck RB flask with N$_2$ blanket and overhead stirring. Dimethyl succinate (72 mL) was added to the same flask. Potassium t-butoxide (68 gram) was added to the mixture in portions over 20 minutes. The reaction mixture was stirred at room temperature for 20 hours. The dark slurry was poured into cold water (400 mL). The bottom water layer was separated and acidified by conc. HCl (200 mL). The slurry was extracted with ethyl acetate twice (500 mL and 300 mL). The top solution was dried over sodium sulfate and concentrated. The residue was dried under high vacuum (170 g) and used as is in next step.

Step 3

The oily product from Step 2 (170 gram) and trace amount of 4-dimethylaminopyridine (0.2 gram) were dissolved in acetic anhydride (250 mL) in 1 L single-neck RB flask equipped with a water condenser and magnetic stirring under N$_2$ blanket. The reaction mixture was heated to 120° C. for 3 hours. The mixture was then condensed down to less volume under reduced pressure. The recovered oily residue was dissolved in methanol. Solid product crystallized out and was collected by filtration (80 grams). NMR analysis showed the product to have a structure consistent with methyl 4-acetoxy-1-(4-bromophenyl)-7-methoxy-2-naphthoate.

Step 4

To a 1 L single-neck flask was added part of the product of Step 3 (63 g), phenylboronic acid (21 g), potassium carbonate (100 g), toluene (240 mL), ethanol (120 mL) and water (120 mL). The mixture was bubbled with $N_2$ for 15 minutes. Tetrakis(triphenylphosphine)palladium(0) (1.5 g) was added to the mixture. The reaction mixture was heated to reflux for 4.5 hours. The mixture was cooled to room temperature and poured into water (500 mL). The resulting mixture was acidified with concentrated hydrochloric acid (200 mL). The top organic layer was filtered through magnesium sulfate and then concentrated. Solid product was obtained from the solution. The mother liquor was filtered through a short silica gel plug. Solid product was obtained from the major fraction. The combined product (64 g) was dried in vacuum oven.

Step 5

To a 3 L one-neck RB flask was added dry solid lanthanum (III) chloride (130 g), lithium chloride (37 g), the product from Step 4 (60 g) and anhydrous THF (1.5 L). The white slurry was stirred at room temperature for 20 hours. The flask was cooled in a dry ice/acetone bath. N-Propylmagnesium chloride in diethyl ether solution (2M, 425 mL) was dropped into the mixture slowly. The cooling bath was removed upon completing the addition. The reaction mixture was stirred for 3 hours. The mixture was poured into cold 30% aqueous hydrochloric acid (500 mL) and ice. The recovered top layer was filtered over magnesium sulfate and then concentrated. The resulting oily product (74g) was used as is in the next step.

Step 6

The product from Step 5 was dissolved in xylene (400 mL) in a 2 L single-neck flask equipped with Dean-Stark trap and water condenser. Bismuth trifluoromethanesulfonate (1.6 g) was added to the flask. The reaction mixture was heated to reflux for 4 hours. The resulting mixture was cooled to room temperature and filtered through a silica gel plug. The major fraction was collected and condensed to less volume. Solid product (65 g) was recrystallized out from t-butyl methyl ether/hexane solution to yield an off-white solid product. NMR analysis showed the product to have a structure consistent with 9-phenyl-2-methoxy-7,7-dipropyl-7H-benzo[c]fluoren-5-ol.

Step 7

The product from Step 6 (5 g), p-toluenesulfonic acid (1 g) and 1-(4-methoxyphenyl)-1-(4-butoxyphenyl)prop-2-yn-1-ol (4 g) were dissolved in 1,2-dichloroethane (40 mL) in a 250 mL single-neck flask. The mixture was heated to 80° C. for 1 hour. The mixture was cooled to room temperature and filtered through a short silica gel plug. The major fraction was further purified by silica gel chromatography eluting with ethyl acetate/hexanes to afford an oily product. Solid product (6 g) was obtained by precipitation of the oily product in methanol. NMR analysis indicated that the product had a structure consistent with 3-(4-butoxyphenyl)-3-(4-methoxyphenyl)-7-methoxy-1'-phenyl-13,13-dipropyl-3H,13H-indeno[2',3':3,4]naphtho[1,2-b]pyran shown in the following graphic formula:

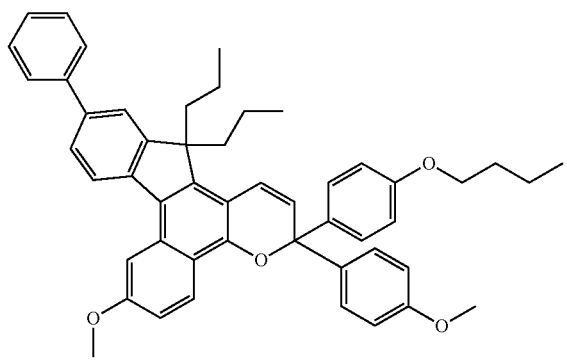 [SMILES: CCCCOc1ccc(C2(c3ccc(OC)cc3)C=Cc3c4c(c5cc(OC)ccc5c3O2)-c2ccc(-c3ccccc3)cc2C4(CCC)CCC)cc1]

Example 7

Step 1

To a 250 mL two neck flask was added benzyl (1.5 g), ammonium acetate (25.7 g), and (4-formylphenyl)boronic acid (1.0 g) in acetic acid (150 mL). The resulting mixture was gently refluxed for 24 hours then allowed to cool to room temperature. The white slurry that precipitated by the neutralization with aqueous $NH_3$ was filtered off. The slurry was dissolved in diethyl ether and the solution was washed with brine then dried over sodium sulfate. The solvent was removed by rotary evaporator to give 2.0 g of a white solid. NMR spectra showed the product to have a structure consistent with (4-(4,5-diphenyl-1H-imidazol-2-yl)phenyl)boronic acid.

Step 2

The product of Step 3 of Example 5 (7,7-dimethyl-9-bromo-7H-benzo[C]fluoren-5-ol (30.0 g)), 1,1-bis-(4-methoxyphenyl)-2-propyn-1-ol (35.6 g), dodecylbenzene sulfonic acid (1.0 g) and chloroform (preserved with pentene, 250 mL) were combined in a reaction flask and stirred at room temperature for 5 hours. The reaction mixture was washed with 50% saturated aqueous $NaHCO_3$ (200 mL) and the recovered organic layer was dried over anhydrous $Na_2SO_4$. The solvent was removed by rotary evaporation. Hot methanol was added to the resulting residue and the solution cooled to room temperature. The resulting precipitate was collected by vacuum filtration and washed with cold methanol yielding 51.2 g of 3,3-bis-(4-methoxyphenyl)-11-bromo-13,13-dimethyl-3H,13H-indeno[2',3':3,4]naphtho[1,2-b]pyran.

Step 3

The product of Step 2 (3.0 g) tetrakis(triphenylphosphine) palladium (0.5 g), the product of Step 1 (1.9 g), potassium carbonate (2.1 g), ethylene glycol dimethyl ether (60 mL), and water (60 mL) were combined in a reaction flask under a nitrogen atmosphere and stirred for 1 hour at room temperature. The mixture was then heated to reflux temperature for 24 hours. The reaction mixture was cooled to room temperature and poured into water (200 mL) and extracted with ethyl acetate (three times with 200 mL). The recovered organic extracts were combined and the solvent was removed by rotary evaporator to give 3.4 g of a light yellow solid. NMR spectra showed the product to have a structure consistent with 3,3-bis-(4-methoxyphenyl)-11-(4-(4,5-diphenyl-1H-imidazol-2-yl)phenyl)-13,13-dimethyl-3H,13H-indeno[2',3':3,4]naphtho[1,2-b]pyran as shown in the following graphic formula:

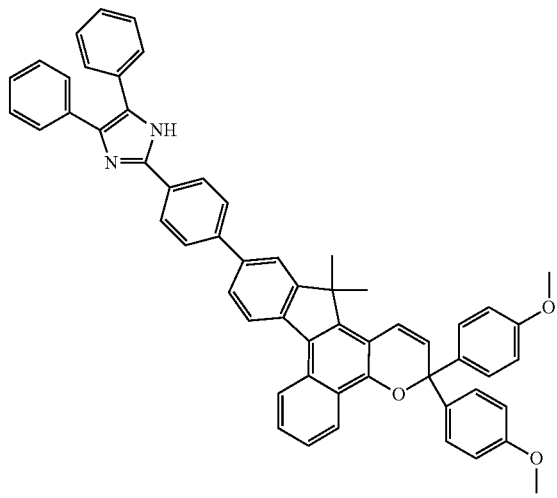 [SMILES: COc1ccc(C2(c3ccc(OC)cc3)C=Cc3c4c(c5ccccc5c3O2)-c2ccc(-c3ccc(-c5nc(-c6ccccc6)c(-c6ccccc6)[nH]5)cc3)cc2C4(C)C)cc1]

Example 8

Step 1

In an oven-dried flask (flask A) placed under a nitrogen atmosphere, a 1.0M solution of 3-methoxyphenylmagnesium bromide in tetrahydrofuran (800 mL) and an additional 300 mL of tetrahydrofuran anhydrous were stirred. The flask was placed in an ice bath and to it was added bis-[2-(N,N-diethylamino)-ethyl)ether (152 mL) slowly drop-wise using an addition funnel over a 45 minute period. The mixture stirred for 1 hour during which time the solution partially solidified. In a separate oven-dried reaction flask (flask B), 4-bromobenzoyl chloride (160 g) was stirred in tetrahydrofuran anhydrous (740 mL). The flask was placed in an ice bath. The contents of flask A was scooped out and added to flask B portion-wise over 45 minutes. The reaction mixture was warmed to room temperature and stirred for an additional 2 hours. It was then slowly poured into a beaker containing a saturated aqueous solution of ammonium chloride (1.3 L) and ice. A separatory funnel was used to separate the layers. The aqueous layer was recovered and extracted with ethyl acetate (2×600 mL each time). The recovered organic layers were combined and washed with a saturated aqueous solution of sodium bicarbonate (1 L), dried over sodium sulfate and concentrated by rotary evaporation to yield 231 grams of (4-bromophenyl)(3-methoxyphenyl)methanone which was used in the next reaction as is.

Step 2

In an oven-dried flask placed under a nitrogen atmosphere, the product of Step 1 (90.6 g) and potassium tert-butoxide (56 g) were stirred in toluene (900 mL) using a mechanical stirrer. To this was added dimethyl succinate (70 mL) slowly drop-wise using an addition funnel over a 1 hour period. The exothermic reaction warmed to 40° C. during the dimethyl succinate addition and became more viscous. Additional toluene (400 mL) was added. The reaction mixture was stirred for an additional 2 hours. The reaction mixture was slowly poured into a beaker containing deionized water (1 L) and ice. To this was added concentrated hydrochloric acid until a pH of 1 was reached. A separatory funnel was used to separate the organic and aqueous layers. The aqueous layer was extracted with ethyl acetate (2×600 mL each time). The organic layers were recovered, combined and washed with saturated aqueous solution of sodium chloride (700 mL), dried over sodium sulfate and concentrated by rotary evaporation to yield 150 grams of mixture of (E and Z) 4-(4-bromophenyl)-3-(methoxycarbonyl)-4-(3-methoxyphenyl)but-3-enoic acid which was used in the next reaction as is.

Step 3

In a flask placed under a nitrogen atmosphere, the product of Step 3 (126 g) was stirred in acetic anhydride (500 mL). The reaction mixture was heated to reflux for 3 hours and then cooled to room temperature. It was concentrated by rotary evaporation and toluene was added (2×200 mL) and evaporated to remove additional water. The resulting residue was purified by column chromatography on silica gel (1000 g) eluting with a solution of 25% ethyl acetate/75% hexanes. Fractions containing desired product were combined and concentrated by rotary evaporation. The resulting residue was recrystallized in methanol. The crystals were collected by vacuum filtration. Methyl 4-acetoxy-1-(4-bromophenyl)-7-methoxy-2-naphthoate (23 g) was isolated. This step was repeated to produce additional product for the next step.

Step 4

In an oven-dried flask placed under a nitrogen atmosphere, the product of Step 3 (25 g), 2,4-dimethoxyphenylboronic acid (11.1 g) and sodium carbonate (14.2 g) were stirred in 1,2-dimethoxyethane (125 mL) and deionized water (40 mL). A nitrogen purge line was inserted directly into the reaction mixture for 10 minutes and then removed. Tetrakis(triphenylphosphine)palladium(0) (1.4 g) was added to the reaction mixture. It was heated to reflux for 4 hours. After cooling to room temperature, the reaction mixture was poured into a beaker containing deionized water (1 L) and ice. Concentrated hydrochloric acid was added while stirring vigorously until the pH reached 3. The mixture was transferred to a separatory funnel and extracted with chloroform (3×400 mL each time). The organic layers were recovered, combined and then placed directly onto a silica gel column (600 g) eluting with a mixture of 30% ethyl acetate/70% hexanes. Fractions containing product were combined and concentrated by rotary evaporation. The resulting residue was slurried in a minimal amount of a mixture of 10% ethyl acetate/90% hexanes. A solid precipitate was collected by vacuum filtration which was 25.4 grams of methyl 4-acetoxy-1-(2',4'-dimethoxy-[1,1'-biphenyl]-4-yl)-7-methoxy-2-naphthoate.

Step 5

Lanthanum(III) chloride (44.2 g) and lithium chloride (13.2 g) were added to a reaction flask. The flask was placed in vacuum oven at 170° C. for 4 hours. It was then removed from the oven and immediately placed under a nitrogen atmosphere. The product of Step 4 (25.3 g) was charged to the reaction flask and the mixture stirred in tetrahydrofuran anhydrous (500 mL). The reaction flask was cooled in a dry ice/acetone bath. To it was added a 2M solution of propylmagnesium chloride in diethyl ether (155 mL) slowly drop-wise using an addition funnel over the course of 40 minutes. The reaction mixture was heated to 40° C. for 3 hours. It was then cooled to room temperature and slowly poured into a beaker containing deionized water (1 L) and ice. Concentrated hydrochloric acid was added to the mixture while stirring vigorously until the pH reached 3. The mixture was transferred to a separatory funnel and the organic layer and aqueous layer were separated. The aqueous layer was recovered, extracted with ethyl acetate (2×350 mL each time). The organic layers were recovered, combined and washed with a saturated aqueous solution of sodium bicarbonate (500 mL), dried over sodium sulfate and concentrated by rotary evaporation. The resulting residue was purified by a chromatography column of silica gel (200 g) eluting with a mixture of 50% ethyl acetate/50% hexanes. Fractions containing product were combined and concentrated by rotary evaporation. The resulting residue weighed 26 grams and contained 4-(2',4'-dimethoxy-[1,1'-biphenyl]-4-yl)-3-(4-hydroxyheptan-4-yl)-6-methoxynaphthalen-1-ol and was used in the next reaction as is.

Step 6

In an oven-dried flask placed under a nitrogen atmosphere and equipped with a Dean-Stark trap, the product of Step 5 (26 g) was stirred in xylenes (520 mL). To this was added bismuth (III) trifluoromethanesulfonate (3.4 g) and then the reaction mixture was heated to reflux for 3 hours. After cooling to room temperature the reaction mixture was added directly to a column of silica gel (400 g). It was eluted with a mixture of 60% ethyl acetate/40% hexanes. Fractions containing product were combined and concentrated by rotary evaporation. The resulting residue was further purified with a second chromatography column of silica gel that was identical in conditions used to the first column. Fractions containing product were combined and concentrated by rotary evaporation. The resulting residue weighed 3.6 grams and was 2-methoxy-7,7-dipropyl-9-(2,4-dimethoxyphenyl)-7H-benzo[C]fluoren-5-ol.

Step 7

The product of Step 6 (3.4 grams) and methylene chloride (125 mL) were combined in a 250 mL reaction flask. To this was added 0.21 grams of PTSA and the mixture was stirred at room temperature under a nitrogen atmosphere. 2.4 grams of 1-(4-methoxyphenyl)-1-(4-butoxyphenyl)-2-propyn-1-ol was added over a 5 minute period. The reaction mixture was stirred for 90 minutes at room temperature under a nitrogen atmosphere. The reaction mixture was washed with 2×200 mL of saturated aqueous NaHCO₃. The organic layer was dried over anhydrous sodium sulfate. The solvent was removed by rotary evaporation to yield a purplish solid. This material was purified by column chromatography. The pure fractions were combined and concentrated by rotary evaporation to obtain 1.2 grams of a purplish solid. This solid was crystallized from a 1:1 mixture of diethyl ether and hexane to obtain 0.7 grams of an off-white solid. NMR analysis showed the solid product to have a structure consistent with 3-(4-butoxyphenyl)-3-(4-methoxyphenyl)-7-methoxy-11-(2,4-dimethoxyphenyl)-13,13-dipropyl-3H,13H-indeno[2',3':3,4]naphtho[1,2-b]pyran as shown in the following graphic formula:

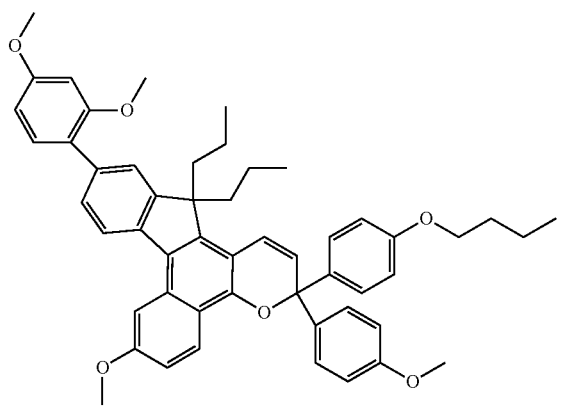 [SMILES: CCCCOc1ccc(C2(c3ccc(OC)cc3)C=Cc3c4c(c5cc(OC)ccc5c3O2)-c2ccc(-c3ccc(OC)cc3OC)cc2C4(CCC)CCC)cc1]

Example 9

Step 1

The product of Step 5 of Example 2 (1-(4-biphenyl)-2-carbomethoxy-4-hydroxy-7-methoxynaphthalene (30.0 g)) was added to a reaction flask containing 150 mL of a 10 weight percent aqueous sodium hydroxide solution and 50 mL of methanol. The mixture was refluxed for one hour, cooled, then slowly poured into a beaker containing approximately one liter of cold dilute hydrochloric acid. About 24 g of the resulting crystalline product, 1-(4-biphenyl)-4-hydroxy-7-methoxy-2-naphthoic acid was collected by vacuum filtration.

Step 2

To a 250 mL two neck flask was added the product of Step 1 (20.0 g) and acetic anhydride (150 mL). The mixture was heated to reflux temperature for 24 hours. After cooling down the reaction mixture to room temperature, added 20.0 g of sulfuric acid drop by drop while keeping the temperature below 80° C. After completion of addition of sulfuric acid, heated the mixture to 60° C. and stirred for one hour. Then the reaction mixture was poured into water (300 mL). The resulting precipitate was collected by vacuum filtration and washed with diethyl ether yielding 19.0 g of 2-methoxy-7-oxo-9-phenyl-7H-benzo[c]fluoren-5-yl acetate.

Step 3

The product of Step 2 (15.0 g) was added to a reaction flask containing 150 mL of methanol. Two mL of concentrated hydrochloric acid was added and the mixture was heated to reflux temperature. After approximately four hours, the volume of the mixture was reduced by half on a rotary evaporator. As the mixture cooled, the product started to crystallized. The resulting crystals were filtered and washed with methanol yielding 10.2 g of 5-hydroxy-2-methoxy-9-phenyl-7H-benzo[c]fluoren-7-one.

Step 4

To a solution of the product of Step 3, (10.0 g) in 50 mL of diethylene glycol, added 8.0 g of potassium hydroxide and 10 mL of hydrazine hydrate. After refluxing for one and half hours, the water was drained from the condenser and the temperature allowed to rise to 190° C. for four hours. After cooling down the mixture to room temperature, it was diluted with 300 mL of water and slowly poured into 5 weight percent aqueous hydrochloric acid (200 mL). A solid precipitated and was filtered and dried under reduced pressure yielding 7.3 g of 2-methoxy-9-phenyl-7H-benzo[c]fluoren-5-ol. This step was repeated to produce additional product for the next step.

Step 5

A solution of n-butyl lithium (n-BuLi) (2.5M, 47.2 mL) in hexane was added into 500 mL two neck flask which contained 10.0 g of the product of Step 4 in diethyl ether (200 mL). The mixture was refluxed for five hours, cooled to room temperature, and poured rapidly onto crushed dry-ice. When the temperature of reaction mixture reached room temperature, ethyl acetate (150 mL) was added and the resulting mixture was acidified by concentrated hydrochloric acid. The organic layer was recovered and dried over sodium sulfate. After removing the solvent, 9.4 g of 5-hydroxy-2-methoxy-9-phenyl-7H-benzo[c]fluorene-7-carboxylic acid was obtained as a white solid. This step was repeated to produce additional product for the next step.

Step 6

To a 250 mL two neck flask was added the product of Step 5 (16.0 g), two mL of hydrochloric acid, and 150 mL of methanol. The heterogeneous mixture was refluxed for five hours. This time the reaction mixture was changed into homogeneous phase. After removing the solvent under reduced pressure, white solid formed. The white solid was washed with methylene chloride/hexan at a 30/70 v/v. Nuclear magnetic resonance spectra showed the product to have a structure consistent with methyl-5-hydroxy-2-methoxy-9-phenyl-7H-benzo[c]fluorene-7-carboxylate.

Step 7

The product of Step 6 (5.0 g), 1,1-bis-(4-methoxyphenyl)-2-propyn-1-ol (5.1 g), dodecylbenzene sulfonic acid (0.3 g) and chloroform (preserved with pentene, 150 mL) were combined in a reaction flask and stirred at room temperature for 5 hours. The reaction mixture was washed with 50% saturated aqueous $NaHCO_3$ (200 mL) and the recovered organic layer was dried over anhydrous $Na_2SO_4$. The solvent was removed by rotary evaporation. Hot methanol was added to the resulting residue and the solution cooled to room temperature. The resulting precipitate was collected by vacuum filtration and washed with cold methanol yielding 7.1 g of 3,3-bis-(4-methoxyphenyl)-7-methoxy-11-phenyl-13-carbomethoxy-3H,13H-indeno[2',3':3,4]naphtho[1,2-b]pyran.

Step 8

To a 250 mL two neck flask was added the product of Step 7 (5.0 g), potassium carbonate (5.4 g), methyliodide (5.5 g), and acetone (150 mL). The mixture was refluxed for overnight. The resulting mixture was filtered and solvent was removed under reduced pressure. The product was purified by column chromatography in ethyl acetate/hexane at a ratio of 20/80 v/v. Nuclear magnetic resonance spectra showed the product to have a structure consistent with 3,3-bis-(4-methoxyphenyl)-7-methoxy-11-phenyl-13-carbomethoxy-13-methyl-3H,13H-indeno[2',3':3,4]naphtho[1,2-b]pyran as shown in the following graphic formula:

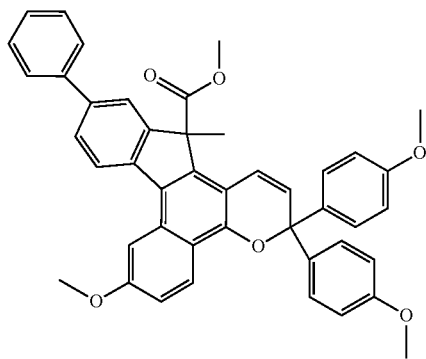 [SMILES: COC(=O)C1(C)c2cc(-c3ccccc3)ccc2-c2c1c1c(c3ccc(OC)cc23)OC(c2ccc(OC)cc2)(c2ccc(OC)cc2)C=C1]

Example 10

Step 1

To a 1 L single-neck flask was added 3-methoxyphenylmagnesium bromide in tetrahydrofuran (1M, 560 mL). The flask was set up with a $N_2$ blanket and magnetic stirring. The flask was seated in ice-salt-water bath (−5 to −8° C.). 1,2-Dimethylamino ethyl ether (106 mL) in tetrahydrofuran (100 mL) was dropped to the flask through an addition funnel over 10 minutes. The mixture was stirred for 1 hour. 4-Bromobenzoyl chloride in tetrahydrofuran (122 g in 100 mL) suspension was dropped into the flask using an addition funnel over 20 minutes. The cooling bath was removed 1 hour after the addition. The mixture was stirred at room temperature for 20 hours. The solution was poured into brine (1 L). Conc. hydrochloric acid (250 mL) was added to the mixture slowly. The top layer was separated and filtered through magnesium sulfate. The solution was concentrated to initially yield an orange-red oily residue (182 g) that became a yellow waxy product. The residue was dried under high vacuum and used as is in next step.

Step 2

The product from Step 1 (182 gram) was dissolved in toluene (1 L) in a 2 L single-neck RB flask with $N_2$ blanket and overhead stirring. Dimethyl succinate (72 mL) was added to the same flask. Potassium t-butoxide (68 gram) was added to the mixture in portions over 20 minutes. The reaction mixture stirred at room temperature for 20 hours. After 3 hours the dark slurry was poured into cold water (400 mL). The bottom water layer was separated and acidified by conc. HCl (200 mL). The slurry was extracted with ethyl acetate twice with (500 mL and 300 mL). The top solution was dried over sodium sulfate and concentrated. The residue was dried under high vacuum (170 g) and used as is in next step.

Step 3

The product from Step 2 (170 grams) and trace amount of 4-dimethylaminopyridine (0.2 gram) were dissolved in acetic anhydride (250 mL) in 1 L single-neck RB flask equipped with a water condenser and magnetic stirring under $N_2$ blanket. The reaction mixture was heated to 120° C. for 3 hours. The mixture was then condensed down to less volume under reduced pressure. The recovered oily residue was dissolved in methanol. Solid product crystallized out and was recovered by filtration yielding (80 grams). NMR analysis showed the product to have a structure consistent with methyl 4-acetoxy-1-(4-bromophenyl)-7-methoxy-2-naphthoate.

Step 4

To a 1 L single-neck flask was added the product of Step 3 (63 g), phenylboronic acid (21 g), potassium carbonate (100 g), toluene (240 mL), ethanol (120 mL) and water (120 mL). The mixture was bubbled with $N_2$ for 15 minutes. Tetrakis(triphenylphosphine)palladium(0) (1.5 g) was added to the mixture. The reaction mixture was heated to reflux for 4.5 hours. The mixture was cooled to room temperature and poured into water (500 mL). The resulting mixture was acidified with concentrated hydrochloric acid (12N, 200 mL). The top organic layer was recovered, filtered through magnesium sulfate and then concentrated. Solid product was obtained from the solution. The mother liquor was filtered through a short silica gel plug. Solid product was obtained from the major fraction. The combined product (64 g) was dried in vacuum oven.

Step 5

To a 3 L one-neck RB flask was added dry solid lanthanum (III) chloride (130 g), lithium chloride (37 g), the product from Step 4 (60 g) and anhydrous THF (1.5 L). The white slurry was stirred at room temperature for 20 hours. The flask was cooled in a dry ice/acetone bath. N-Propylmagnesium chloride in tetrahydrofuran solution (2M, 425 mL) was dropped to the mix slowly. The cooling bath was removed upon completing the addition. The reaction mixture was stirred for 3 hours. The mixture was poured into 30% aqueous hydrochloric acid (500 mL) and ice. The recovered top layer was filtered over magnesium sulfate and then concentrated. The resulting oily product (74 g) was used as is in the next step.

Step 6

The product from Step 5 was dissolved in xylene (400 mL) in a 2 L single-neck flask equipped with Dean-Stark trap and water condenser. Bismuth trifluoromethanesulfonate (1.6 g) was added to the flask. The reaction mixture was heated to reflux for 4 hours. The resulting mixture was cooled to room temperature and filtered through a silica gel plug. The major fraction was collected and condensed to less volume. Solid product (65 g) was recrystallized out from t-butyl methyl ether/hexane solution to yield an off-white solid, 9-phenyl-2-methoxy-7,7-dipropyl-7H-benzo[c]fluoren-5-ol.

Step 7

In a flask placed under a nitrogen atmosphere, the product of Step 6 (4.95 g) and dichloromethane (250 mL) were combined and stirred. To this mixture was added trifluoroacetic acid (0.48 g) and the mixture was heated to reflux. To this mixture was added 1,1-bis-[4-((ditetrahydro-2H-pyran-2-yl)oxy)phenyl]-2-propyn-1-ol (5.95 g) over a 15 minute period. After stirring at reflux temperature for 2 hours, additional trifluoroacetic acid (7 drops) was added, and then additional 1,1-bis-[4-((ditetrahydro-2H-pyran-2-yl)oxy)phenyl]-2-propyn-1-ol (2.5 g) was added over a 10 minute period. The mixture was stirred at reflux temperature for an additional 4 hours. Methanol (50 mL) and p-toluenesulfonic acid (0.2 g) were then added. The mixture was stirred at room temperature for 16 hours. The reaction mixture was then washed with a saturated aqueous solution of sodium bicarbonate (2×300 mL). The recovered organic layer was dried over sodium sulfate and concentrated on a rotary evaporator to give 7.1 g of a purplish solid. The material was purified by column chromatography, and the pure fractions were combined and concentrated by rotary evaporation to give 5.2 g of a purplish oily solid. The solid was crystallized from a mixture of diethyl ether and ethyl acetate, and then collected by vacuum filtration to obtain 4.3 g of an off-white solid. NMR spectroscopy confirmed the structure of the product to be consistent with 3,3-bis-(4-hydroxyphenyl)-7-methoxy-1'-phenyl-13,13-dipropyl-3H,13H-indeno[2',3':3,4]naphtho[1,2-b]pyran as shown in the following graphic formula:

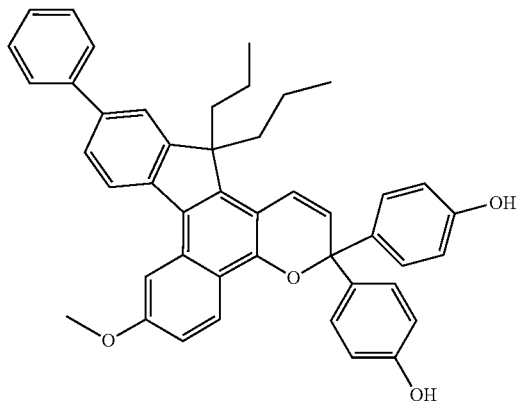 [SMILES: CCCC1(CCC)c2cc(-c3ccccc3)ccc2-c2c1c1c(c3ccc(OC)cc23)OC(c2ccc(O)cc2)(c2ccc(O)cc2)C=C1]

Example 11

Step 1

Two grams of the product of Example 9, (3,3-dimethoxyphenyl-7-methoxy-11-phenyl-13-carbomethoxy-13-methyl-3H,13H-indeno[2',3':3,4]naphtho[1,2-b]pyran) was added to a reaction flask containing 50 mL of anhydrous diethyl ether. Small portions of lithium aluminum hydride (0.4 g) were added to the stirred mixture until all of the red-orange color disappeared. The reaction mixture was stirred an additional ten minutes, quenched with a small amount of ethanol, and poured into 150 mL of 5 weight percent aqueous hydrochloric acid. The organic layer was separated, recovered, washed with water, filtered, and the solvent was removed on a rotary evaporator yielding 1.7 g of product. An NMR spectrum showed that the structure was consistent with 3,3-bis-(4-methoxyphenyl)-7-methoxy-1'-phenyl-13-hydroxymethyl-13-methyl-3H,13H-indeno[2',3':3,4]naphtho[1,2-b]pyran as shown in the following graphic formula:

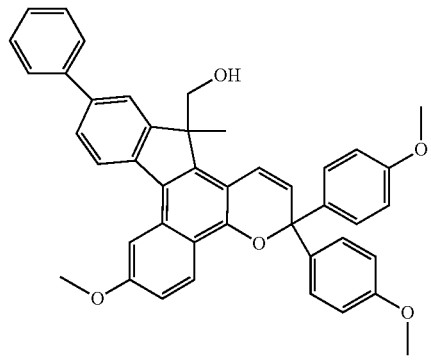 [SMILES: COc1ccc(C2(c3ccc(OC)cc3)C=Cc3c4c(c5cc(OC)ccc5c3O2)-c2ccc(-c3ccccc3)cc2C4(C)CO)cc1]

Example 12

Step 1

The product of Step 3 of Example 5 (9-bromo-7,7-dimethyl-7H-benzo[c]fluoren-5-ol (7.7 g)) and phenyl boronic acid (3.5 g) were added to a solution of dimethoxyethane (100 mL) and water (50 mL) in a 250 mL round bottom three-necked flask, followed by addition of $Na_2CO_3$ (5.1 g). The resulting solution was bubbled with nitrogen for 10 minutes and then the catalyst, tetrakis(triphenylphosphine)palladium (0.8 g), was added to the reaction mixture. The resulting reaction mixture was heated to reflux temperatures under a nitrogen atmosphere. The reaction was monitored by thin layer chromatography (TLC) analysis and by the end of the reaction; it was cooled to room temperature and quenched by adding water (30 mL). The pH of reaction mixture was adjusted to 5-6 by adding hydrochloric acid (37%, 9.5 g) slowly. The product was extracted with ethyl acetate (2×50 mL). The organic layers were recovered, combined, dried over anhydrous sodium sulfate, and concentrated by rotary evaporation to yield the product (11 g). The product was slurried over mixtures of hexanes and ethyl acetate (50 mL, hexanes/ethyl acetate, v/v, 9/1). The product was filtered off and washed with mixtures of hexanes and ethyl acetate (hexanes/ethyl acetate, v/v, 9/1) three times (3×20 mL) to provide yellowish solid containing 7,7-dimethyl-9-phenyl-7H-benzo[c]fluoren-5-ol (8 g).

Step 2

The product of Step 1, (1.3 g), was dissolved in dichloromethane (70 mL) in a 250 mL three-necked flask, followed by addition of p-Toluenesulfonic acid (0.2 g). Then, 1-phenyl-1-(4-(piperidin-1-yl)phenyl)prop-2-yn-1-ol (1.2 g), prepared as described in U.S. Pat. No. 7,556,751, which disclosure is incorporated herein by reference, was added to the reaction mixture. The reaction was stirred at room temperature. Two hours later, trifluoroacetic acid (1 mL) was added to the reaction mixture. More, 1-phenyl-1-(4-(piperidin-1-yl)phenyl)prop-2-yn-1-ol (0.4 g), was added to the reaction mixture. The reaction was completed in another two hours. Saturated aqueous $NaHCO_3$ (20 mL) was added to the reaction mixture. It was stirred for 30 minutes. The product was extracted with dichloromethane (2×30 mL). The recovered organic layers were combined, dried over anhydrous $MgSO_4$, and concentrated under vacuum to provide the product (2.0 g). This material was purified by column chromatography (silica gel, 70% hexanes and 30% ethyl acetate as the eluant).

The fractions containing product were combined, rotovaped, and dried under vacuum to provide a solid. The solid was then slurried over acetone (10 mL). The product was filtered off and washed with acetone (2×10 mL) to give product (0.2 g). An NMR spectrum showed that the structure was consistent with 3-(4-piperidylphenyl)-3-phenyl-1'-phenyl-13,13-dimethyl-3H,13H-indeno[2',3':3,4]naphtho[1,2-b]pyran as shown in the following graphic formula:

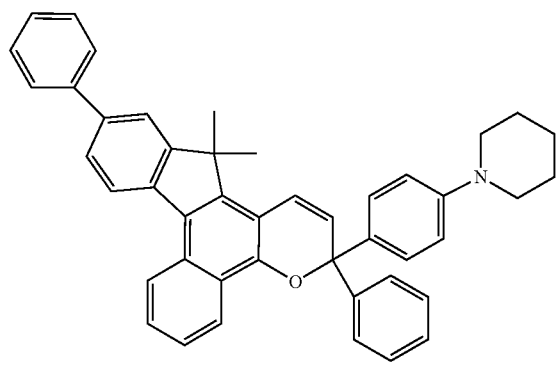 [SMILES: CC1(C)c2cc(-c3ccccc3)ccc2-c2c1c1c(c3ccccc23)OC(c2ccccc2)(c2ccc(N3CCCCC3)cc2)C=C1]

Example 13

Step 1

The product of Step 3 of Example 5, (9-bromo-2-methoxy-7,7-dimethyl-7H-benzo[c]fluoren-5-ol (6 g)) and 2-methoxyphenyl boronic acid (2.8 g) were added to a solution of dimethoxyethane (40 mL) and water (20 mL) in a 250 mL round bottom 3-necked flask, followed by addition of $Na_2CO_3$ (3.5 g). The resulting solution was bubbled with nitrogen for 10 minutes and then the Palladium catalyst, $Pd[PPh_3]_4$, 0.5 g, was added to the reaction mixture. Then the reaction mixture heat to reflux temperatures under a nitrogen atmosphere. The reaction was monitored by TLC analysis. By the end of reaction, the reaction was cooled to room temperature and quenched by adding water (30 mL). The pH of reaction mixture was adjusted to 5-6 by adding hydrochloric acid (37%, 7.5 g) slowly. The product was extracted with ethyl acetate (2×50 mL). The organic layers were combined, dried over anhydrous sodium sulfate, and concentrated by rotary evaporation to yield the product, 2-methoxy-9-(2-methoxyphenyl)-7,7-dimethyl-7H-benzo[c]fluoren-5-ol (5.7 g) which was used for next reaction as is.

Step 2

The product of Step 1, (3.0 grams), was dissolved in chloroform (30 mL) in a 100 mL 3-necked flask. Pyridinium p-toluenesulfonate (0.6 g) was added to the mixture. Then, 1-(4-butoxyphenyl)-1-(4-morpholinophenyl)-2-propyn-1-ol, 2.9 g was added to the reaction mixture. The reaction was stirred at room temperature for four hours. Saturated aqueous $NaHCO_3$ (15 mL) was added to the reaction mixture. It was stirred for 30 minutes. The product was extracted with dichloromethane (2×30 mL). The organic layers were combined, dried over anhydrous $MgSO_4$, and concentrated under vacuum to provide the product (5.4 g). This material was purified by column chromatography (silica gel, 70% hexanes and 30% ethyl acetate as the eluant). The fractions containing product were combined, rotovaped, and dried under vacuum to provide product 1.7 g. An NMR spectrum showed that the structure was consistent with 3-(4-butoxyphenyl)-3-(4-morpholinoyphenyl)-7-methoxy-1'-(2-methoxyphenyl)-13,13-dimethyl-3H,13H-indeno[2',3':3,4]naphtho[1,2-b]pyran as shown in the following graphic formula:

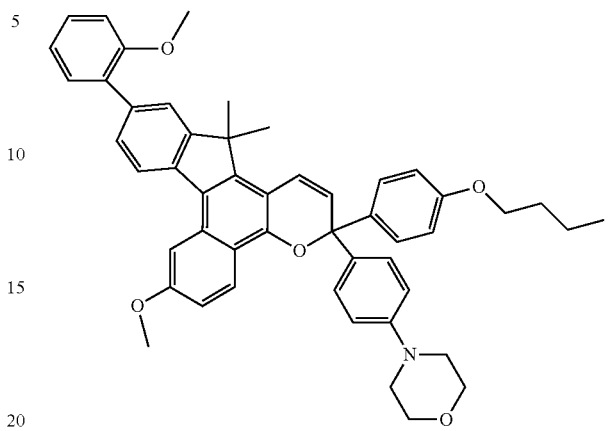

Example 14

Step 1

4,4'-Dihydroxy benzophenone (150 g) was added to dimethylformamide (DMF) (1000 mL) in a 3 L three-necked reactor equipped with condenser, followed by addition of potassium carbonate (435 g). The reaction mixture was heated to 100° C. Iodobutane (451 g) was added to the mixture over 40 minutes. After the addition was done, the reaction mixtures were heated at 100° C. for four hours. The reaction was then cooled to room temperature and quenched by pouring the mixtures to water (500 mL). The product was extracted with ethyl acetate twice (2×400 mL). The combined organic layers were washed with water three times (3×300 mL). The organic layer was dried over anhydrous $MgSO_4$, and concentrated under vacuum to provide product (234 grams) containing dibutoxybenzophenone which was used for next step without further purification.

Step 2

The product of Step 1 (130 g) was dissolved in DMF (400 mL) in a 2 L three-necked flask. The reaction mixture was saturated with acetylene gas for 15 minutes. Then sodium acetylide (192 g, 18 wt. % slurry in xylene: light mineral oil, 95% purity) was added to the reaction mixture over 40 minutes while the reaction was maintained at 10-15° C. After the addition was over, the reaction mixture was warmed to room temperature. After one hour, the reaction was quenched by pouring to aqueous saturated $NH_4Cl$ (300 mL). Ethyl acetate (400 mL) was added. The organic layer was separated, washed with water three times (3×200 mL), dried over anhydrous $MgSO_4$, and concentrated under vacuum to provide product 130 g with some mineral oil present. The product was passed thru a plug column (Silica gel) to provide product containing bis-1,1'-(4-butoxyphenyl)-2-propyn-1-ol (120 g).

Step 3

2-Methoxy-7,7-dimethyl-9-phenyl-7H-benzo[c]fluoren-5-ol (26 grams), prepared according to Steps 1 to 7 of Example 2, was dissolved in chloroform (100 mL) in a 250 mL three-necked flask. Pyridinium p-toluenesulfonate (1.8 g) was added to the mixture. The product of Step 2, (27 g), was added to the reaction mixture. The reaction mixture was heated to reflux for one hour. The resulting mixture was cooled to room temperature and quenched by adding saturated aqueous $NaHCO_3$ (30 mL) and stirred for 30 minutes.

The product was extracted with dichloromethane (2×50 mL). The organic layers were recovered, combined, dried over anhydrous MgSO₄, and concentrated under vacuum to provide the product (50 g). This material was purified using CombiFlash® Rf from Teledyne ISCO (80% hexanes and 20% ethyl acetate as the eluant). The pure fractions were combined, rotovaped, and dried under vacuum to provide a solid. The solid was then slurried in a mixture of hexanes/ethyl acetate (100 mL, 3/1, v/v). The product was filtered off and washed with a mixture of hexanes/ethyl acetate twice (2×30 mL, 3/1, v/v) to give product (30 g). An NMR spectrum showed that the structure was consistent with 3,3-bis-(4-butoxyphenyl)-7-methoxy-1'-phenyl-13,13-dimethyl-3H,13H-indeno[2',3':3,4]naphtho[1,2-b]pyran as shown in the following graphic formula:

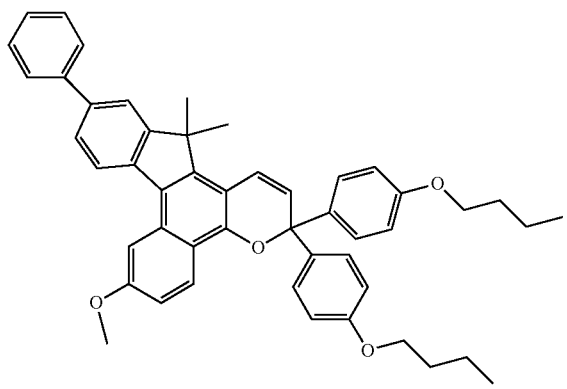 [SMILES: CCCCOc1ccc(C2(c3ccc(OCCCC)cc3)C=Cc3c4c(c5cc(OC)ccc5c3O2)-c2ccc(-c3ccccc3)cc2C4(C)C)cc1]

Example 15

Step 1

The product of Step 3 of Example 5,9-bromo-7,7-dimethyl-7H-benzo[c]fluoren-5-ol (6 g) and 4-tert-butylphenyl boronic acid (3.7 g) were added to a solution of dimethoxyethane (60 mL) and water (30 mL) in a 250 mL round bottom three-necked flask, followed by addition of Na₂CO₃ (4 g). The resulting solution was bubbled with nitrogen for 10 minutes and tetrakis(triphenylphosphine)palladium (0.2 g), was added to the reaction mixture. The resulting reaction mixture was heated to reflux under a nitrogen atmosphere. The reaction was monitored by TLC analysis. By the end of reaction, the reaction was cooled to room temperature and quenched by adding water (30 mL). The pH of reaction mixture was adjusted to 5-6 by adding hydrochloric acid (37%, 7.7 g) slowly. The product was extracted with ethyl acetate (2×50 mL). The organic layers were combined, dried over anhydrous magnesium sulfate, and concentrated by rotary evaporation to yield the product (10 g). The product was purified using CombiFlash® Rf from Teledyne ISCO (80% hexanes and 20% ethyl acetate as the eluant). The fractions containing product were combined, rotovaped, and dried under vacuum to provide a solid containing 9-(4-(tert-butyl)phenyl)-7,7-dimethyl-7H-benzo[c]fluoren-5-ol (4 g).

Step 2

The product of Step 1, (1.6 g), was dissolved in dichloroethane (20 mL) in a 100 mL three-necked flask equipped with a condenser. Pyridinium p-toluenesulfonate (0.4 g) and trimethyl orthoformate (1.7 g) were added to the mixture. 1-(4-Morpholinophenyl)-1-phenylprop-2-yn-1-ol (1.5 g), which was heated to reflux for three hours and cooled to room temperature. The reaction was quenched by adding saturated aqueous NaHCO₃ (20 mL) and was stirred for 30 minutes. The product was extracted with dichloromethane (2×20 mL). The organic layers were recovered, combined, dried over anhydrous MgSO₄, and concentrated under vacuum to provide the product (4 g). This material was purified using CombiFlash® Rf from Teledyne ISCO (70% hexanes and 30% ethyl acetate as the eluant). The fractions containing product were combined, rotovaped, and dried under vacuum to provide a solid. The solid was then slurried over methanol. The product was filtered off and washed with methanol twice (2×10 mL) to give a solid product (2.3 g). An NMR spectrum showed that the structure was consistent with 3-(4-morpholinophenyl)-3-phenyl-1'-(4-t-butylphenyl)-13,13-dimethyl-3H,13H-indeno[2',3':3,4]naphtho[1,2-b]pyran as shown in the following graphic formula:

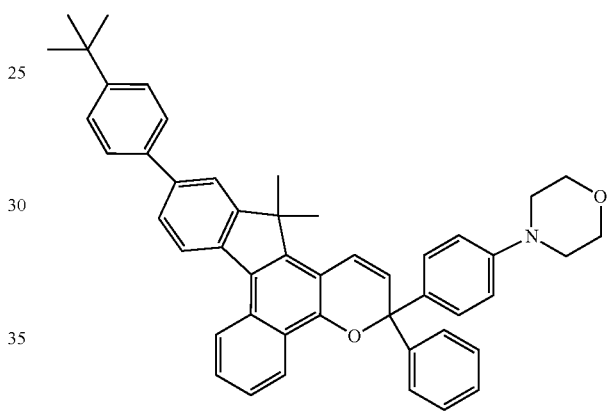

Example 16

Step 1

A 200 mL flask was loaded with the product of Step 2 of Example 21, (9-bromo-7,7-dimethyl-7H-benzo[c]fluoren-5-yl acetate (4.0 g)), 2,4-difluorophenylboronic acid (2.0 g), potassium carbonate (1.4 g), palladium acetate (0.07 g), triphenylphosphine (0.25 g), 1,2-dimethoxyethane (40 mL), and water (20 mL). Nitrogen was bubbled through the reaction mixture for 10 minutes. The solution was stirred at 80° C. overnight and cooled to room temperature and the aqueous phase was separated. The recovered organic phase was diluted with dichloromethane and washed twice with brine before drying over Na₂SO₄ and evaporating the solvent. The resulting residue was chromatographed on a short silica gel column, eluting with 30% ethylacetate (EtOAc) in hexanes to provide 3.7 g of product. This solid was used as is for the next step.

Step 2

The product of Step 1 (1.6 g), 1-(4-butoxyphenyl)-1-(4-fluorophenyl)prop-2-yn-1-ol (1.6 g) and dichloroethane (20 mL) were combined in a 50 mL reaction flask. To this mixture, pyridine p-toluenesulfonate (PPTS) was added (0.05 g). The reaction mixture was stirred at room temperature overnight. The solvent was removed before purifying the residue by column chromatography on silica gel. Product containing fractions were combined and the product was recrystallized from dichloromethane/ethanol mixture to afford 1.3 g. NMR analysis showed the product to have a structure consistent with 3-(4-butoxyphenyl)-3-(4-fluorophenyl)-11-(2,4-difluorophenyl)-13,13-dimethyl-3H,13H-indeno[2',3':3,4]naphtho[1,2-b]pyran as shown in the following graphic formula:

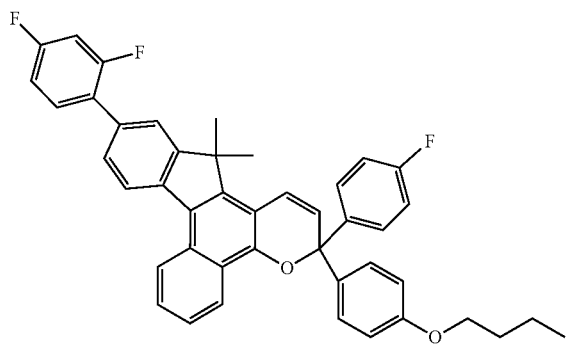 [SMILES: CCCCOc1ccc(C2(c3ccc(F)cc3)C=Cc3c4c(c5ccccc5c3O2)-c2ccc(-c3ccc(F)cc3F)cc2C4(C)C)cc1]

Example 17

Step 1

A 100 mL flask was loaded with the product of Step 2 of Example 21, (9-bromo-7,7-dimethyl-7H-benzo[c]fluoren-5-yl acetate (1.1 g)), 2-(9,9-bis-(2-ethylhexyl)-9H-fluoren-2-yl)-4,4,5,5-tetramethyl-1,3,2-dioxaborolane (1.5 g), potassium carbonate (1.0 g), tris(dibenzylideneacetone)dipalladium (0.1 g), tri(o-tolyl)phosphine (0.1 g), 1,2-dimethoxyethane (40 mL), and water (20 mL). Nitrogen was bubbled through the reaction mixture for 10 minutes. The solution was stirred at 85° C. overnight and cooled to room temperature and the aqueous phase separated. The recovered organic phase was diluted with dichloromethane and washed twice with brine before drying over $Na_2SO_4$ and evaporating the solvent. The resulting residue was chromatographed on a short silica gel column, eluting with 20% ethylacetate (EtOAc) in hexanes to provide 1.5 g of product as red oil. This material was used as is for the next reaction.

Step 2

The product of Step 1 (0.9 g), 1-(4-butoxyphenyl)-1-(4-fluorophenyl)prop-2-yn-1-ol (0.9 g) and dichloroethane (20 mL) were combined in a 50 mL reaction flask. To this mixture, PPTS was added (0.05 g). The reaction mixture was stirred at room temperature overnight. The solvent was removed before purifying the residue by column chromatography on silica gel. Product containing fractions were combined and the product was recrystallized from dichloromethane/ethanol mixture to provide 0.9 g of product. NMR analysis showed the product to have a structure consistent with 3-(4-butoxyphenyl)-3-(4-fluorophenyl)-11-(9,9-bis-(2-ethylhexyl)-9H-fluoren-2-yl)-13,13-dimethyl-3H,13H-indeno[2',3':3,4]naphtho[1,2-b]pyran as shown in the following graphic formula:

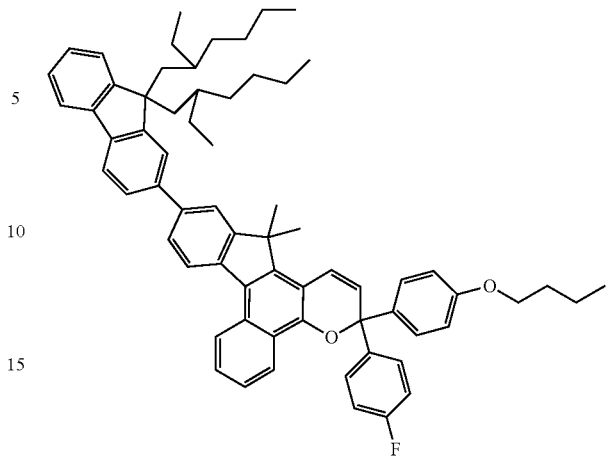

Example 18

Step 1

Into a dry 500 mL flask was added 140 mL of methyl magnesium chloride and a solution of methyl 4-acetoxy-1-(4-bromophenyl)-7-methoxy-2-naphthoate (16.0 g) in THF (250 mL). The resulting mixture was stirred at room temperature for 1 hour. The reaction was quenched with water, the pH adjusted to 3 with HCl, and extracted with EtOAc. The resulting organic phase was collected, washed with brine, dried over $Mg_2SO_4$ and the solvent evaporated. The compound was used as is for the next step.

Step 2

The product from Step 1 (16.0 g) was dissolved in 150 ml of xylenes. Bismuth(III) trifluoromethanesulfonate (1.0 g) and butylated hydroxytoluene (BHT) (0.03 g) were added and the system was heated to reflux for one hour. The mixture was concentrated in xylenes and washed with water/DCM. The residue was filtered through a silica plug using 10-30% ethyl acetate/hexanes as eluent and the resulting material was used as is for the next step.

Step 3

The product of Step 2,9-bromo-2-methoxy-7,7-dimethyl-7H-benzo[c]fluoren-5-ol (5.0 g) was placed in a 200 mL flask with 4,4,5,5-tetramethyl-1,3,2-dioxaborolane (4.2 g), potassium acetate (4.0 g) and a palladium catalyst, Pd(dppf)Cl₂, (0.75 g) in dry triethylamine (80 mL). The solution was purged with nitrogen for 10 min and then stirred at 80° C. overnight. The solvent was removed and the residue was extracted with ethyl acetate and water. The organic phase was dried with sodium sulfate and subject to column chromatography using 30-35% ethyl acetate/hexanes as eluent to provide 5.1 grams of product. Proton Nuclear Magnetic Resonance (NMR) analysis showed the product to have a structure consistent with 2-methoxy-7,7-dimethyl-9-(4,4,5,5-tetramethyl-1,3,2-dioxaborolan-2-yl)-7H-benzo[c]fluoren-5-ol.

Step 4

A 100 mL flask was loaded with the product of Step 3 (1.1 g), 5-bromopyrimidine (0.5 g), potassium carbonate (1.5 g), palladium acetate (0.05 g), triphenylphosphine (0.1 g), 1,2-dimethoxyethane (25 mL), and water (10 mL). Nitrogen was bubbled through the reaction mixture for 10 minutes. The solution was stirred at 80° C. overnight, cooled to room temperature and the aqueous phase separated. The recovered organic phase was diluted with dichloromethane and washed twice with brine before drying over $Na_2SO_4$ and evaporating the solvent. The resulting residue was chromatographed on a short silica gel column, eluting with 50-70% EtOAc in hexanes to provide 0.5 g of product as yellow solid. This material was used as is for the next reaction.

Step 5

The product of Step 4 (0.5 g), 1-(4-butoxyphenyl)-1-(4-methoxyphenyl)-2-propyn-1-ol (0.9 g) and chloroform (15 mL) were combined in a 50 mL reaction flask. To this mixture, PPTS was added (0.05 g). The reaction mixture was stirred at room temperature overnight. The solvent was removed before purifying the residue by column chromatography on silica gel. Product containing fractions were combined and the product was recrystallized from dichloromethane/ethanol mixture to provide 0.4 g. NMR analysis showed the product to have a structure consistent with 3-(4-butoxyphenyl)-3-(4-methoxyphenyl)-7-methoxy-11-(5-pyrimidinyl)-13,13-dimethyl-3H,13H-indeno[2',3':3,4]naphtho[1,2-b]pyran as shown in the following graphic formula:

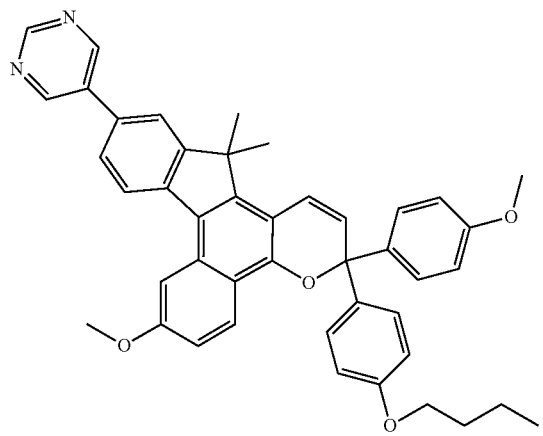 [SMILES: CCCCOc1ccc(C2(c3ccc(OC)cc3)C=Cc3c4c(c5cc(OC)ccc5c3O2)-c2ccc(-c3cncnc3)cc2C4(C)C)cc1]

Example 19

Step 1

A 200 mL flask was loaded with the product of Step 3 of Example 18, (2-methoxy-7,7-dimethyl-9-(4,4,5,5-tetramethyl-1,3,2-dioxaborolan-2-yl)-7H-benzo[c]fluoren-5-ol (1.0 g)), 2-bromo-9,9-bis-(2-ethylhexyl)-9H-fluorene (1.2 g), potassium carbonate (0.5 g), palladium acetate (0.05 g), triphenylphosphine (0.1 g), 1,2-dimethoxyethane (50 mL), and water (25 mL). Nitrogen was bubbled through the reaction mixture for 10 minutes. The solution was stirred at 80° C. overnight. After completion, the reaction was cooled to room temperature and the aqueous phase separated. The recovered organic phase was diluted with dichloromethane and washed twice with brine before drying over Na$_2$SO$_4$ and evaporating the solvent. The resulting residue was chromatographed on a short silica gel column, eluting with 20-30% EtOAc in hexanes to provide 1.5 g of product containing 9-(9,9-bis(2-ethylhexyl)-9H-fluoren-2-yl)-2-methoxy-7,7-dimethyl-7H-benzo[c]fluoren-5-ol as oil. This material was used as is for the next reaction.

Step 2

The product of Step 1 (1.5 g), 1-(4-butoxyphenyl)-1-(4-methoxyphenyl)-2-propyn-1-ol (0.65 g) and dichloroethane (40 mL) were combined in a 100 mL reaction flask. To this mixture, PPTS was added (0.05 g). The reaction mixture was stirred at 55° C. for three hours. The solvent was removed before purifying the residue by column chromatography on silica gel using 10% EtOAc in hexanes as eluent. Product containing fractions were combined and the product was recrystallized from dichloromethane/ethanol mixture to provide 1.1 g. NMR analysis showed the product to have a structure consistent with 3-(4-butoxyphenyl)-3-(4-methoxyphenyl)-7-methoxy-11-(9,9-bis-(2-ethylhexyl)-9H-fluoren-2-yl)-13,13-dimethyl-3H,13H-indeno[2',3':3,4]naphtho[1,2-b]pyran as shown in the following graphic formula:

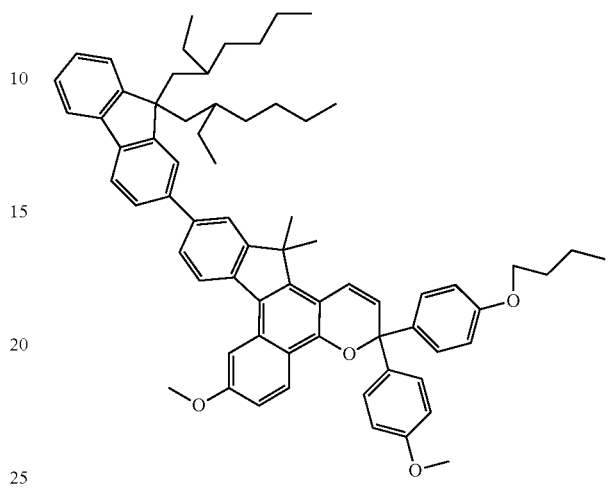

Example 20

Step 1

The product of Step 1 of Example 19, 9-(9,9-bis(2-ethylhexyl)-9H-fluoren-2-yl)-2-methoxy-7,7-dimethyl-7H-benzo[c]fluoren-5-ol (0.6 g)) was mixed with 1-(4-methoxyphenyl)-1-(4-morpholinophenyl)-2-propyn-1-ol (0.45 g) and dichloroethane (40 mL) in a 100 mL reaction flask. To this mixture, PPTS was added (0.05 g). The reaction mixture was stirred at 55° C. for three hours. The solvent was removed before purifying the residue by column chromatography on silica gel using 10-30% EtOAc in hexanes as eluent. Product containing fractions were combined and the product was recrystallized from dichloromethane/ethanol mixture to provide 0.7 g. NMR analysis showed the product to have a structure consistent with 3-(4-morpholinophenyl)-3-(4-methoxyphenyl)-7-methoxy-1'-(9,9-bis-(2-ethylhexyl)-9H-fluoren-2-yl)-13,13-dimethyl-3H,13H-indeno[2',3':3,4]naphtho[1,2-b]pyran as shown in the following graphic formula:

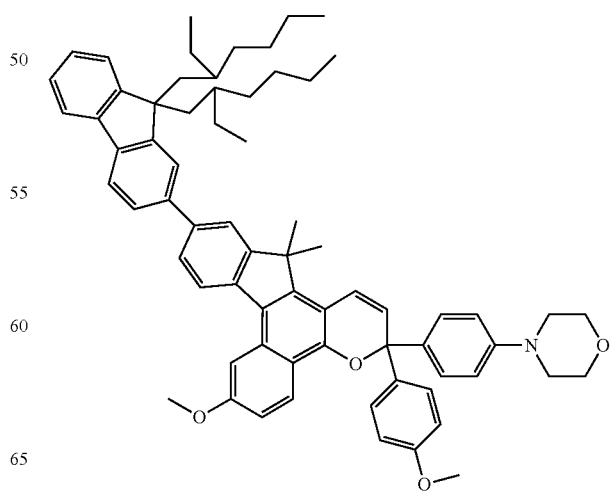

Example 21

Step 1

Into a 1 L reaction flask containing acetic anhydride (600 mL) was added 7,7-dimethyl-7H-benzo[c]fluoren-5-ol (150 g) followed by the addition of, 4-dimethylaminopyridine (DMAP) (0.2 g). The reaction mixture was heated to 130° C. and maintained at this temperature for 2 to 3 hours. The resulting reaction mixture was cooled to 120° C. and maintained at this temperature overnight and cooled to room temperature prior to being poured into ice water and stirred for 2 hours. An off-white solid formed and was collected by filtration. The recovered solid was washed with water, and then with MeOH/water (v/v, 50/50). The product 7,7-dimethyl-7H-benzo[c]fluoren-5-yl acetate was air-dried to yield 175 g solid and was used in the next step without further purification.

Step 2

Into a 1 L reaction flask containing 400 mL of DMF was added the product of Step 1 (120 g) followed by the addition of N-bromosuccinimide (NBS, 82 g). The reaction mixture was heated to 90° C., spiked to 120° C. briefly and returned to about 95° C. and was heated at this temperature for 4 hours. Additional NBS was added (8 g) and the reaction mixture was heated for 2 more hours. The resulting reaction mixture was poured into water and was extracted with EtOAc. The recovered organic layer was washed with water (3×200 mL), dried over $MgSO_4$ and concentrated under vacuum to provide product. The product was slurried in MeOH and the solid was recovered by filtration, washed with methanol (MeOH) (3×200 mL) and dried to provide a light yellowish solid (107 g) containing 9-bromo-7,7-dimethyl-7H-benzo[c]fluoren-5-yl acetate which was used in the next step without purification.

Step 3

Into a 1 L reaction flask containing MeOH (500 mL) was added the product of Step 2 (107 g) followed by the addition of conc. HCl, 37% (3 g). The reaction mixture was heated to reflux for 2 hours. The solvents were removed from the resulting reaction mixture to yield about 100 g solid. The recovered solid was slurried in about 250 mL of dichloromethane DCM/Hexanes (v/v, 50/50) for 10 minutes at room temperature. The slurry was filtered and the recovered solid was washed with DCM/Hexanes (v/v, 5/5) to provide about 47 g of product. NMR analysis showed the product to have a structure consistent with 7,7-dimethyl-9-bromo-7H-benzo[c]fluoren-5-ol.

Step 4

The product of Step 3 (3 g) and 4-(N,N-dimethylamino) phenyl boronic acid (2 g) were added to a 0.5 L reaction flask containing a solution of dimethoxyethane (150 mL) and water (50 mL) followed by the addition of $K_2CO_3$ (3.7 g) and triphenylphosphine (1.15 g). The resulting solution was bubbled with nitrogen for 10 minutes and then palladium acetate (0.2 g) was added to the reaction mixture. The reaction mixture was heated to reflux under a nitrogen atmosphere. After 4 h, the reaction mixture was cooled to room temperature and poured into 400 mL of water followed by extraction with EtOAc (2×150 mL). The recovered organic layers were combined and washed with brine (200 mL). This organic layer was dried over $Mg_2SO_4$ and, after filtration and evaporation of the solvents yielded the product (3.5 g) which was used in the next step without purification. MS analysis supported the molecular weight of the product 9-(4-(dimethylamino)phenyl)-7,7-dimethyl-7H-benzo[c]fluoren-5-ol.

Step 5

The procedure of Step 1 of Example 7 of U.S. Pat. No. 7,465,415B2 was followed except that (4-hydroxyphenyl)(4-methoxyphenyl)methanone was used instead of (4-fluorophenyl)(4-hydroxyphenyl)methanone to produce (4-(2-hydroxyethoxy)phenyl)(4-methoxyphenyl)methanone. MS analysis supported the molecular weight of the product.

Step 6

The procedure of Step 1 of Example 5 of U.S. Pat. No. 7,465,415B2 was followed except that the product of Step 5 above was used in place of (4-fluorophenyl)(4-(2-hydroxyethoxy)phenyl)methanone to produce 1-(4-(2-hydroxyethoxy)phenyl)-1-(4-methoxyphenyl)prop-2-yn-1-ol. The product was used without further purification.

Step 7

Into a 0.5 L reaction flask the product Step 4 (4.0 g) and the product Step 6 (6.0 g) were dissolved in DCM (300 mL). p-Toluene sulfonic acid (PTSA) (0.13 g) was added and the mixture was stirred at room temperature for 4 hrs. The reaction mixture was washed with water (200 mL) and then the solvent was evaporated. The resulting residue was purified by column chromatography eluting with DCM/EtOAc (4/1, V/V) to provide the product (7.0 g). NMR analysis showed the product to have a structure consistent with 3-(4-(2-hydroxyethoxy)phenyl)-3-(4-methoxyphenyl)-11-(4-(N,N-dimethylamino)phenyl)-13,13-dimethyl-3H,13H-indeno[2',3':3,4]naphtho[1,2-b]pyran as shown in the following graphic formula:

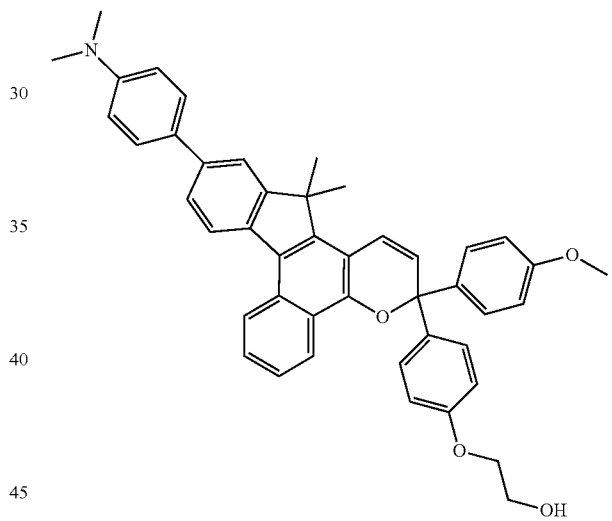

Example 22

Step 1

Bromo(3-methoxyphenyl)magnesium (1M in THF, 98 mL) was poured into a dry 1 L flask and the mix cooled in an ice bath. Bis-[2-(N,N-dimethylamino)-ethyl]ether (18.6 mL) was added in one portion while stirring. After 25 min the solution was slowly added to a chilled solution of 4-biphenyl carbonyl chloride (21 g) in dTHF (40 mL). After 10 min the ice bath was removed and the reaction was mixed at room temperature for 12 hrs. Water (150 mL) was added to the reaction mixture, and the pH adjusted to 5 with HCl conc. (10 mL). The mixture was extracted using EtOAc (2 times with 300 mL each time). The recovered organic fraction was then washed with water (200 mL), brine (200 mL) and dried over $Mg_2SO_4$. After filtration and evaporation of the solvent the product (28 g) was collected. MS analysis supported the molecular weight of [1,1'-biphenyl]-4-yl(3-methoxyphenyl)methanone.

Step 2

Steps 1 to 5 of Example 1 in US2006/0228557A1 were followed except that the product of Step 1 above was used in place of 3,4-dimethoxy-4'-bromobenzophenone to produce 2-methoxy-7,7-dimethyl-9-phenyl-7H-benzo[c]fluoren-5-ol. MS analysis supported the molecular weight of the product.

Step 3

Into a 0.5 L reaction flask was added DMF (200 mL), (4-fluorophenyl)(4-hydroxyphenyl)methanone (15 g) and $K_2CO_3$ (29 g). The resulting mixture was stirred under nitrogen atmosphere and allylbromide (48 mL) was added. The reaction was stirred for 12 hrs at 75° C. The mixture was filtered through filter paper and the filtrate collected. DCM (250 mL) was added, and the mixture was washed with water (5 times with 400 mL each time). The resulting organic layer was collected and the solvents evaporated to produce 19 g of product. MS analysis supported the molecular weight of 4-(allyloxy)phenyl)(4-fluorophenyl)methanone.

Step 4

Steps 2 to 3 of Example 7 of U.S. Pat. No. 7,465,415B2 were followed except that the product of Step 3 above was used in place of (4-fluorophenyl)(4-(2-hydroxyethoxy)phenyl)methanone to produce 1-(4-(allyloxy)phenyl)-1-(4-morpholinophenyl)prop-2-yn-1-ol. The product was used without further purification.

Step 5

The procedure of Step 5 of Example 7 of U.S. Pat. No. 7,465,415B2 was followed except that the product of Step 2 was used instead of 4,7,7-dimethyl-5-hydroxy-7Hbenzo[C]fluorene and the product of Step 4 was used instead of 1-(4-(2-hydroxyethoxy)phenyl)-1-(4-morpholinophenyl)prop-2-yn-1-ol to produce the product. NMR analysis showed the product to have a structure consistent with 3-(4-(allyloxy)phenyl)-3-(4-morpholinophenyl)-7-methoxy-1'-phenyl-13,13-dimethyl-3H,13H-indeno[2',3':3,4]naphtho[1,2-b]pyran as shown in the following graphic formula:

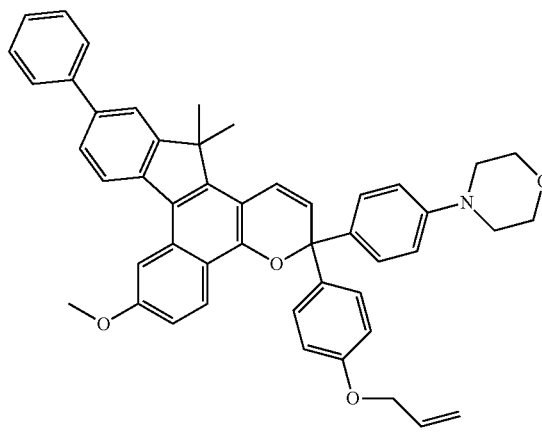

Example 23

Step 1

The product of Step 7 of Example 2 (2-methoxy-7,7-dimethyl-9-phenyl-7H-benzo[C]fluoren-5-ol (1.1 g)), 1-(4-bromophenyl)-1-(4-methoxyphenyl)-2-propyn-1-ol (1.24 g), PTSA (10 mg), and 20 ml of 1,2-dichloroethane were added heated to reflux for 8 hours in a 100 mL round bottom flask. The solvent was removed on a rotoevaporator and the product was as purified by column chromatography (silica gel, 100% dichloromethane as the eluent). The fractions containing product were combined and concentrated. The product was crystallized from dichloromethane and hexanes to yield 1.1 g of 3-(4-bromophenyl)-3'-(4-methoxyphenyl)-7-methoxy-1'-phenyl-13,13-dimethyl-3H,13H-indeno[2',3':3,4]naphtho[1,2-b]pyran.

Step 2

The product of Step 1, (1.0 g), 4-methyl-N-(4-methylphenyl)aniline (0.32 g), palladium(0)bis-(dibenzylideneacetone) (0.07 g), tri-tert-butylphosphine (1M in toluene, 0.09 ml), sodium tert-butoxide (0.22 g), and toluene (30 ml) were added to a flask under nitrogen. The reaction was then heated to 60° C. for 5 hours with stirring. Water and ethyl acetate were added to the reaction and the recovered organic layer was washed with brine and then dried over magnesium sulfate. The solvent was removed and the product was purified by column chromatography (silica gel, 50% hexanes in dichloromethane as the eluent). The fractions containing product were combined and concentrated. The product was crystallized from ethyl acetate and hexanes to yield 0.5 g of material. NMR analysis showed the product to have a structure consistent with 3-(4-(N,N-di-p-tolylaniline))-3-(4-methoxyphenyl)-7-methoxy-1'-phenyl-13,13-dimethyl-3H,13H-indeno[2',3':3,4]naphtho[1,2-b]pyran as shown in the following graphic formula:

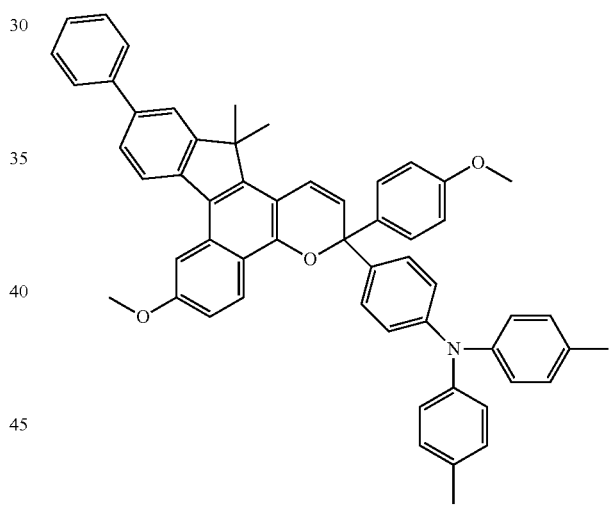

Example 24

Step 1

The product of Step 1 of Example 12 (7,7-dimethyl-9-phenyl-7H-benzo[c]fluoren-5-ol (1.1 g)), 1-(4-bromophenyl)-1-(4-methoxyphenyl)-2-propyn-1-ol (1.35 g), PTSA (10 mg), and 20 ml of 1,2-dichloroethane were heated to reflux for 8 hours in a 100 mL round bottom flask. The solvent was removed on a rotoevaporator and the product was as purified by column chromatography (silica gel, 100% dichloromethane as the eluent). The fractions containing product were combined and concentrated. The product was crystallized from dichloromethane and hexanes to yield 1.5 g of material. NMR analysis showed the product to have a structure consistent with 3-(4-bromophenyl)-3-(4-methoxyphenyl)-11-phenyl-13,13-dimethyl-3H,13H-indeno[2',3':3,4]naphtho[1,2-b]pyran.

Step 2

The product of Step 1 (1.4 g), 4-methyl-N-(4-methylphenyl)aniline (0.44 g), palladium(0)bis-(dibenzylideneacetone) (0.10 g), tri-tert-butylphosphine (1M in toluene, 0.09 ml), sodium tert-butoxide (0.32 g), and toluene (30 ml) were added to a reaction flask under nitrogen. The reaction was then heated to 60° C. for 5 hours with stirring. Water and ethyl acetate were added to the reaction and the organic layer was washed with brine and then dried over magnesium sulfate. The solvent was removed on a rotoevaporator and the product was as purified by column chromatography (silica gel, 50% hexanes in dichloromethane as the eluent). The fractions containing product were combined and concentrated. The product was crystallized from ethyl acetate and hexanes to yield 0.8 g of material. NMR analysis showed the product to have a structure consistent with 3-(4-(N,N-di-p-tolylaniline))-3-(4-methoxyphenyl)-1'-phenyl-13,13-dimethyl-3H,13H-indeno[2',3':3,4]naphtho[1,2-b]pyran as shown in the following graphic formula:

CE-1

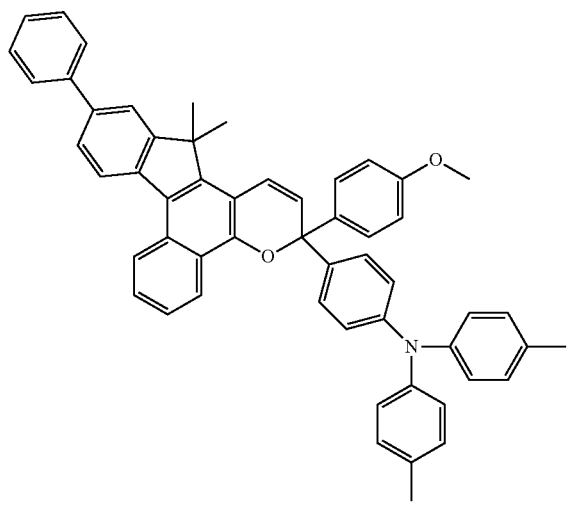 [SMILES: COc1ccc(C2(c3ccc(N(c4ccc(C)cc4)c4ccc(C)cc4)cc3)C=Cc3c4c(c5cc(OC)ccc5c3O2)-c2ccc(-c3ccccc3)cc2C4(C)C)cc1]

Step 1

In a flask placed under a nitrogen atmosphere, the product of Step 7 of CE-3, (7-methyl-9-phenyl-7H-benzo[c]fluorene-5,7-diol (0.70 g)) and pyridinium p-toluene sulfonate (0.10 g) were stirred in dichloromethane (50 mL). To this was added 1-(4-butoxyphenyl)-1-(4-methoxyphenyl)prop-2-yn-1-ol (0.77 g) in small amounts over 5 minutes. The reaction mixture was then heated to reflux for 1 hour. The reaction mixture was cooled to room temperature, then washed with a 50% v/v solution of saturated aqueous sodium bicarbonate in water (75 mL), washed with a saturated aqueous sodium chloride solution (75 mL), dried over sodium sulfate, and concentrated by rotary evaporation. The product was purified using a CombiFlash® Rf from Teledyne ISCO. The fractions were combined and concentrated using by rotary evaporation to yield (0.90 g) of product. An NMR spectrum showed that the structure was consistent with 3-(4-butoxyphenyl)-3-(4-methoxyphenyl)-1'-phenyl-13-hydroxy-13-methyl-3H,13H-indeno[2',3':3,4]naphtho[1,2-b]pyran as shown in the following graphic formula:

CE-2

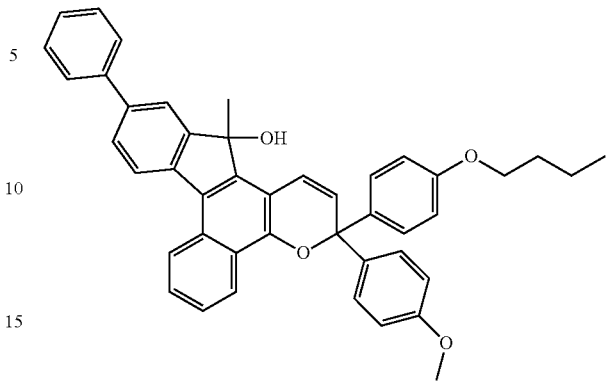

Step 1

In a flask placed under a nitrogen atmosphere, the product of CE-1, (3-(4-butoxyphenyl)-3-(4-methoxyphenyl)-1'-phenyl-13-hydroxy-13-methyl-3H,13H-indeno[2',3':3,4]naphtho[1,2-b]pyran (0.70 g)), and methanol (25 mL mL) were stirred in acetonitrile (25 mL). The mixture was heated to reflux and p-toluenesulfonic acid (0.10 g) was added. The mixture was heated to reflux for 2 hours. The reaction mixture was poured into water (150 mL) while stirring. The mixture was extracted with ethyl acetate (2×100 mL). The organic layers were recovered, combined, washed with a saturated aqueous solution of sodium bicarbonate (200 mL), washed with a saturated aqueous solution of sodium chloride (200 mL), dried over sodium sulfate, and concentrated by rotary evaporation. The product was purified using a CombiFlash® Rf from Teledyne ISCO. The pure fractions were combined and concentrated by rotary evaporation to yield 0.30 g of product. An NMR spectrum showed that the structure was consistent with 3-(4-butoxyphenyl)-3-(4-methoxyphenyl)-1'-phenyl-13-methoxy-13-methyl-3H,13H-indeno[2',3':3,4]naphtho[1,2-b]pyran as shown in the following graphic formula:

CE-3

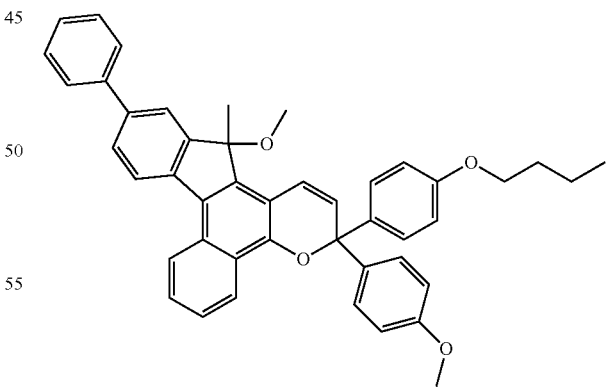

Step 1

In an oven-dried flask placed under a nitrogen atmosphere biphenyl (50 g) was stirred in dichloromethane (450 mL). The flask was placed in an ice bath and to it was added benzoyl chloride (46 mL) via addition funnel slowly over 20 minutes. To that mixture was added anhydrous aluminum chloride (51 g) via solid addition funnel, slowly over 10 minutes. After the aluminum chloride addition was complete the reaction mixture allowed to warm to room temperature and to stir for 16 hours. The reaction mixture was slowly poured into a beaker containing ice and a 10% aqueous solution of hydrochloric acid (600 mL) while stirring vigorously. A separatory funnel was used to separate the organic and aqueous layers. The recovered organic layer was then washed with water (2×500 mL), washed with a saturated aqueous solution of sodium chloride (500 mL), dried over sodium sulfate and concentrated by rotary evaporation. The resulting solid was slurried in a 25% v/v mixture of ethyl acetate in hexanes. The solid was collected by vacuum filtration, and then washed with cold diethyl ether (2×200 mL) to yield 57 g of [1,1'-biphenyl]-4-yl(phenyl)methanone.

Step 2

In an oven-dried flask placed under a nitrogen atmosphere, the product of Step 1 (57 g) and potassium tert-butoxide (39.6 g) were stirred in toluene (600 mL) using a mechanical stirrer. To this was added dimethyl succinate (33 mL) via addition funnel slowly over 20 minutes. The reaction mixture was stirred at room temperature for 4 hours. The reaction mixture was slowly poured into a beaker containing ice water (1 L) while stirring vigorously. Concentrated hydrochloric acid was slowly added to the mixture while stirring until pH 1 was reached. The mixture was extracted with ethyl acetate (2×750 mL). The organic layers were combined, washed with a saturated aqueous solution of sodium chloride (1 L), dried over sodium sulfate and concentrated by rotary evaporation to yield a dark orange colored oil yielding 81 g of a mixture of (E and Z) 4-([1,1'-biphenyl]-4-yl)-3-(methoxycarbonyl)-4-phenylbut-3-enoic acid.

Step 3

The product of Step 2 (81 g) was stirred in acetic anhydride (400 mL). The reaction mixture was heated to reflux for 5 hours. The acetic anhydride was subsequently removed via rotary evaporation. A dark red oil was isolated. The oil contained a mixture of 2 isomers: methyl 1-([1,1'-biphenyl]-4-yl)-4-acetoxy-2-naphthoate and methyl 4-acetoxy-1,6-diphenyl-2-naphthoate which together weighed 100 g. The product was used in the next reaction as is.

Step 4

The product from Step 3 was added to a flask under a nitrogen atmosphere and stirred in methanol (500 mL). To this was added concentrated hydrochloric acid (5 mL). The reaction mixture was heated to reflux for 16 hours and then cooled to room temperature. It was then concentrated by rotary evaporation. Recrystallization was achieved using ethyl acetate and hexanes. The pale yellow solid was collected via vacuum filtration yielding 15.4 g of methyl 1-([1,1'-biphenyl]-4-yl)-4-hydroxy-2-naphthoate.

Step 5

In a flask placed under a nitrogen atmosphere, the product of Step 4 (8 g) and a 20% w/w aqueous sodium hydroxide solution (63 mL) were stirred in methanol (120 mL). The reaction mixture was heated to reflux for 2.5 hours and then cooled to room temperature. The mixture was added to 200 mL water and then washed with diethyl ether (2×250 mL), which was discarded. A 10% aqueous solution of hydrochloric acid was added to the recovered aqueous layer while stirring until a pH of 1 was reached. The resulting precipitate was extracted with ethyl acetate (2×300 mL). The organic layers were combined and washed with a saturated aqueous solution of sodium chloride (300 mL), dried over sodium sulfate, and concentrated by rotary evaporation to provide a solid containing 1-([1,1'-biphenyl]-4-yl)-4-hydroxy-2-naphthoic acid and weighing 9.3 g which was used in the next reaction as is.

Step 6

In a flask placed under a nitrogen atmosphere, methanesulfonic acid (100 mL) was heated to 60° C. The product of Step 5 (7 g) that was finely ground was added to the mixture in small portions over 5 minutes. The mixture was stirred at 60° C. for 1 hour. The mixture was slowly poured into a beaker containing ice and water (1 L) while stirring vigorously. After 15 minutes, the resulting solid was collected by vacuum filtration and washed with water (2×200 mL). The solid was dissolved in dichloromethane (3.5 L) and washed with water (500 mL), then washed with a saturated aqueous solution of sodium chloride (500 mL). The recovered organic layer was dried over sodium sulfate, and concentrated by rotary evaporation. The solid was then dissolved in toluene in a flask equipped with a Dean-Stark trap under a nitrogen atmosphere and heated to reflux for 2 hours. The mixture was cooled to room temperature and concentrated by rotary evaporation to provide a solid containing 5-hydroxy-9-phenyl-7H-benzo[c]fluoren-7-one, weighing 7.5 g. The product was used in the next reaction as is.

Step 7

In an oven-dried flask placed under a nitrogen atmosphere, the product of Step 6 (4 g) was stirred in tetrahydrofuran anhydrous (100 mL). The flask was placed in an ice bath, and to it was added a 3.0M solution of methylmagnesium chloride in tetrahydrofuran (11 mL) slowly drop-wise via addition funnel over 20 minutes. After the addition was complete, the reaction mixture was warmed to room temperature and stirred for 2 hours. It was then slowly poured into beaker containing water (300 mL) while stirring. Dilute hydrochloric acid was added while stirring until a pH of 1 was reached. The mixture was extracted with ethyl acetate (2×300 mL). The recovered organic layers were combined, washed with a saturated aqueous solution of sodium bicarbonate (300 mL), washed with a saturated aqueous solution of sodium chloride (300 mL), dried over sodium sulfate and concentrated by rotary evaporation to yield an orange solid (3.4 g) containing 7-methyl-9-phenyl-7H-benzo[c]fluorene-5,7-diol. The product was used in the next reaction as is.

Step 8

In a flask placed under a nitrogen atmosphere, the product of Step 7 (2.5 g) and pyridinium p-toluene sulfonate (0.24 g) were stirred in dichloromethane (200 mL). To this was added 1,1-bis-(4-methoxyphenyl)prop-2-yn-1-ol (2.4 g) in small amounts over 5 minutes. The reaction mixture was then heated to reflux for 1.5 hours. The reaction mixture was cooled to room temperature, then washed with a 50% v/v solution of saturated aqueous sodium bicarbonate in water (200 mL), washed with a saturated aqueous sodium chloride solution (300 mL), dried over sodium sulfate, and concentrated by rotary evaporation. The product was purified using a CombiFlash®Rf from Teledyne ISCO. The pure fractions were combined and concentrated using by rotary evaporation. The resulting solid was slurried in diethyl ether and collected by vacuum filtration yielding 3.9 g of product. An NMR spectrum showed that the structure was consistent with 3,3-bis-(4-methoxyphenyl)-1'-phenyl-13-hydroxy-13-methyl-3H,13H-indeno[2',3':3,4]naphtho[1,2-b]pyran as shown in the following graphic formula:

CE-4

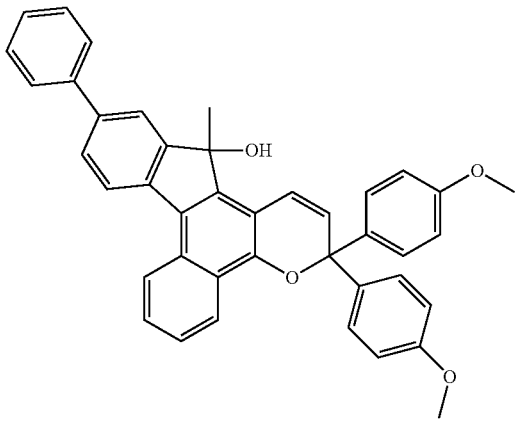

Step 1

In a flask placed under a nitrogen atmosphere, the product of CE-3,3,3-bis-(4-methoxyphenyl)-1'-phenyl-13-hydroxy-13-methyl-3H,13H-indeno[2',3':3,4]naphtho[1,2-b]pyran (1 g), and methanol (10 mL) were stirred in acetonitrile (35 mL). The mixture was heated to reflux and p-toluenesulfonic acid (0.09 g) was added. The mixture was allowed to reflux for 5 hours. The reaction mixture was poured into water (150 mL) while stirring. The mixture was extracted with ethyl acetate (2×100 mL). The organic layers were combined and washed with a saturated aqueous solution of sodium bicarbonate (200 mL), washed with a saturated aqueous solution of sodium chloride (200 mL), dried over sodium sulfate, and concentrated by rotary evaporation. The product was purified using a CombiFlash®Rf from Teledyne ISCO. The pure fractions were combined and concentrated by rotary evaporation to yield 120 mg of product. A portion of the material was dissolved in dichloromethane and upon exposure to ultraviolet light it became purple in color and faded after the UV light was removed. An NMR spectrum showed that the structure was consistent with 3,3-bis-(4-methoxyphenyl)-1'-phenyl-13-methoxy-13-methyl-3H,13H-indeno[2',3':3,4]naphtho[1,2-b]pyran as shown in the following graphic formula:

CE-5

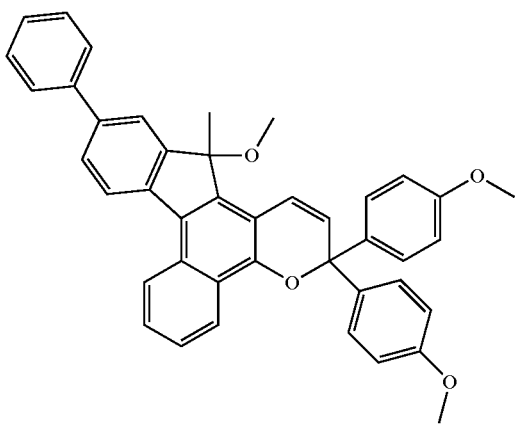

Step 1

In a flask placed under a nitrogen atmosphere, the product of Step 4 of Example 2, methyl 1-([1,1'-biphenyl]-4-yl)-4-acetoxy-7-methoxy-2-naphthoate (26.2 g) was stirred in methanol (40 mL) and a solution of 20% (w/v) sodium hydroxide in deionized water (200 mL). The reaction mixture was heated to reflux for 1.5 hours. After cooling to room temperature, the reaction mixture was slowly poured into a beaker containing deionized water (200 mL) and ice. Concentrated hydrochloric acid was added while stirring until the pH reached 1. The mixture was diluted with ethyl acetate and then transferred to a separatory funnel. The layers were separated and then the aqueous layer was extracted with ethyl acetate (2×75 mL). The organic layers were combined, washed with a saturated aqueous solution of sodium chloride (150 mL), dried over sodium sulfate and concentrated by rotary evaporation. The resulting residue (20.6 grams) contained methyl 1-([1,1'-biphenyl]-4-yl)-4-hydroxy-7-methoxy-2-naphthoic acid which was used in the next reaction as is.

Step 2

In an oven-dried flask placed under a nitrogen atmosphere and equipped with a Dean-Stark trap, the product of Step 1 (20.6 g) was stirred in xylenes (415 mL). To it was added dodecylbenzenesulfonic acid (5.5 g). The reaction mixture was heated to reflux for 6 hours. After cooling to room temperature, the reaction mixture was placed directly onto a column of silica gel (400 g) eluting with a solution of 60% ethyl acetate/40% hexanes. Fractions containing product were combined and concentrated by rotary evaporation. The resulting residue was dissolved in a minimal amount of a solution of 15% hexanes/85% toluene. A solid precipitated and was collected by vacuum filtration yielding 5.2 grams of product containing 5-hydroxy-2-methoxy-9-phenyl-7H-benzo[C]fluoren-7-one.

Step 3

In an oven-dried flask placed under a nitrogen atmosphere, the product of Step 2, (5.2 g) was stirred in tetrahydrofuran anhydrous (52 mL). The reaction flask was placed in an ice bath, and to it was added a 3M solution of methylmagnesium-chloride in tetrahydrofuran (15 mL) slowly drop-wise using an addition funnel over a 20 minute period. The reaction mixture was stirred at room temperature for 2 hours. It was then slowly poured into a saturated aqueous solution of ammonium chloride (150 mL) and ice while stirring. A separatory funnel was used to separate the layers. The resulting aqueous layer was extracted with ethyl acetate (2×50 mL). The recovered organic layers were combined, washed with a saturated aqueous solution of sodium bicarbonate (150 mL), dried over sodium sulfate and concentrated by rotary evaporation to yield a solid. The solid was slurried in a minimal amount of a solution of 15% ethyl acetate/85% hexanes and collected by vacuum filtration to yield 1.8 grams of a material containing 2-methoxy-5,7-dihydroxy-7-methyl-7H-benzo[C]fluorene.

Step 4

In an oven-dried flask placed under a nitrogen atmosphere, the product of Step 3 (1.7 g) and (1,1-bis-(4-methoxyphenyl)-2-propyn-1-ol, (1.6 g) were stirred in methylene chloride (34 mL). To this was added p-toluenesulfonic acid. The reaction mixture was stirred for 2 hours. It was then placed directly on a column of silica gel (300 g) eluting with a solution of 40% ethyl acetate/60% hexanes. Fractions containing product were combined and concentrated by rotary evaporation to yield a solid. The solid was slurried in a minimal amount of a solution of 15% ethyl acetate/85% hexanes and collected by vacuum filtration yielding 1.6 grams. A portion of the material was dissolved in ethylacetate and upon exposure to ultraviolet light it became purple in color and faded after the UV light was removed. NMR analysis indicates the product to have a structure consistent with 3,3-bis-(4-methoxyphenyl)-7-methoxy-1'-phenyl-13-hydroxy-13-methyl-3H,13H-indeno[2',3':3,4]naphtho[1,2-b]pyran as shown in the following graphic formula:

CE-6

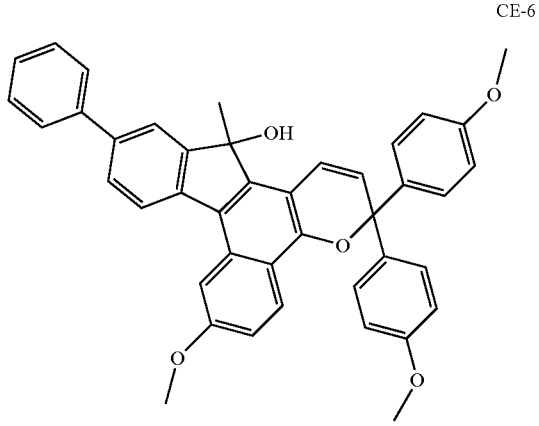 [SMILES: COc1ccc(C2(c3ccc(OC)cc3)C=Cc3c4c(c5cc(OC)ccc5c3O2)-c2ccc(-c3ccccc3)cc2C4(C)O)cc1]

In an oven-dried flask placed under a nitrogen atmosphere, the product of CE-5, (di(4-methoxyphenyl)-7-methoxy-1'-phenyl-13-hydroxy-13-methyl-3H,13H-indeno[2',3':3,4]naphtho[1,2-b]pyran (1.0 g)) was stirred in 1,2-dichloroethane (20 mL). To it was added trimethylorthoformate (0.9 mL) and pyridinium p-toluenesulfonate (60 mg). The reaction mixture was heated to reflux for 2 hours. After cooling to room temperature, it was transferred to a separatory funnel and washed with saturated aqueous solution of sodium bicarbonate (50 mL). The recovered organic layer was dried over sodium sulfate and concentrated by rotary evaporation. The resulting residue was purified by column chromatography on silica gel (100 g) eluting with a solution of 40% ethyl acetate/60% hexanes. Fractions containing product were combined and concentrated by rotary evaporation to yield a solid. The solid was slurried in a solution of 15% ethyl acetate/85% hexanes and collected by vacuum filtration to yield 0.25 grams of solid. A portion of the material was dissolved in ethylacetate and upon exposure to ultraviolet light it became purple in color and faded after the UV light was removed. NMR analysis indicates the product has a structure consistent with 3,3-bis-(4-methoxyphenyl)-7,13-dimethoxy-11-phenyl-13-methyl-3H,13H-indeno[2',3':3,4]naphtho[1,2-b]pyran as shown in the following graphic formula:

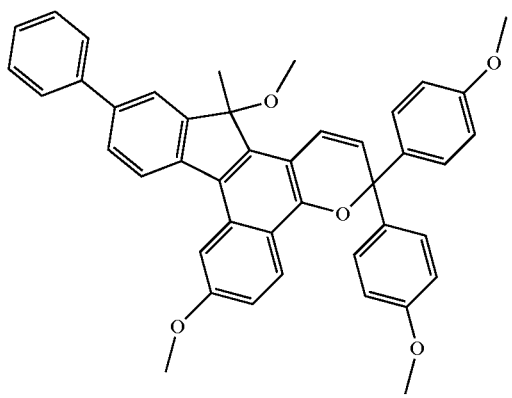 [SMILES: COc1ccc(C2(c3ccc(OC)cc3)C=Cc3c4c(c5cc(OC)ccc5c3O2)-c2ccc(-c3ccccc3)cc2C4(C)OC)cc1]

Part 2: Preparation and Fatigue Testing of Photochromic Coated Samples

Part 2-A: Preparation of Photochromic Coating Formulations

The following materials were added in the order described to a suitable vessel equipped with an agitator. The weight percent in each Charge is based on the total weight of the composition.

Charge 1—Weight Percent of Each Component is Listed

| Material | Weight Percent |
| --- | --- |
| NMP[1] | 24.3 |
| IRGANOX ® 245[2] | 0.53 |
| TINUVIN ® 144[3] | 0.53 |

[1]NMP, N-Methyl-2-pyrrolidone available from Aldrich of Milwaukee, Wisconsin
[2]IRGANOX ® 245—An antioxidant/stabilizer available from Ciba Specialty Chemicals Corp.
[3]TINUVIN ®-144 is a light stabilizer of the hindered amine class reported to have CAS# 63843-89-0 and is available from Ciba Specialty Chemicals.

Charge 2—Weight Percent of Each Component is Listed

| Material | Weight Percent |
| --- | --- |
| A-187[4] | 2.64 |
| BYK ® 333[5] | 0.04 |

[4]SILQUEST ® A-187 is a gamma-glycidoxypropyl trimethoxysilane, which is available from Osi Specities of Paris, France.
[5]BYK ® 333 is a polyether modified dimethylpolysiloxane compolymer, which is available from BYK-Chemie of Wallingford, Connecticut.

Charge 3—Weight Percent of Each Component is Listed

| Material | Weight Percent |
| --- | --- |
| HC-86-7726[6] | 16.2 |
| PC1122[7] | 15.9 |
| HDI Biuret BI-7960[8] | 28.0 |
| Desmodur ® PL-340[9] | 9.76 |

[6]PMAP—A poly(meth)acrylic polyol produced by following the procedure of Composition D of Example 1 in U.S. Pat. No. 6,187,444, which procedure is incorporated herein by reference, except that in Charge 2, the styrene was replaced with methyl methacrylate and 0.5% by weight, based on the total monomer weight, of triphenyl phosphite was added.
[7]PC-1122, reported to be a polycarbonate diol from Stahl USA.
[8]A blocked hexamethylene diisocyanate available from Baxenden Chemical Co. of Lancashire, England.
[9]A blocked aliphatic polyisocyanate based on IPDI available from Bayer MaterialScience LLC.

Charge 4—Weight Percent of Each Component is Listed

| Material | Weight Percent |
| --- | --- |
| PC-1[10] | 1.58 |

[10]The photochromic material of the Example or Comparative Example.

Charge 5—Weight Percent of Each Component is Listed

| Material | Weight Percent |
| --- | --- |
| K-KAT ® 348[11] | 0.53 |

[11]K-KAT ®348 is a urethane catalyst reported to be a bismuth carboxylate available from King Industries Inc.

Charge 1 was added to the vessel with mixing and heated to 60° C. for approximately 30 minutes to dissolve the solids. Charge 2 was added to the solution and the resulting mixture was stirred for approximately 10 minutes without heat. The materials of Charge 3 were premixed in a separate container and then added to the vessel containing Charges 1 and 2. The resulting mixture was stirred for 30 minutes and then added to a vessel containing Charge 4. This mixture was stirred with heat at 45° C. until Charge 4 was dissolved and thoroughly incorporated. Charge 5 was added to the final mixture and allowed to stir for 2 hours.

Part 2—B: Preparation of Photochromic Coated Articles

Finished single vision polycarbonate lenses having a diameter of 70 mm obtained from Gentex Optics were used. The test lenses were treated with a corona discharge from a Tantec EST-Electrical Service Treatment unit operating at 500 Watts and 54 kVA for 45 seconds. The coatings of Examples 1 & 2 and Comparative Examples 1-6 were each applied by spin-coating separately to the corona treated lens and cured at 125° C. for 60 minutes. The resulting cured coatings were approximately 20 microns thick.

The coated lenses from were treated with corona discharge from a Tantec EST-Electrical Service Treatment unit operating at 500 Watts and 54 kVA for 45 seconds. An acrylate-based formulation of the type described in Examples 1 and 2 of U.S. Pat. No. 7,410,691, which disclosure is incorporated herein by reference, was applied to the test lenses by spin coating and cured to result in coatings that were approximately 8 microns thick. The resulting photochromic lenses having two coatings were tested for fatigue as described below.

Part 2C: Procedures for Fatigue Testing and Results

Prior to initial performance testing on an optical bench, the photochromic samples were conditioned by exposing them to 365 nm ultraviolet light for 15 minutes at a distance of about 14 cm from the source in order to activate the photochromic molecules. The UVA irradiance at the sample was measured with a Licor Model Li-1800 spectroradiometer and found to be 22.2 Watts per square meter. The samples were then placed into an oven at 75° C. for 1 hour. The lenses were then exposed to room light for 3 hours. Finally, the samples were then kept in a dark environment for at least 1 hour prior to testing in order to continue to fade back to a ground state prior to testing.

An optical bench fitted with a Schott 3 mm KG-2 band-pass filter, neutral density filter(s) and a Newport Model#67005 300-watt Xenon arc lamp with Model#69911 power supply in association with a Newport Model 689456 Digital Exposure/Timer was used to control the intensity of the irradiance beam utilized for activation of the sample. A Uniblitz model# CS25S3ZMO high-speed shutter with model# VMM-D3 controller, and fused silica condensing lenses for activation beam collimation and focusing through a quartz water cell/sample holder for maintaining sample temperature in which the test sample to be tested was inserted. The temperature in the water cell was controlled with a pumped water circulation system in which the water passed through copper coils that were placed in the reservoir of a chiller unit. The water cell used to hold test samples contained fused silica sheets on the front and back facings in order to eliminate spectral change of the activation or monitoring light beams. The filtered water passing through the water cell was maintained at 100° F.±2° for photochromic testing before and after exposure to the Atlas Weatherometer.

A custom made broadband light source for monitoring response measurements was positioned in a perpendicular manner to a surface of the cell assembly. This broad beam light source is obtained by collecting and combining separately filtered light from a 100-Watt tungsten halogen lamp (controlled by a Lambda UP60-14 constant voltage powder supply) with a split-end, bifurcated fiber optical cable to enhance the short wavelength light intensity. After passing through the sample, this monitoring light was refocused into a 2-inch integrating sphere and fed to an Ocean Optics S2000 spectrophotometer by fiber optic cables. Ocean Optics SpectraSuite and PPG proprietary software were used to measure response and control the operation of the optical bench.

An International Light Research Radiometer, Model IL-1700 with a detector system comprising a Model SED033 detector, B Filter and diffuser was used to verify the irradiance prior to testing. An adjusted value of 18.0 W/m2 was used as the irradiance verification set point. The output display of the radiometer was corrected (factor values set) against a Licor 1800-02 Optical Calibration Calibrator in order to display values representing Watts per square meter UVA. Increasing or decreasing the current to the lamp through the controller and/or by adding or removing neutral density filters in the activation light path was done to make adjustments to the xenon lamp output. The test samples were exposed to activation light at 31° normal to the surface of the test sample. The temperature of the water cell was set to 100° F. to allow for quick activation to the saturated steady state.

The change in optical density (ΔOD) from the bleached state to the darkened state was determined by establishing the initial transmittance, opening the shutter from the Xenon lamp to provide ultraviolet radiation to change the test lens from the bleached state to an activated (i.e., darkened) state and measuring the transmittance in the activated state after typically 5 minutes of activation. The change in Optical density is calculated using the formula: $\Delta OD = \log(\% Tb/\% Ta)$, where % Tb is the percent transmittance in the bleached state, % Ta is the percent transmittance in the activated state and the logarithm is to the base 10. This provided the $OD_{init}$.

An Atlas Ci4000 weatherometer was used for conducting the simulated solar radiation accelerated weathering. The samples were exposed for a 1 hour dark cycle and then a 65 hour light cycle using a boro/boro silicate filtered Xenon arc lamp with an output of 0.25 Watts per square meter at 340 nm. The temperature in the weatherometer was maintained at 45° C. and the relative humidity was controlled at 70% humidity. The temperature of the black panel was maintained at 55° C.

After the lenses underwent this UV exposure fatigue cycle, the lenses were preconditioned as described above and measured on the optical bench to obtain the final $\Delta OD_{final}$ under the same conditions as described for the initial testing.

The percent fatigue was determined by measuring the difference between the change in optical density (ΔOD) of the test sample before and after accelerated weathering according to the formula: % Fatigue=$(\Delta OD_{init} - \Delta OD_{final})/\Delta OD_{init} \times 100$.

A second prominent measure used to describe the fatigue of the lens is the delta b* value. The delta b* value is the measured difference in the bleach state b* value as determined by the measured $b^*_{init}$ on the Hunter UltraScan Pro unit prior to exposure minus the measured $b^*_{final}$ value on the bleached state of the lens after this UV exposure fatigue cycle. This delta b* represents the amount of yellowing of the lens that occurs during fatigue. Desired results are low numbers for both the delta b* and % Photopic Fatigue.

The results in Table 1 show the difference in the fatigue of the lenses having a coating containing Example 1 versus Comparative Examples 1 and 2 conducted at the same time. The results in Table 2 show the difference in fatigue between Example 1 and Comparative Examples 3 and 4 and Example 2 and Comparative Examples 5 and 6, all tested at the same time.

TABLE 1

Percent Fatigue Results for Example 1 and CE-1 & 2

| Sample Description | delta b* | % Photopic Fatigue |
|---|---|---|
| Example 1 | 0.6 | 7 |
| CE-1 | 4.4 | 24 |
| CE-2 | 3.3 | 14 |

TABLE 2

Percent Fatigue Results for Examples 1 and 2 and CE-3-6

| Sample Description | delta b* | % Photopic Fatigue |
|---|---|---|
| Example 1 | 0.1 | 8 |
| CE-3 | 3.7 | 20 |
| CE-4 | 1.7 | 19 |
| Example 2 | 0.9 | 11 |
| CE-5 | 10.3 | 68 |
| CE-6 | 4.1 | 48 |

Part 3: Photochromic Performance Testing and Results

The photochromic performance of the photochromic materials of Examples 1-24 and CE-1-3 were tested as follows. A quantity of the photochromic material to be tested, calculated to yield a $1.5 \times 10^{-3}$ M solution, was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic material was dissolved into the monomer blend by stirring and gentle heating. After a clear solution was obtained, it was vacuum degassed before being poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours and then lower it to 60° C. for at least 2 hours. After the mold was opened, the polymer sheet was cut using a utility knife to score the surface and snap into 2 inch (5.1 cm) test squares.

The photochromic test squares prepared as described above were tested for photochromic response on an optical bench. Prior to testing on the optical bench, the photochromic test squares were exposed to 365 nm ultraviolet light for about 15 minutes to cause the photochromic material to transform from the ground state-form to an activated-state form, and then placed in a 75° C. oven for about 15 minutes to allow the photochromic material to revert back to the ground state-form. The test squares were then cooled to room temperature, exposed to fluorescent room lighting for at least 2 hours, and then kept covered (that is, in a dark environment) for at least 2 hours prior to testing on an optical bench maintained at 73° F. (23° C.). The bench was fitted with a 300-watt xenon arc lamp, a remote controlled shutter, a Melles Griot KG2 filter that modifies the UV and IR wavelengths and acts as a heat-sink, neutral density filter(s) and a sample holder, situated within a water bath, in which the square to be tested was inserted. A collimated beam of light from a tungsten lamp was passed through the square at a small angle (approximately 30°) normal to the square. After passing through the square, the light from the tungsten lamp was directed to a collection sphere, where the light was blended, and on to an Ocean Optics S2000 spectrometer where the spectrum of the measuring beam was collected and analyzed. The $\lambda_{max-vis}$ is the wavelength in the visible spectrum at which the maximum absorption of the activated-state form of the photochromic compound in a test square occurs. The $\lambda_{max-vis}$ wavelength was determined by testing the photochromic test squares in a Varian Cary 300 UV-Visible spectrophotometer; it may also be calculated from the spectrum obtained by the S2000 spectrometer on the optical bench.

The saturated optical density ("Sat'd OD") for each test square was determined by opening the shutter from the xenon lamp and measuring the transmittance after exposing the test chip to 3 W/m2 UVA radiation for 30 minutes. The $\lambda_{max-vis}$ at the Sat'd OD was calculated from the activated data measured by the S2000 spectrometer on the optical bench. The First Fade Half Life ("$T_{1/2}$") or Bleach Rate is the time interval in seconds for the absorbance of the activated-state form of the photochromic material in the test squares to reach one half the Sat'd OD absorbance value at room temperature (23° C.), after removal of the source of activating light.

| Example # | $\lambda_{max-vis}$ (nm) | Sensitivity (ΔOD/Min) | ΔOD at saturation | T ½ (sec) |
|---|---|---|---|---|
| 1 | 572 | 0.62 | 0.83 | 134 |
| 2 | 557 | 0.59 | 1.11 | 241 |
| 3 | 558 | 0.86 | 1.18 | 240 |
| 4 | 563 | 0.82 | 0.88 | 103 |
| 5 | 573 | 0.64 | 0.91 | 168 |
| 6 | 558 | 0.72 | 0.97 | 160 |
| 7 | 574 | 0.74 | 0.67 | 115 |
| 8 | 563 | 0.74 | 1.07 | 200 |
| 9 | 558 | 0.57 | 0.78 | 133 |
| 10 | 563 | 0.88 | 0.92 | 96 |
| 11 | 558 | 0.65 | 0.89 | 158 |
| 12 | 609 | 0.78 | 1.30 | 177 |
| 13 | 584 | 0.70 | 1.24 | 192 |
| 14 | 557 | 0.67 | 1.15 | 239 |
| 15 | 594 | 0.65 | 1.34 | 262 |
| 16 | 556 | 0.57 | 0.89 | 176 |
| 17 | 571 | 0.86 | 1.05 | 196 |
| 18 | 553 | 0.68 | 0.98 | 172 |
| 19 | 562 | 0.94 | 1.09 | 210 |
| 20 | 588 | 0.78 | 0.91 | 145 |
| 21 | 593 | 0.73 | 0.81 | 158 |
| 22 | 583 | 0.57 | 0.91 | 179 |
| 23 | 608 | 0.79 | 1.07 | 140 |
| 24 | 594 | 0.84 | 1.44 | 265 |
| CE-1 | 577 | 0.56 | 0.50 | 61 |
| CE-2 | 575 | 0.54 | 0.57 | 76 |
| CE-3 | 577 | 0.61 | 0.53 | 61 |

The present invention has been described with reference to specific details of particular embodiments thereof. It is not intended that such details be regarded as limitations upon the scope of the invention except insofar as and to the extent that they are included in the accompanying claims.

What is claimed is:

1. A photochromic material comprising an indeno-fused naphthopyran represented by at least one of the following Formula (I) and Formula (II),

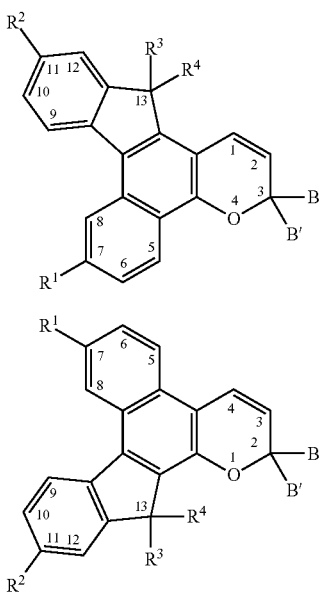

(I)

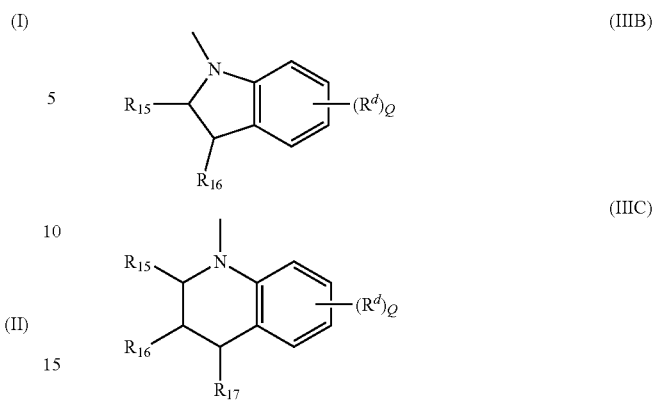

(IIIB)

(IIIC)

(II)

wherein independently for each of Formula (I) and Formula (II), $R^1$ is:

hydrogen, $R_5O-$, wherein $R_5$ is linear or branched $C_1-C_{20}$ alkyl, $C_3-C_{12}$ cycloalkyl, or $C_3-C_{12}$ heterocycloalkyl, $-N(R_{11}')R_{12}'$, wherein $R_{11}'$ and $R_{12}'$ are each independently hydrogen, $C_1-C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1-C_8$ alkylaryl, $C_3-C_{20}$ cycloalkyl, $C_4-C_{20}$ bicycloalkyl, $C_5-C_{20}$ tricycloalkyl or $C_1-C_{20}$ alkoxyalkyl, wherein said aryl group is phenyl or naphthyl, or $R_{11}$ and $R_{12}'$ come together with the nitrogen atom to form a $C_3-C_{20}$ hetero-bicycloalkyl ring or a $C_4-C_{20}$ hetero-tricycloalkyl ring, a nitrogen containing ring substituent represented by the following Formula (IIIA):

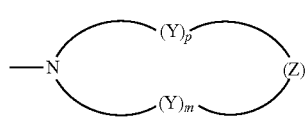

(IIIA)

wherein each $-Y-$ is independently for each occurrence $-CH_2-$, $-CH(R_{13}')-$, $-C(R_{13}')2-$, $-CH(aryl)-$, $-C(aryl)2-$, or $-C(R_{13}')(aryl)-$, and Z is $-Y-$, $-O-$, $-S-$, $-S(O)-$, $-SO_2-$, $-NH-$, $-N(R_{13}')-$, or $-N(aryl)-$, wherein each $R_{13}'$ is independently $C_1-C_6$ alkyl, each aryl is independently phenyl or naphthyl, m is an integer 1, 2 or 3, and p is an integer 0, 1, 2, or 3 and provided that when p is 0, Z is $-Y-$, a nitrogen containing ring substituent represented by Formula (IIIB) and/or Formula (IIIC):

wherein $R_{15}$, $R_{16}$, and $R_{17}$ are each independently hydrogen, $C_1-C_6$ alkyl, phenyl, or naphthyl, or the groups $R_{15}$ and $R_{16}$ together form a ring of 5 to 8 carbon atoms and each $R^d$ independently for each occurrence is $C_1-C_6$ alkyl, $C_1-C_6$ alkoxy, fluoro or chloro, and Q is an integer 0, 1, 2, or 3, $R^2$ is optionally substituted aryl, optionally substituted heteroaryl, optionally substituted fused ring polycyclic-aryl-alkyl groups in which an aryl ring is directly bonded to Position-11, the optional aryl substituents, optional heteroaryl substituents, and optional polycyclic-aryl-alkyl fused ring substituents each being selected from the group consisting of hydroxyl, halo, carbonyl, $C_1-C_6$ alkoxycarbonyl, cyano, halo($C_1-C_6$)alkyl, $C_1-C_6$ alkyl, $C_1-C_6$ alkoxy, $-N(R_{11}')R_{12}'$ wherein $R_{11}'$ and $R_{12}'$ are each as described above, said nitrogen containing ring substituent represented by Formula (IIIA) wherein Formula (IIIA) is a described above, optionally substituted $C_3-C_{12}$ heterocycloalkyl, optionally substituted aryl, and optionally substituted heteroaryl, $R^3$ and $R^4$ are each independently selected from the group consisting of optionally substituted linear or branched $C_1-C_{20}$ alkyl, optionally substituted $C_3-C_{12}$ cycloalkyl, optionally substituted $C_3-C_{12}$ heterocycloalkyl, $-R_5'-OH$ where $R_5'$ is selected from linear or branched $C_1-C_{20}$ alkyl and $C_3-C_{12}$ cycloalkyl, and $-C(O)OR_6'$ where $R_6'$ is selected from linear or branched $C_1-C_{20}$ alkyl and $C_3-C_{12}$ cycloalkyl, and B and B' are each independently, an aryl group that is mono-substituted with a reactive substituent or a compatiblizing substituent; an unsubstituted aryl group; a mono-, di-, tri- or tetra-substituted aryl group; 9-julolidinyl; an unsubstituted, mono- or di-substituted heteroaromatic group selected from the group consisting of pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl and fluorenyl;

wherein the aryl and heteroaromatic substituents are each independently, hydroxy, halo, aryl, mono- or di-($C_1-C_{12}$)alkoxyaryl, mono- or di-($C_1-C_{12}$)alkylaryl, haloaryl, $C_3-C_7$ cycloalkylaryl, $C_3-C_7$ cycloalkyl, $C_3-C_7$ cycloalkyloxy, $C_3-C_7$ cycloalkyloxy($C_1-C_{12}$)alkyl, $C_3-C_7$ cycloalkyloxy($C_1-C_{12}$)alkoxy, aryl($C_1-C_{12}$)alkyl, aryl($C_1-C_{12}$)alkoxy, aryloxy, aryloxy($C_1-C_{12}$)alkyl, aryloxy($C_1-C_{12}$)alkoxy, mono- or di-($C_1-C_{12}$)alkylaryl($C_1-C_{12}$)alkyl, monoor di-($C_1$-$C_{12}$)alkoxyaryl($C_1$-$C_{12}$)alkyl, mono- or di-($C_1$-$C_{12}$)alkylaryl($C_1$-$C_{12}$)alkoxy, mono- or di-($C_1$-$C_{12}$)alkoxyaryl($C_1$-$C_{12}$)alkoxy, amino, mono- or di-($C_1$-$C_{12}$)alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, linear or branched $C_1$-$C_{12}$ alkyl, linear or branched $C_1$-$C_{12}$ haloalkyl, linear or branched $C_1$-$C_{12}$ alkoxy, mono($C_1$-$C_{12}$)alkoxy($C_1$-$C_{12}$)alkyl, acryloxy, methacryloxy, halogen, or —C(=O)$R^{21}$ wherein $R^{21}$ is —$OR^{22}$, —N($R^{23}$)$R^{24}$, piperidino or morpholino, wherein $R^{22}$ is allyl, $C_1$-$C_6$ alkyl, phenyl, mono($C_1$-$C_6$)alkyl substituted phenyl, mono($C_1$-$C_6$) alkoxy substituted phenyl, phenyl($C_1$-$C_3$)alkyl, mono ($C_1$-$C_6$)alkyl substituted phenyl($C_1$-$C_3$)alkyl, mono ($C_1$-$C_6$)alkoxy substituted phenyl($C_1$-$C_3$)alkyl, $C_1$-$C_6$alkoxy($C_2$-$C_4$)alkyl or $C_1$-$C_6$ haloalkyl, and $R^{23}$ and $R^{24}$ are each independently $C_1$-$C_6$ alkyl, $C_5$-$C_7$ cycloalkyl or a substituted or unsubstituted phenyl, said phenyl substituents independently being $C_1$-$C_6$ alkyl or $C_1$-$C_6$ alkoxy, or an unsubstituted or mono-substituted group selected from the group consisting of pyrazolyl, imidazolyl, pyrazolinyl, imidazolinyl, pyrrolidyl, phenothiazinyl, phenoxazinyl, phenazinyl and acridinyl, said substituents being $C_1$-$C_{12}$ alkyl, $C_1$-$C_{12}$ alkoxy, phenyl or halogen, or a mono-substituted phenyl, said mono-substituted phenyl having a substituent located at the para position, the substituent being a dicarboxylic acid residue or derivative thereof, a diamine residue or derivative thereof, an amino alcohol residue or derivative thereof, a polyol residue or derivative thereof, —(CH$_2$)—, —(CH$_2$)$_t$— or —[O—(CH$_2$)$_t$]$_k$—, wherein t ranges from 2 to 6 and k ranges from 1 to 50, and wherein the substituent is connected to an aryl group on another photochromic material, or a group represented by the following Formula (IVA) and/or Formula (IVB):

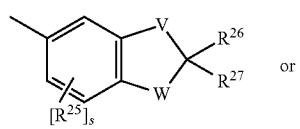

(IVA)

or

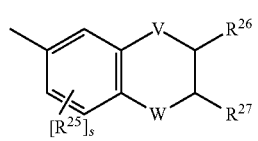

(IVB)

wherein V is —CH$_2$— or —O—, W is oxygen or substituted nitrogen, provided that when W is substituted nitrogen, V is —CH$_2$—, the substituted nitrogen substituents being hydrogen, $C_1$-$C_{12}$ alkyl or $C_1$-$C_{12}$ acyl, each $R^{25}$ independently being $C_1$-$C_{12}$ alkyl, $C_1$-$C_{12}$ alkoxy, hydroxy or halogen, $R^{26}$ and $R^{27}$ are each independently hydrogen or $C_1$-$C_{12}$ alkyl, and s ranges from 0 to 2, or a group represented by the following Formula (V):

(V)

wherein $R^{28}$ is hydrogen or $C_1$-$C_{12}$ alkyl, and $R^{29}$ is an unsubstituted, mono- or di-substituted naphthyl, phenyl, furanyl or thienyl, said substituents being $C_1$-$C_{12}$ alkyl, $C_1C_{12}$ alkoxy or halogen, or B and B' taken together form a fluoren-9-ylidene or mono- or di-substituted fluoren-9-ylidene, each of said fluoren-9-ylidene substituents independently being $C_1$-$C_{12}$ alkyl, $C_1$-$C_{12}$ alkoxy or halogen, provided that $R^3$ and $R^4$ each are not selected from hydroxyl and $R_6$O—, where $R_6$ is selected from optionally substituted alkyl, optionally substituted cycloalkyl, optionally substituted heterocycloalkyl, optionally substituted aryl, and optionally substituted heteroaryl.

2. The photochromic material of claim 1, wherein said indeno-fused naphthopyran is represented by Formula (I).

3. The photochromic material of claim 2, wherein $R^1$ is hydrogen, $R_5$O—, wherein $R_5$ is linear or branched $C_1$-$C_{20}$ alkyl, and a nitrogen containing ring substituent represented by general Formula (IIIA):

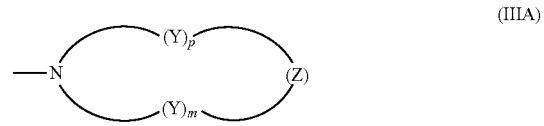

(IIIA)

wherein each —Y— is independently or each occurrence —CH$_2$—, —CH($R_{13}$')—, or —C($R_{13}$')$_2$—, and Z is —Y—, or —O—, wherein each $R_{13}$' is independently linear or branched $C_1$-$C_6$ alkyl, m is an integer 1, 2 or 3, and p is an integer 0, 1, 2, or 3, and provided that when p is 0, Z is —Y—, $R^2$ is optionally substituted phenyl, the optional phenyl substituents being selected the group consisting of from halo, cyano, linear or branched halo($C_1$-$C_6$)alkyl, linear or branched $C_1$-$C_6$ alkyl, and linear or branched $C_1$-$C_6$ alkoxy, $R^3$ and $R^4$ are each independently linear or branched $C_1$-$C_{20}$ alkyl, and B and B' are each independently, an unsubstituted phenyl group, or a mono-, di-, tri- or tetra-substituted phenyl group, the phenyl substituents being selected from the group consisting of fluoro, linear or branched $C_1$-$C_{12}$ alkyl, linear or branched $C_1$-$C_{12}$ haloalkyl, linear or branched $C_1$-$C_{12}$ alkoxy, piperidino, and morpholino.

4. The photochromic material of claim 3, wherein $R^1$ is, hydrogen, $R_5$O—, wherein $R_5$ is linear or branched $C_1$-$C_6$ alkyl, or a nitrogen containing ring substituent represented by Formula (IIIA), which is selected from the group consisting of piperidino and morpholino, R² is optionally substituted phenyl, the optional phenyl substituents being selected from the group consisting of halo, linear or branched halo(C₁-C₆)alkyl, and linear and branched C₁-C₆ alkyl, R³ and R⁴ are each independently linear or branched C₁-C₆ alkyl, and B and B' are each independently,
an unsubstituted phenyl group, or a mono-, di-, tri- or tetra-substituted phenyl group, the phenyl substituents being selected from the group consisting of fluoro, linear or branched C₁-C₆ alkyl, linear or branched C₁-C₆ alkoxy, piperidino, and morpholino.

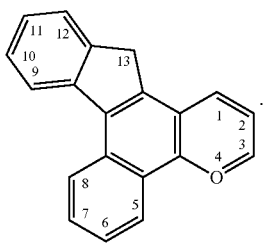

5. A photochromic article comprising the photochromic material of claim 1.

6. The photochromic article of claim 5, wherein said photochromic article is selected from the group consisting of ophthalmic articles, display articles, windows, mirrors, and active liquid crystal cell articles, and passive liquid crystal cell articles.

7. The photochromic article of claim 6, wherein said photochromic article is selected from the group consisting of ophthalmic articles, and said ophthalmic articles are selected from corrective lenses, non-corrective lenses, contact lenses, intra-ocular lenses, magnifying lenses, protective lenses, and visors.

8. The photochromic article of claim 6, wherein said photochromic article is selected from the group consisting of display articles, and said display articles are selected from screens, monitors, and security elements.

9. A photochromic composition comprising the photochromic material of claim 1 incorporated into at least a portion of an organic material, wherein said organic material is a polymeric material, an oligomeric material, a monomeric material, a mixture of two or more thereof, or a combination of two or more thereof.

10. The photochromic composition of claim 9, wherein the organic material is a polymeric material, said polymeric material being a poly(carbonate); a copolymer of ethylene and vinyl acetate; a copolymer of ethylene and vinyl alcohol; a copolymer of ethylene, vinyl acetate and vinyl alcohol; cellulose acetate butyrate; poly(urethane); poly(acrylate); poly(methacrylate); epoxy; an aminoplast functional polymer; poly(anhydride); poly(urea urethane); a N-alkoxymethyl(meth)acrylamide functional polymer; poly(siloxane); poly(silane); a mixture of two or more thereof; or a combination of two or more thereof.

11. The photochromic composition of claim 9, wherein the photochromic composition further comprises at least one of, a complementary photochromic material, a photoinitiator, a thermal initiator, a polymerization inhibitor, a solvent, a light stabilizer, a heat stabilizer, a mold release agent, a rheology control agent, a leveling agent, a free radical scavenger, and an adhesion promoter.

12. The photochromic composition of claim 9, wherein the photochromic composition is a coating composition.

13. A photochromic material comprising an indeno-fused naphthopyran selected from at least one of,
(a) 3-(4-butoxyphenyl)-3-(4-methoxyphenyl)-11-phenyl-13,13-dimethyl-3H,13H-indeno[2',3':3,4]naphtho[1,2-b]pyran,
(b) 3,3-bis-(4-methoxyphenyl)-11-phenyl-13,13-dimethyl-3H,13H-indeno[2',3':3,4]naphtho[1,2-b]pyran,
(c) 3-(4-butoxyphenyl)-3-(4-methoxyphenyl)-7-methoxy-11-phenyl-13,13-dimethyl-3H,13H-indeno[2',3':3,4]naphtha[1,2-b]pyran,
(d) 3,3-bis-(4-methoxyphenyl)-7-methoxy-11-phenyl-13,13-dimethyl-3H,13H-indeno[2',3':3,4]naphtho[1,2-b]pyran,
(e) 3-(4-butoxypheny)-3-(4-methoxyphenyl)-7-morpholino-11-phenyl-13,13-dimethyl-3H,13H-indeno [2',3':3,4]naphtho[1,2-b]pyran,
(f) 3,3-bis-(4-methoxyphenyl)-7-morpholino-11-phenyl-13,13-dimethyl-3H,13H-indeno[2',3':3,4]naphtha[1,2-b]pyran,
(g) 3,3-bis-(4-hydroxyphenyl)-7-methoxy-11-phenyl-13,13-diethyl-3H,13H-indeno[2',3':3,4]naphtho[1,2-b]pyran,
(h) 3-(4-butoxyphenyl)-3-(4-methoxyphenyl)-7-methoxy-11-phenyl-13,13-dipropyl-3H,13H-indeno[2',3':3,4]naphtho[1,2-b]pyran,
(i) 3-(4-butoxyphenyl)-3-(4-methoxyphenyl)-7-methoxy-11-(2,4-dimethoxyphenyl)-13,13-dipropyl-3H,13H-indeno[2',3':3,4]naphtho[1,2-b]pyran,
(j) 3,3-bis-(4-hydroxyphenyl)-7-methoxy-11-phenyl-13,13-dipropyl-3H,13H-indeno [2',3':3,4]naphtho[1,2-b]pyran
(k) 3-phenyl-3-(4-piperidinophenyl)-11-phenyl-13,13-dimethyl-3H,13H-indeno[2',3':3,4]naphtho[1,2-b]pyran,
(l)3-(4-fluorophenyl)-3-(4-morpholinophenyl)-11-phenyl-13,13-dimethyl-3H,13H-indeno[2',3':3,4]-naphthol[1,2-b]pyran,
(m) 3,3-bis-(4-methoxyphenyl)-11-(2,4-dimethoxyphenyl)-13,13-dimethyl-3H,13H-indeno[2',3':3,4]naphtho[1,2-b]pyran,
(n) 3,3-bis-(4-methoxyphenyl)-11-(4-(4,5-diphenyl-1H-imidazol-2-yl)phenyl)-13,13-dimethyl-3H,13H-indeno[2',3':3,4]-naphtho[1,2-b]pyran,
(o) 3,3-bis-(4-methoxyphenyl)-7-methoxy-11-phenyl-13-carbomethoxy-13-methyl-3H,13H-[indeno2',3':3,4]-naphtho [1,2-b]pyran,
(p) 3,3-bis-4-methoxphenyl-7-methoxy-11-phenyl-13-hydroxymethyl-13-methyl-3H,13H-indeno[2',3':3,4] naphtho[1,2-b]pyran,
(q) 3-(4-butoxyphenyl)-3-(4-morpholinophenyl)-7-methoxy-11 -(2-methoxyphenyl)-13,13-dimethyl-3H,13H-indeno[2',3':3,4]naphtho[1,2-b]pyran,
(r) 3,3-bis-(4-butoxyphenyl)-7-methoxy-11-phenyl-13,13-dimethyl-3H,13H-indeno[2',3':3,4]naphtho[1,2-b]pyran,
(s) 3-(4-morpholinophenyl)-3-phenyl-11-(4-t-butylphenyl)-13,13-dimethyl-3H-13H-indeno[2',3':3,4]naphtho[1,2-b]pyran,
(t) 3-(4-butoxyphenyl)-3-(4-fluorophenyl)-11-(2,4-difluorophenyl)-13,13-dimethyl-3H,13H-indeno[2',3':3,4] naphtho[1,2-b]pyran,
(u) 3-(4-butoxyphenyl)-3-(4-fluorophenyl)-11-(9,9-bis-(2-ethylhexyl)-9H-fluoren-2-yl)-13,13-dimethyl-3H,13H-indeno[2',3':3,4]naphtho[1,2-b]pyran, (v) 3-(4-butoxyphenyl)-3-(4-methoxyphenyl)-7-methoxy-11-(5-pyrimidinyl)-13,13-dimethyl-3H,13H-indeno[2',3':3,4]naphtho[1,2-b]pyran, (w) 3(4-butoxyphenyl)-3-(4-methoxyphenyl)-7-methoxy-11-(9,9-bis-(2-ethylhexyl)-9H-fluoren-2-yl)-13,13-dimethyl-3H,13H-indeno[2',3':3,4]naphtho[1,2-b]pyran, (x) 3-(4-morpholinophenyl)-3-(4-methoxyphenyl)-7-methoxy-11-(9,9-bis-(2-ethylhexyl)-9H-fluoren-2-yl)-13,13-dimethyl-3H,13H-indeno[2',3':3,4]naphtho[1,2-b]pyran, (y) 3-(4-(2-hydroxyethoxy)phenyl)-3-(4-methoxyphenyl)-11-(4-(N,N-dimethylamino)phenyl)-13,13 -dimethyl-3H,13H-indeno[2',3'3,4]naphtho[1,2-b]pyran, (z) 3-(4-allyloxy)phenyl)-3-(4-morpholinophenyl)-7-methoxy-11-phenyl-13,13-dimethyl-3H,13H-indeno[2',3:3,4]naphtho[1,2-b]pyran, (aa) 3-(4-N,N-di-p-tolyaniline))-3-(4-methoxyphenyl)-7-methoxy-11-phenyl-13,13-dimethyl-3H,13H-indeno[2',3':3,4]naphtho[1,2-b]pyran, and (bb) 3-(4-(N,N-di-p-tolylaniline))-3-(4-methoxyphenyl)-11-phenyl-13,13-dimethyl-3H,13H-indeno[2',3':3,4]naphtho[1,2-b]pyran, wherein each indeno-fused naphthopyran has an indeno[2',3':3,4]naphtha[1,2b]pyran core structure represented by the following Formula.

\* \* \* \* \*